US010294279B2

(12) United States Patent
Langedijk et al.

(10) Patent No.: US 10,294,279 B2
(45) Date of Patent: May 21, 2019

(54) STABILIZED SOLUBLE PRE-FUSION RSV F POLYPEPTIDES

(71) Applicant: Janssen Vaccines & Prevention B.V., Leiden (NL)

(72) Inventors: Johannes P. M. Langedijk, Amsterdam (NL); Anders Krarup, Leiden (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 68 days.

(21) Appl. No.: 14/899,531

(22) PCT Filed: Jun. 17, 2014

(86) PCT No.: PCT/EP2014/062655
§ 371 (c)(1),
(2) Date: Dec. 17, 2015

(87) PCT Pub. No.: WO2014/202570
PCT Pub. Date: Dec. 24, 2014

(65) Prior Publication Data
US 2016/0176932 A1    Jun. 23, 2016

(30) Foreign Application Priority Data

Jun. 17, 2013   (EP) .................................. 13172256

(51) Int. Cl.
C07K 14/005    (2006.01)
C12N 7/00      (2006.01)
A61K 39/00     (2006.01)

(52) U.S. Cl.
CPC .............. *C07K 14/005* (2013.01); *C12N 7/00* (2013.01); *A61K 39/00* (2013.01); *C07K 2319/73* (2013.01); *C12N 2760/18522* (2013.01); *C12N 2760/18534* (2013.01); *C12N 2999/002* (2013.01)

(58) Field of Classification Search
None
See application file for complete search history.

(56) References Cited

U.S. PATENT DOCUMENTS

| 4,235,877 A | 11/1980 | Fullerton |
| 4,372,945 A | 2/1983 | Likhite |
| 4,474,757 A | 10/1984 | Arnon et al. |
| 5,057,540 A | 10/1991 | Kensil et al. |
| 5,122,458 A | 6/1992 | Post et al. |
| 5,385,839 A | 1/1995 | Stinski |
| 5,559,099 A | 9/1996 | Wickham et al. |
| 5,837,511 A | 11/1998 | Falck-Pedersen et al. |
| 5,837,520 A | 11/1998 | Shabram et al. |
| 5,846,782 A | 12/1998 | Wickham et al. |
| 5,851,806 A | 12/1998 | Kovesdi et al. |
| 5,891,690 A | 4/1999 | Massie |
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,113,913 A | 9/2000 | Brough et al. |
| 6,225,289 B1 | 5/2001 | Kovesdi et al. |
| 6,261,823 B1 | 7/2001 | Tang |
| 6,485,958 B2 | 11/2002 | Blanche et al. |
| 7,270,811 B2 | 9/2007 | Bout et al. |
| 7,326,555 B2 | 2/2008 | Konz, Jr. et al. |
| 2011/0305727 A1 | 12/2011 | Swanson et al. |
| 2012/0164176 A1 | 6/2012 | Swanson et al. |
| 2012/0315270 A1 | 12/2012 | McLellan et al. |
| 2013/0177573 A1 | 7/2013 | Williamson et al. |
| 2013/0315270 A1 | 11/2013 | Kumazaki et al. |
| 2014/0073032 A1 | 3/2014 | Custers et al. |
| 2014/0248314 A1 | 9/2014 | Swanson |
| 2014/0271699 A1 | 9/2014 | Kwong et al. |
| 2016/0102123 A1 | 4/2016 | Langedijk et al. |
| 2016/0145321 A1 | 5/2016 | Wadia et al. |
| 2016/0145322 A1 | 5/2016 | Wadia et al. |
| 2016/0176932 A1 | 6/2016 | Langedijk et al. |

FOREIGN PATENT DOCUMENTS

| EP | 0853660 A1 | 7/1998 |
| EP | 1230354 A0 | 8/2002 |
| WO | 9003184 A1 | 4/1990 |
| WO | 9014837 A1 | 12/1990 |
| WO | 9609378 A1 | 3/1996 |
| WO | 9611711 A1 | 4/1996 |
| WO | 98/22588 A2 | 5/1998 |
| WO | 98/39411 A1 | 9/1998 |
| WO | 99/12568 A1 | 3/1999 |
| WO | 99/41416 A2 | 8/1999 |
| WO | 2000/29024 A1 | 5/2000 |
| WO | 2000/32754 A1 | 6/2000 |
| WO | 2000/70071 A1 | 11/2000 |
| WO | 2001/66137 A1 | 9/2001 |
| WO | 2002/40665 A2 | 5/2002 |
| WO | 03040178 A1 | 5/2003 |
| WO | 2003/049763 A1 | 6/2003 |
| WO | 2003/061708 A1 | 7/2003 |
| WO | 2003/078592 A2 | 9/2003 |
| WO | 2003/104467 A1 | 12/2003 |
| WO | 2004004762 A1 | 1/2004 |
| WO | 2004/020971 A2 | 3/2004 |
| WO | 2005002620 A1 | 1/2005 |
| WO | 2005/080556 A2 | 9/2005 |
| WO | 2006/108707 A1 | 10/2006 |
| WO | 2007/104792 A2 | 9/2007 |
| WO | 2007/110409 A1 | 10/2007 |

(Continued)

OTHER PUBLICATIONS

McClellan et al Science vol. 342, p. 592ff, 2013.*

(Continued)

*Primary Examiner* — Shanon A. Foley
*Assistant Examiner* — Myron G Hill
(74) *Attorney, Agent, or Firm* — Panitch Schwarze Belisario & Nadel LLP

(57) ABSTRACT

This disclosure provides stable pre-fusion respiratory syncytial virus (RSV) F polypeptides, immunogenic compositions comprising the polypeptides, and uses thereof for the prevention and/or treatment of RSV infection.

22 Claims, 7 Drawing Sheets

Figure 1:
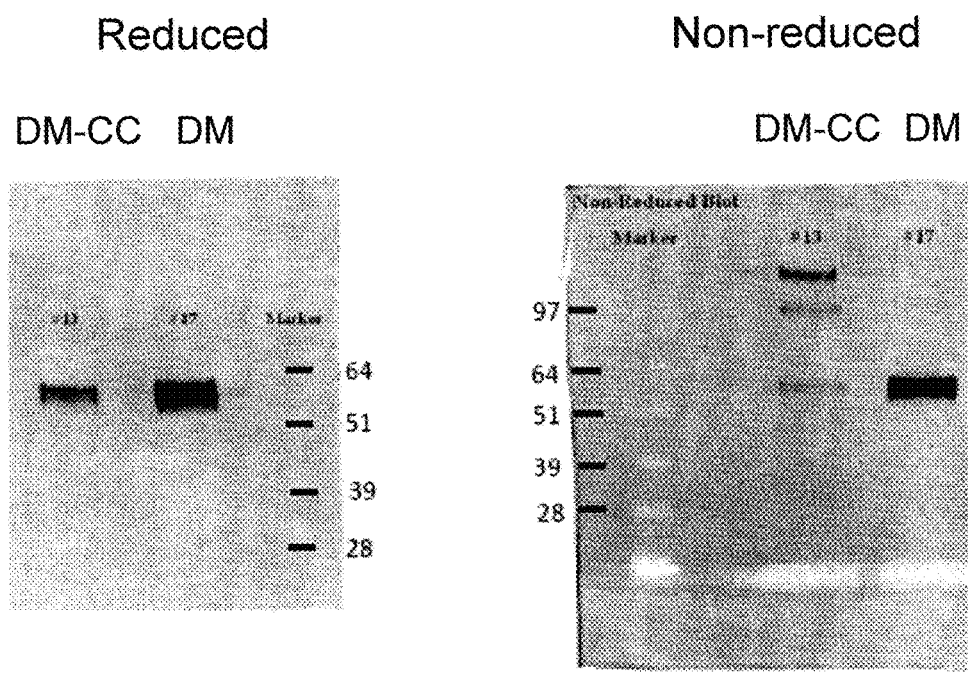
Figure 2:
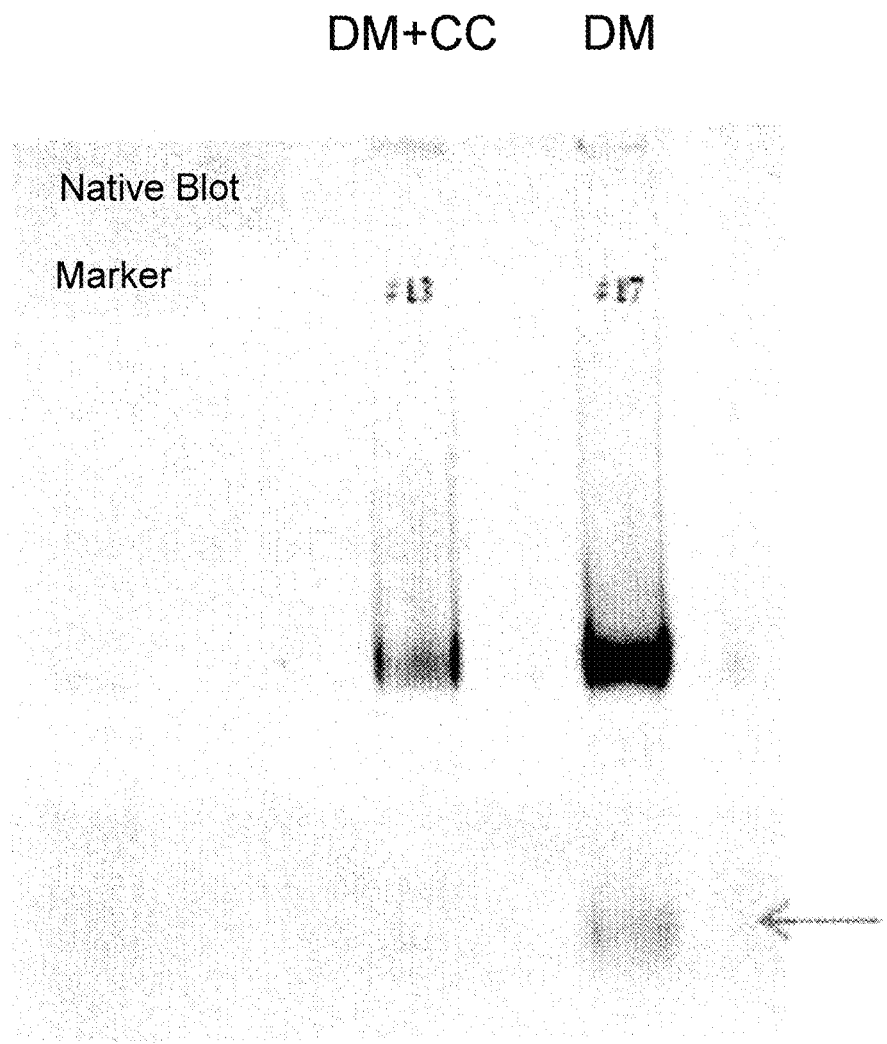

Specification includes a Sequence Listing.

(56) References Cited

FOREIGN PATENT DOCUMENTS

| WO | 2009/11713 | A1 | 1/2009 |
|---|---|---|---|
| WO | 2009079796 | A1 | 7/2009 |
| WO | 2010/060719 | A1 | 6/2010 |
| WO | 2010149743 | A2 | 12/2010 |
| WO | 2010149745 | A1 | 12/2010 |
| WO | 2011008974 | | 1/2011 |
| WO | 2011/020079 | A1 | 2/2011 |
| WO | 2011/045378 | A1 | 4/2011 |
| WO | 2011/045381 | A1 | 4/2011 |
| WO | 2011050168 | | 4/2011 |
| WO | 2011/098592 | A1 | 8/2011 |
| WO | 2012006596 | A2 | 1/2012 |
| WO | 2012158613 | A1 | 11/2012 |
| WO | WO 2012158613 | A1 * | 11/2012 |
| WO | 2013/139911 | A1 | 9/2013 |
| WO | 2013/139916 | A1 | 9/2013 |
| WO | 2013135615 | A1 | 9/2013 |
| WO | 2014160463 | A1 | 10/2014 |
| WO | 2014174018 | A1 | 10/2014 |
| WO | 2014202570 | A1 | 12/2014 |

OTHER PUBLICATIONS

McClellan et al (Science vol. 340, p. 1114, col. 2 upper part, 2013.*
Calder L. J. et al., Virology 271, 122-131 (2000).
Dames-SA et. al., Nat. Struc. Biol., 5(8), (1998).
Guthe et al., J. Mol. Biol. 337: 905-915. (2004).
Harbury et al., Science 262: 1401-1407 (1993).
Letarov et al., Biochemistry Moscow 64: 817-823 (1993).
McLellan et al., Nature Struct. Bio1.17: 2-248-250 (2010).
O'Shea et al., Science 243: 538-542 (1989).
Suzuki et al., Protein Engineering 11: 1051-1055 (1998).
Database EMBL, Aug. 28, 1995, Human respiratory syncytial virus, strain RSB89-1734, fusion protein (F) mRNA, complete CDS, XP002729919.
McLellan et al., Structure-Based Design of a Fusion Glycoprotein Vaccine for Respiratory Syncytial Virus, Science, Oct. 2013, pp. 592-598, vol. 342, No. 6158.
Magro et al., Neutralizing antibodies against the preactive form of respiratory syncytial virus fusion protein offer unique possibilities for clinical intervention, Proceedings of the National Academy of Sciences, Feb. 21, 2012, pp. 3089-3094, vol. 109, No. 8.
PCT International Search Report, PCT/EP2014/062655, dated Oct. 9, 2014.
PCT International Search Report, dated Aug. 12, 2014, PCT/EP2014/058353.
PCT Written Opinion of International Searching Authority, dated Aug. 12, 2014, PCT/EP2014/058353.
Yin et al., Structure of the parainfluenza virus 5 F protein in its metastable, prefusion conformation, Nature, Jan. 1, 2006, pp. 38-44, vol. 439, No. 7072.
McLellan et al., Structure of RSV Fusion Glycoprotein Bound to a Prefusion-Specific Neutralizing Antibody, Science, Apr. 25, 2013, pp. 1113-1117, vol. 340, No. 6136.
PCT Written Opinion of International Searching Authority, PCT/EP2014/062655, dated Oct. 9, 2014.
Swanson et al., "Structural Basis for Immunization with Postfusion Respiratory Syncytial Virus Fusion F Glycoprotein (RSV F) to Elicit High Neutralizing Antibody Titers," PNAS, vol. 108, pp. 9619-9624 (2011).
"Database UniProt Accession W8CJC7," http://ibis.internal.epo.org/exam/dbfetch.jsp?id=UNIPROT:W8CJC7, Download date: Aug. 12, 2015, 1 page.
Widjaja et al., "Recombinant soluble Respiratory Syncytial Virus F Protein That Lacks Heptad Repeat B, Contains a GCN4 Trimerization Motif and Is Not Cleaved Displays Prefusion-Like Characteristics," PLOS One, 20 pages, Jun. 24, 2015.
Written Opinion dated Oct. 10, 2016 in Int'l Application No. PCT/EP2016/066104.
Int'l Search Report dated Oct. 10, 2016 in Int'l Application No. PCT/EP2016/066104.
Written Opinion dated Oct. 12, 2016 in Int'l Application No. PCT/EP2016/066098.
Int'l Search Report dated Oct. 12, 2016 in Int'l Application No. PCT/EP2016/066098.
Nigwuta et al, "Prefusion F-Specific Antibodies Determine the Magnitude of RSV Neutralizing Activity in Human Sera," Science Translational Medicine, vol. 7, No. 309, pp. 1-9 (2015).
Int'l Search Report and Written Opinion dated Jun. 12, 2017 in Int'l Application No. PCT/EP2017/057962.
Abbink et al, "Comparative Seroprevalence and Immunogenicity of Six Rare Serotype Recombinant Adenovirus Vaccine Vectors from Subgroups B and D," Journal of Virology, vol. 81, No. 9, pp. 4654-4663 (May 2007).
Abrahamsen et al, "Construction of an Adenovirus Type 7a E1A-Vector," Journal of Virology, vol. 71, No. 11, pp. 3946-8951 (Nov. 1997).
Altaras et al, "Production and Formulation of Adenovirus Vectors," Advances in Biochemical Engineering / Biotechnology, vol. 99, pp. 193-260 (2005).
Brough et al, "A Gene Transfer Vector-Cell Line System for Complete Functional Complementation of Adenovirus Early Regions E1 and E4," Journal of Virology, vol. 70, No. 9, pp. 6497-6501 (Sep. 1996).
Fallaux et al, "New Helper Cells and Matched Early Region 1-Deleted Adenovirus Vectors Prevent Generation of Replication-Competent Adenoviruses," Human Gene Therapy, vol. 9, pp. 1909-1917 (Sep. 1998).
Gao et al, "A Cell Line for High-Yield Production of El-Deleted Adenovirus Vectors without the Emergence of Replication-Competent Virus," Human Gene Therapy, vol. 11, pp. 213-219 (Jan. 2000).
Goerke et al, "Development of a Novel Adenovirus Purification Process Utilizing Selective Precipitation of Cellular DNA," Biotechnology and Bioengineering, vol. 91, pp. 12-21 (2005).
Havenga et al, "Novel replication-incompetent adenoviral B-group vectors: high vector stability and yield in PER.C6 cells," Journal of General Virology, vol. 87, pp. 2135-2143 (2006).
Hoganson et al, "Development of a Stable Adenoviral Vector Formulation," BioProcessing Journal, vol. 1, No. 1, pp. 43-48 (Mar. 2002).
Kim et al, "Single mucosal immunization of recombinant adenovirus-based vaccine expressing F1 protein fragment induces protective mucosal immunity against respiratory syncytial virus infection," Vaccine, vol. 28, pp. 3801-3808 (2010).
Kohlmann et al, "Protective Efficacy and Immunology of an Adenoviral Vector Vaccine Encoding the Codon-Optimized F Protein of Respiratory Syncytial Virus," Journal of Virology, vol. 83, No. 23, pp. 12601-12610 (Dec. 2009).
Konz et al, "Serotype Specificity of Adenovirus Purification Using Anion-Exchange Chromatography," Human Gene Therapy, vol. 16, pp. 1346-1353 (Nov. 2005).
Konz et al, "Scaleable Purification of Adenovirus Vectors," Methods in Molecular Biology, vol. 434, No. 2, pp. 13-23 (2008).
Krarup et al, "A Highly Stable Prefusion RSV F Vaccine Derived from Structural Analysis of the Fusion Mechanism," Nature Communications, vol. 6, pp. 1-11 (Sep. 2015).
Van et al, "Development of an Ad7 cosmid system and generation of an Ad7LE1LE3HIVMN env/rev recombinant virus," Gene Therapy, vol. 10, pp. 326-336 (2003).
Pemberton et al, "Cytoxic T Cell Specificity for Respiratory Syncytial Virus Proteins: Fusion Protein is an Important Target Antigen, Journal of General Virology," vol. 68, pp. 2177-2182 (1987).
Solabomi et al, "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, vol. 76, No. 8, pp. 3817-3823 (Aug. 2008).
Vogels et al, "Replication-Deficient Human Adenovirus Type 35 Vectors for Gene Transfer and Vaccination: Efficient Human Cell Infection and Bypass of Preexisting Adenovirus Immunity," Journal of Virology, vol. 77, No. 15, pp. 8263-8271 (Aug. 2003).

(56) References Cited

OTHER PUBLICATIONS

Yu et al, "Single Intranasal Immunization with Recombinant Adenovirus-Based Vaccine Induces Protective Immunity against Respiratory Syncytial Virus Infection," Journal of Virology, vol. 82, No. 5, pp. 2350-2357 (Mar. 2008).
Int'l Search Report and Written Opinion dated Jun. 12, 2017 in Int'l Application No. PCT/EP2017/057957.
Krause et al, "A Broadly Neutralizing Human Monclonal Antibody That Recognizes a Conserved, Novel Epitope on the Globular Head of the Influenza H1N1 Virus Hemagglutinin," Journal of Virology, vol. 85, No. 20, pp. 10905-10908 (Oct. 2011).
McClellan et al, "Structure of Respiratory Syncytial Virus Fusion Glycoprotein in the Postfusion Conformation Reveals Preservation of Neutralizing Epitopes," Journal of Virology, vol. 85, No. 15, pp. 7788-7796 (Aug. 2011).
Database Geneseq (online) "RSV fusion protein N67I S215P, RSV CL57-v224, fibritin, SEQ: 74", XP002761983, retrieved from EBI accession No. GSP:BBP75438, Database accession No. BBP75438 sequence.

Neuzil, "Progress toward a Respiratory Syncytial Virus Vaccine", Clinical and Vaccine Immunology, vol. 23, pp. 186-188, 2016.

* cited by examiner

STABILIZED SOLUBLE PRE-FUSION RSV F POLYPEPTIDES

CROSS-REFERENCE TO RELATED APPLICATIONS

This application is a national phase entry under 35 U.S.C. § 371 of International Patent Application PCT/EP2014/062655, filed Jun. 17, 2014, designating the United States of America and published in English as International Patent Publication WO 2014/202570 A1 on Dec. 24, 2014, which claims the benefit under Article 8 of the Patent Cooperation Treaty to European Patent Application Serial No. 13172256.3, filed Jun. 17, 2013.

STATEMENT ACCORDING TO 37 C.F.R. § 1.821(C) OR (E)—SEQUENCE LISTING SUBMITTED AS A TEXT AND PDF FILE

Pursuant to 37 C.F.R. § 1.821(c) or (e), a file containing a TXT version and a PDF version of the Sequence Listing has been submitted concomitant with this application, the contents of which are hereby incorporated by reference.

TECHNICAL FIELD

This disclosure relates to the field of medicine and biotechnology. The disclosure, in particular, relates to recombinant pre-fusion RSV F polypeptides and uses thereof, e.g., in immunogenic compositions.

BACKGROUND

Respiratory syncytial virus (RSV) is an enveloped non-segmented negative-strand RNA virus in the family Paramyxoviridae, genus *Pneumovirus*. Worldwide, it is estimated that 64 million RSV infections occur each year resulting in 160,000 deaths (WHO Acute Respiratory Infections Update September 2009). The most severe disease occurs particularly in premature infants, the elderly and immune-compromised individuals. In children younger than 2 years, RSV is the most common respiratory tract pathogen, accounting for approximately 50% of the hospitalizations due to respiratory infections, with a peak of hospitalization occurring at 2-4 months of age. It has been reported that almost all children have been infected by RSV by the age of two. Repeated infection during lifetime is attributed to ineffective natural immunity. The level of RSV disease burden, mortality and morbidity in the elderly are second only to those caused by non-pandemic influenza A infections.

Figure 3A:
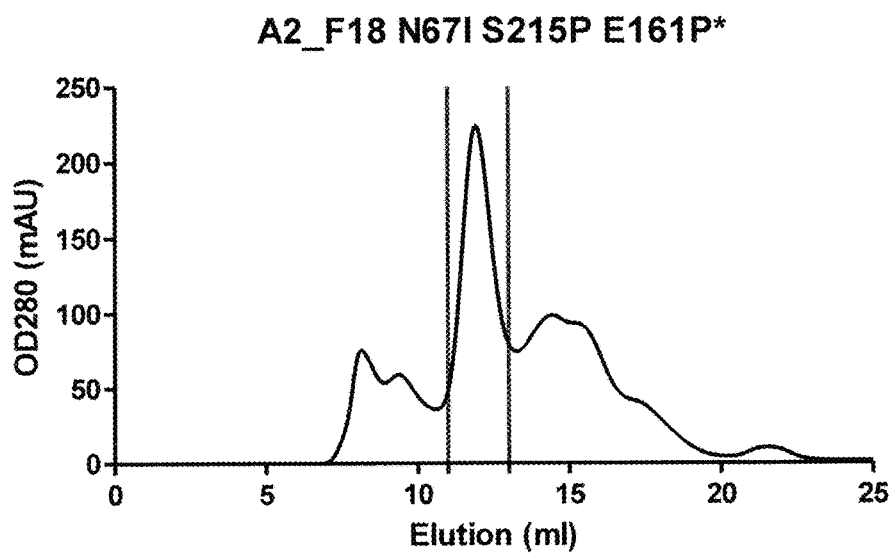
Figure 3B:
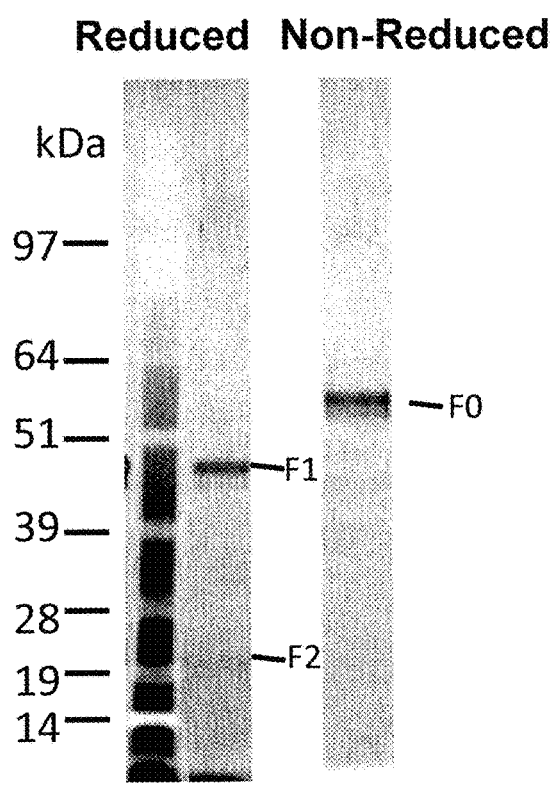
Figure 3C:

To infect a host cell, RSV, like other enveloped viruses such as influenza virus and HIV, require fusion of the viral membrane with a host cell membrane. For RSV, the conserved fusion protein (RSV F protein) fuses the viral and host cell cellular membranes. In current models, based on paramyxovirus studies, the RSV F protein initially folds into a "pre-fusion" conformation. The metastable structure has recently been solved in complex with a stabilizing neutralizing antibody Fab fragment (McLellan et al., *Science* 340(6136):1113-7, 2013). During cell entry, the pre-fusion conformation undergoes refolding and conformational changes to its "post-fusion" conformation (McLellan, *J. Vivol.* 85(15):7788-96, 2010*; Swanson, PNAS* 108(23): 9619-24, 2011). Thus, the RSV F protein is a metastable protein that drives membrane fusion by coupling irreversible protein refolding to membrane juxtaposition by initially folding into a metastable form (pre-fusion conformation) that subsequently undergoes discrete/stepwise conformational changes to a lower energy conformation (post-fusion conformation).

These observations suggest that pre-fusion and post-fusion RSV F protein are antigenically distinct (L. J. Calder et al., *Virology* 271:122-131 (2000)).

A vaccine against RSV infection is not currently available, but is desired. Vaccine candidates based on the RSV F protein have failed due to problems with, e.g., stability, purity, reproducibility, and potency. As indicated above, crystal structures have revealed a large conformational change between the pre-fusion and post-fusion states. The magnitude of the rearrangement suggested that only a portion of antibodies directed to the post-fusion conformation of RSV F will be able to cross react with the native conformation of the pre-fusion spike on the surface of the virus. Accordingly, efforts to produce a vaccine against RSV have focused on developing vaccines that contain pre-fusion forms of RSV F protein (see, e.g., WO 2010/149745, WO 2010/149743, WO 2009/079796, and WO 2012/158613). However, these efforts have not yet yielded stable pre-fusion RSV F polypeptides that could be used as candidates for testing in humans.

BRIEF SUMMARY

Provided are stable, recombinant, pre-fusion respiratory syncytial virus (RSV) fusion (F) polypeptides, i.e., recombinant RSV F polypeptides that are stabilized in the pre-fusion conformation. The RSV F polypeptides of the disclosure comprise at least one epitope that is specific to the pre-fusion conformation F protein. In certain embodiments, the pre-fusion RSV F polypeptides are soluble. The disclosure also provides nucleic acid molecules encoding the pre-fusion RSV F polypeptides according to the disclosure and vectors comprising such nucleic acid molecules.

The disclosure also relates to compositions, preferably immunogenic compositions, comprising a RSV F polypeptide, a nucleic acid molecule and/or a vector, and to the use thereof in inducing an immune response against RSV F protein, in particular, use thereof as a vaccine. The disclosure also relates to methods for inducing an anti-respiratory syncytial virus (RSV) immune response in a subject, comprising administering to the subject an effective amount of a pre-fusion RSV F polypeptide, a nucleic acid molecule encoding the RSV F polypeptide, and/or a vector comprising the nucleic acid molecule. Preferably, the induced immune response is characterized by neutralizing antibodies to RSV and/or protective immunity against RSV. In particular aspects, the disclosure relates to a method for inducing neutralizing anti-respiratory syncytial virus (RSV) F protein antibodies in a subject, comprising administering to the subject an effective amount of an immunogenic composition comprising a pre-fusion RSV F polypeptide, a nucleic acid molecule encoding the RSV F polypeptide, and/or a vector comprising the nucleic acid molecule.

BRIEF DESCRIPTION OF THE FIGURES

FIG. 1: Reduced and non-reduced SDS-PAGE with RSV pre-Fusion DM=Double mutant (N67I+S215P=SEQ ID NO:21) and DM+CC=Double mutant+DE486CC=SEQ ID NO:94).

FIG. 2: NativePAGE analysis of supernatants from Lane 2: DM=Double mutant (N67I+S215P=SEQ ID NO:21) and Lane 1: DM+CC=Double mutant+DE486CC=SEQ ID NO:94).

FIGS. 3A-3C: FIG. 3A, SUPERDEX® 200 gel filtration chromatogram of the eluate PreF N67I E161P S215P, RSV A2, fibritin (SEQ ID NO:91) from the ion-exchange column. FIG. 3B, SDS-PAGE analysis of the pre-fusion F protein containing peak from the SEC chromatogram under reducing conditions. FIG. 3C, NativePAGE analysis of purified RSV pre-fusion F protein (SEQ ID NO:91, Lane 2) compared to purified RSV pre-fusion F double mutant (SEQ ID NO:21, Lane 1).

Figure 4:
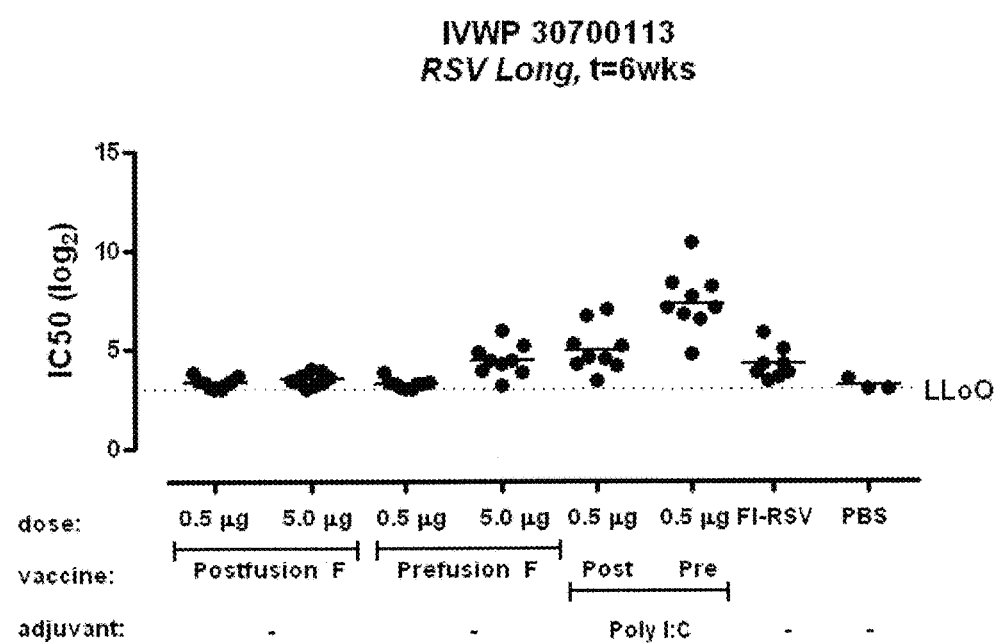

FIG. 4: VNA titers of mice at week 6 after a prime boost at weeks 0 and 4 with immunogens and doses according to Table 14.

Figure 5:
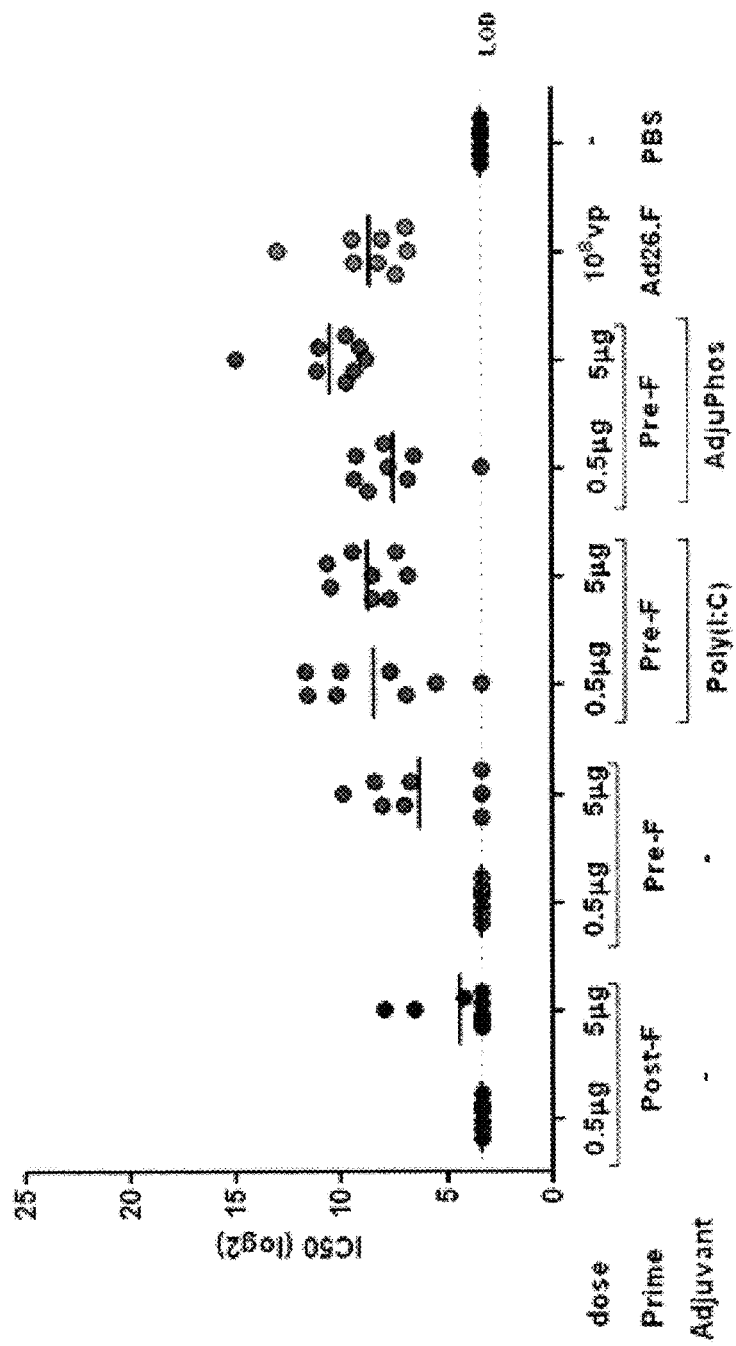

FIG. 5: VNA titers of cotton rats at week 7 after a prime boost at weeks 0 and 4 with immunogens and doses according to Table 15.

Figure 6:
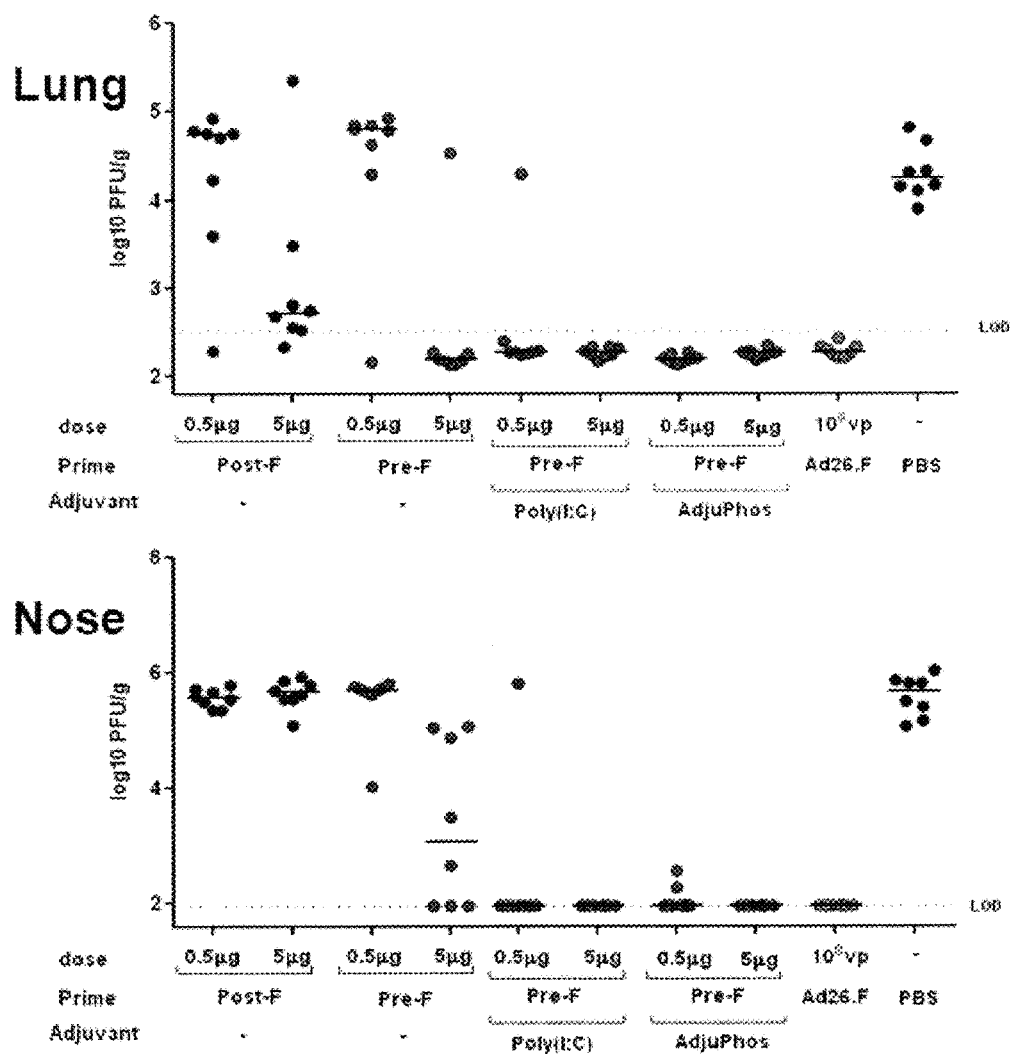

FIG. 6: Lung and nose viral load at 5 days after i.n. RSV challenge.

DETAILED DESCRIPTION

The fusion protein (F) of the respiratory syncytial virus (RSV) is involved in fusion of the viral membrane with a host cell membrane, which is required for infection. The RSV F mRNA is translated into a 574-amino acid precursor protein designated F0, which contains a signal peptide sequence at the N-terminus (e.g., amino acid residues 1-26 of SEQ ID NO:1) that is removed by a signal peptidase in the endoplasmic reticulum. F0 is cleaved at two sites (between amino acid residues 109/110 and 136/137) by cellular proteases (in particular, furin, or furin-like)) removing a short glycosylated intervening sequence (also referred to as a p27 region, comprising the amino acid residues 110 to 136, and generating two domains or subunits designated F1 and F2. The F1 domain (amino acid residues 137-574) contains a hydrophobic fusion peptide at its N-terminus and the C-terminus contains the transmembrane (TM) (amino acid residues 530-550) and cytoplasmic region (amino acid residues 551-574). The F2 domain (amino acid residues 27-109) is covalently linked to F1 by two disulfide bridges. The F1-F2 heterodimers are assembled as homotrimers in the virion.

A vaccine against RSV infection is not currently available, but is desired. One potential approach to producing a vaccine is a subunit vaccine based on purified RSV F protein. However, for this approach, it is desirable that the purified RSV F protein is in a conformation that resembles the conformation of the pre-fusion state of RSV F protein, that is stable over time, and can be produced in sufficient quantities. In addition, for a subunit-based vaccine, the RSV F protein needs to be truncated by deletion of the transmembrane (TM) and the cytoplasmic region to create a soluble secreted F protein (sF). Because the TM region is responsible for membrane anchoring and trimerization, the anchorless soluble F protein is considerably more labile than the full-length protein and will readily refold into the post-fusion end-state. In order to obtain soluble F protein in the stable pre-fusion conformation that shows high expression levels and high stability, the pre-fusion conformation thus needs to be stabilized.

Stabilization of another paramyxovirus F protein in the pre-fusion conformation has been successfully accomplished for parainfluenza type 5 (PIV5). Yin et al. (Nature 439:38-44 (2006)) thus stabilized the pre-fusion structure of PIV-5 F protein by mutation of the furin cleavage site in $F_0$, which blocked processing into F1 and F2. Furthermore, the transmembrane (TM) and cytoplasmic domain were replaced by a well-known helical trimerization domain: GCN4pII. This domain forms a trimeric helical coiled coil structure and is a modification of the natural dimeric helical coiled coil peptide GCN4 (O'Shea et al., Science 243:538-542 (1989)). The GCN4-pII peptide, in which the amino acid sequence of the GCN4 Leucine zipper was substituted with Isoleucine residues at every a and d position of the heptad, was shown to form a triple-stranded parallel alpha-helical coiled coil (Harbury et al., Science 262:1401-1407 (1993)).

For the stabilization of RSV F in the pre-fusion conformation, the same strategy has been tried, i.e., mutation of the furin cleavage site and fusion of the RSV F ectodomain to a GCN4pII trimerization domain (as disclosed in e.g., WO 2010/149743, WO 2010/149745, WO 2009/079796, and WO 2012/158613) or to the fibritin trimerization domain (McLellan et al., Nature Struct. Biol. 17:2-248-250 (2010); McLellan et al., Science 340(6136):1113-7 (2013)). This fibritin domain or "foldon" is derived from T4 fibritin and was described earlier as an artificial natural trimerization domain (Letarov et al., Biochemistry Moscow 64:817-823 (1993); S-Guthe et al., J. Mol. Biol. 337:905-915 (2004)). However, these efforts have not resulted in stable pre-fusion RSV F protein. Moreover, these efforts have not yet resulted in candidates suitable for testing in humans.

Now provided are recombinant stable pre-fusion RSV F polypeptides, i.e., RSV F polypeptides that are stabilized in the pre-fusion conformation. In the research that led to this disclosure, several modification steps were introduced and/or combined in order to obtain the stable soluble pre-fusion RSV F polypeptides. The stable pre-fusion RSV F polypeptides of the disclosure are in the pre-fusion conformation, i.e., they comprise (display) at least one epitope that is specific to the pre-fusion conformation F protein. An epitope that is specific to the pre-fusion conformation F protein is an epitope that is not presented in the post-fusion conformation. Without wishing to be bound by any particular theory, it is believed that the pre-fusion conformation of RSV F protein may contain epitopes that are the same as those on the RSV F protein expressed on natural RSV virions and, therefore, may provide advantages for eliciting protective neutralizing antibodies.

The polypeptides of the disclosure comprise at least one epitope that is recognized by a pre-fusion specific monoclonal antibody, comprising a heavy chain CDR1 region of SEQ ID NO:54, a heavy chain CDR2 region of SEQ ID NO:55, a heavy chain CDR3 region of SEQ ID NO:56 and a light chain CDR1 region of SEQ ID NO:62, a light chain CDR2 region of SEQ ID NO:63, and a light chain CDR3 region of SEQ ID NO:64 (hereafter referred to as "CR9501") and/or a pre-fusion specific monoclonal antibody comprising a heavy chain CDR1 region of SEQ ID NO:58, a heavy chain CDR2 region of SEQ ID NO:59, a heavy chain CDR3 region of SEQ ID NO:60 and a light chain CDR1 region of SEQ ID NO:66, a light chain CDR2 region of SEQ ID NO:67, and a light chain CDR3 region of SEQ ID NO:68 (referred to as "CR9502"). CR9501 and CR9502 comprise the heavy and light chain variable regions and, thus, the binding specificities of the antibodies 58C5 and 30D8, respectively, which have previously been shown to bind specifically to RSV F protein in its pre-fusion conformation and not to the post-fusion conformation (see WO 2012/006596).

In certain embodiments, the recombinant pre-fusion RSV F polypeptides comprise at least one epitope that is recognized by at least one pre-fusion-specific monoclonal antibody as described above and are trimeric.

The stable pre-fusion RSV F polypeptides according to the disclosure comprise an F1 domain and an F2 domain, wherein the polypeptides comprise at least one mutation, as compared to wild-type F1 and F2 domains, selected from the group consisting of:
(a) a mutation of the amino acid residue at position 161;
(b) a mutation of the amino acid residue at position 182;
(c) a mutation of the amino acid residue at position 173; and
(d) a mutation of the amino acid residue D at position 486 into C (D486C) in combination with a mutation of the amino acid residue D at position 489 into C (D489C) or a mutation of the amino acid residue E at position 487 into C (E487C).

In certain embodiments, the stable pre-fusion RSV F polypeptides comprise an F1 domain and an F2 domain, wherein the polypeptides comprise at least one mutation selected from the group consisting of:
(a) a mutation of the amino acid residue E at position 161 into P, Q or G (E161P, E161Q) or E161G);
(b) a mutation of the amino acid residue S at position 182 into P (S182P);
(c) a mutation of the amino acid residue S, T or N at position 173 into P (S173P); and
(d) a mutation of the amino acid residue D at position 486 into C (D486C) in combination with a mutation of the amino acid residue D at position 489 into C (D489C) or a mutation of the amino acid residue E at position 487 into C (E487C).

In certain embodiments, the pre-fusion RSV F polypeptides further comprise a mutation of the amino acid residue at position 67 and/or a mutation of the amino acid residue at position 215.

In certain embodiments, the stable pre-fusion RSV F polypeptides thus comprise an F1 domain and an F2 domain, wherein the polypeptides comprise a mutation of the amino acid residue at position 67 and/or a mutation of the amino acid residue at position 215, and at least one further mutation selected from the group consisting of:
(a) a mutation of the amino acid residue at position 161;
(b) a mutation of the amino acid residue at position 182;
(c) a mutation of the amino acid residue at position 173; and
(d) a mutation of the amino acid residue D at position 486 into C (D486C) in combination with a mutation of the amino acid residue D at position 489 into C (D489C) or a mutation of the amino acid residue E at position 487 into C (E487C).

In certain embodiments, the stable pre-fusion RSV F polypeptides comprise an F1 domain and an F2 domain, wherein the polypeptides comprise a mutation of the amino acid residue N or T at position 67 and/or a mutation of amino acid residue S at position 215, and wherein the polypeptides further comprise at least one further mutation selected from the group consisting of:
(a) a mutation of the amino acid residue E at position 161 into P, Q or G (E161P, E161Q) or E161G);
(b) a mutation of the amino acid residue S at position 182 into P (S182P);
(c) a mutation of the amino acid residue S, T or N at position 173 into P (S173P); and
(d) a mutation of the amino acid residue D at position 486 into C (D486C) in combination with a mutation of the amino acid residue D at position 489 into C (D489C) or a mutation of the amino acid residue E at position 487 into C (E487C).

In certain embodiments, the stable pre-fusion RSV F polypeptides comprise a linking sequence comprising from 1 to 10 amino acids, linking the F1 domain and F2 domain.

In certain embodiments, the stable pre-fusion RSV F polypeptides according to the disclosure thus comprise an F1 domain and an F2 domain, and a linking sequence comprising from 1 to 10 amino acid residues, linking the F1 domain to the F2 domain, wherein the polypeptides comprise at least one mutation selected from the group consisting of:
(a) a mutation of the amino acid residue E at position 161 into P, Q or G (E161P, E161Q) or E161G);
(b) a mutation of the amino acid residue S at position 182 into P (S182P);
(c) a mutation of the amino acid residue S, T or N at position 173 into P (S173P); and
(d) a mutation of the amino acid residue D at position 486 into C (D486C) in combination with a mutation of the amino acid residue D at position 489 into C (D489C) or a mutation of the amino acid residue E at position 487 into C (E487C).

In certain embodiments, the stable pre-fusion RSV F polypeptides further comprise a mutation of the amino acid residue N or T at position 67 and/or a mutation of amino acid residue S at position 215. In certain embodiments, the stable pre-fusion RSV F polypeptides further comprise a mutation of the amino acid residue N or T at position 67 (N/T67I) into I and/or a mutation of amino acid residue S at position 215 into P (S215P).

In certain embodiments, the stable pre-fusion RSV F polypeptides according to the disclosure comprise a truncated F1 domain.

In certain embodiments, the stable pre-fusion RSV F polypeptides according to the disclosure thus comprise a truncated F1 domain and an F2 domain and, optionally, a linking sequence comprising from 1 to 10 amino acid residues, linking the truncated F1 domain to the F2 domain, wherein the polypeptides comprise at least one further mutation selected from the group consisting of:
(a) a mutation of the amino acid residue E at position 161 into P, Q or G (E161P, E161Q) or E161G);
(b) a mutation of the amino acid residue S at position 182 into P (S182P);
(c) a mutation of the amino acid residue S, T or N at position 173 into P (S173P); and
(d) a mutation of the amino acid residue D at position 486 into C (D486C) in combination with a mutation of the amino acid residue D at position 489 into C (D489C) or a mutation of the amino acid residue E at position 487 into C (E487C).

In certain embodiments, the polypeptides further comprise a mutation of the amino acid residue N or T at position 67 and/or a mutation of amino acid residue S at position 215. In certain embodiments, the stable pre-fusion RSV F polypeptides further comprise a mutation of the amino acid residue N or T at position 67 (N/T67I) into I and/or a mutation of amino acid residue S at position 215 into P (S215P).

According to the disclosure, the polypeptides of the disclosure thus comprise at least one stabilizing mutation in the F1 and/or F2 domain as compared to the RSV F1 and/or F2 domain in a wild-type RSV F protein. It is known that RSV exists as a single serotype having two antigenic subgroups: A and B. The amino acid sequences of the mature processed F proteins of the two groups are about 93% identical. As used throughout this disclosure, the amino acid positions are given in reference to the sequence of RSV F protein from the A2 strain (SEQ ID NO:1). As used in this disclosure, the wording "the amino acid at position "x" of the RSV F protein" thus means the amino acid corresponding to the amino acid at position "x" in the RSV F protein of the RSV A2 strain of SEQ ID NO:1. Note that, in the numbering system used throughout this disclosure, "1" refers to the N-terminal amino acid of an immature F0 protein (SEQ ID NO:1). When an RSV strain other than the A2 strain is used, the amino acid positions of the F protein are to be numbered with reference to the numbering of the F protein of the A2 strain of SEQ ID NO:1 by aligning the sequences of the other RSV strain with the F protein of SEQ ID NO:1 with the insertion of gaps as needed. Sequence alignments can be done using methods well known in the art, e.g., by CLUSTALW, Bioedit or CLC Workbench.

An amino acid according to the disclosure can be any of the twenty naturally occurring (or "standard") amino acids or variants thereof, such as, e.g., D-amino acids (the D-enantiomers of amino acids with a chiral center), or any variants that are not naturally found in proteins, such as, e.g., norleucine. The standard amino acids can be divided into several groups based on their properties. Important factors are charge, hydrophilicity or hydrophobicity, size and functional groups. These properties are important for protein structure and protein-protein interactions. Some amino acids have special properties, such as cysteine, that can form covalent disulfide bonds (or disulfide bridges) to other cysteine residues, proline that induces turns of the polypeptide backbone, and glycine that is more flexible than other amino acids. Table 17 shows the abbreviations and properties of the standard amino acids.

It will be appreciated by a skilled person that the mutations can be made to the protein by routine molecular biology procedures. The mutations according to the disclosure preferably result in increased expression levels and/or increased stabilization of the pre-fusion RSV F polypeptides as compared to RSV F polypeptides that do not comprise these mutation(s).

In certain embodiments, the pre-fusion RSV F polypeptides are full length.

In certain embodiments, the pre-fusion RSV F polypeptides are soluble.

In certain embodiments, the pre-fusion RSV F polypeptides further comprise a heterologous trimerization domain linked to the truncated F1 domain. According to the disclosure, it was shown that by linking a heterologous trimerization domain to the C-terminal amino acid residue of a truncated F1 domain, optionally combined with a linking sequence linking the F1 and F2 domains and the stabilizing mutation(s), RSV F polypeptides are provided that show high expression and that bind to pre-fusion-specific antibodies, indicating that the polypeptides are in the pre-fusion conformation. In addition, the RSV F polypeptides are stabilized in the pre-fusion conformation, i.e., even after processing of the polypeptides, they still bind to the pre-fusion-specific antibodies CR9501 and/or CR9502, indicating that the pre-fusion-specific epitope is retained.

In further embodiments, the pre-fusion RSV F polypeptides comprise one or more further mutations (as compared to the wild-type RSV F protein), selected from the group consisting of:
  (a) a mutation of the amino acid residue at position 46;
  (b) a mutation of the amino acid residue at position 77;
  (c) a mutation of the amino acid residue at position 80;
  (d) a mutation of the amino acid residue at position 92;
  (e) a mutation of the amino acid residue at position 184;
  (f) a mutation of the amino acid residue at position 185;
  (g) a mutation of the amino acid residue at position 201;
  (h) a mutation of the amino acid residue at position 209;
  (i) a mutation of the amino acid residue at position 421;
  (j) a mutation of the amino acid residue at position 426;
  (k) a mutation of the amino acid residue at position 465;
  (l) a mutation of the amino acid residue at position 486;
  (m) a mutation of the amino acid residue at position 487; and
  (n) a mutation of the amino acid residue at position 508.

In preferred embodiments, the one or more further mutations are selected from the group consisting of:
  (a) a mutation of the amino acid residue S at position 46 into G (S46G);
  (b) a mutation of the amino acid residue K at position 77 into E (K77E);
  (c) a mutation of the amino acid residue K at position 80 into E (K80E);
  (d) a mutation of the amino acid residue E at position 92 into D (E92D);
  (e) a mutation of the amino acid residue G at position 184 into N (G184N);
  (f) a mutation of the amino acid residue V at position 185 into N (V185N);
  (g) a mutation of the amino acid residue K at position 201 into Q (K201Q);
  (h) a mutation of the amino acid residue K at position 209 into Q (K209Q);
  (i) a mutation of the amino acid residue K at position 421 into N (K421N);
  (j) a mutation of the amino acid residue N at position 426 into S (N426S);
  (k) a mutation of the amino acid residue K at position 465 into E or Q (K465Q);
  (l) a mutation of the amino acid residue D at position 486 into N (D486N);
  (m) a mutation of the amino acid residue E at position 487 into Q, N or I (E487Q/N/I); and
  (n) a mutation of the amino acid residue K at position 508 into E (K508E).

As described above, in certain embodiments, the pre-fusion RSV F polypeptides comprise a mutation of the amino acid residue D at position 486 into C (D486C) in combination with D489C or E487C. These double mutations to two extra cysteine residues result in an inter-subunit disulfide bridge between the F1 proteins to establish a covalent bond between the protomers and to stabilize the pre-fusion RSV F structure.

It is again noted that for the positions of the amino acid residues, reference is made to SEQ ID NO:1. A skilled person will be able to determine the corresponding amino acid residues in F proteins of other RSV strains.

In certain embodiments, the pre-fusion RSV F polypeptides comprise at least two mutations (as compared to a wild-type RSV F protein).

In certain embodiments, the polypeptides comprise at least three mutations.

In certain embodiments, the polypeptides comprise at least four, five or six mutations.

In certain embodiments, the heterologous trimerization domain comprises the amino acid sequence EKKIEAIEKKIEAIEKKIEA (SEQ ID NO:3). In certain other embodiments, the heterologous trimerization domain comprises the amino acid sequence GYIPEAPRDGQAYVRKDGEWVLLSTFL (SEQ ID NO:4).

As described above, in certain embodiments, the polypeptides of the disclosure comprise a truncated F1 domain. As used herein, a "truncated" F1 domain refers to an F1 domain that is not a full-length F1 domain, i.e., wherein either N-terminally or C-terminally, one or more amino acid residues have been deleted. According to the disclosure, at least the transmembrane domain and cytoplasmic tail have been deleted to permit expression as a soluble ectodomain.

In certain other embodiments, the F1 domain is truncated after amino acid residue 495 of the RSV F protein (referring to SEQ ID NO:1), i.e., the C-terminal part of the F1 domain starting from amino acid residue 496 (referring to SEQ ID NO:1) has been deleted. In certain other embodiments, the F1 domain is truncated after amino acid residue 513 of the RSV F protein. In certain embodiments, the F1 domain is truncated after amino acid residue 486, 487, 488, 489, 490, 491, 492, 493, 494, 495, 496, 497, 498, 499, 500, 501, 502, 503, 504, 505, 506, 507, 508, 509, 510, 512, 513, 514, 515, 516, 517, 518, 519, 520, 521, 522, 523, 524 or 525.

In certain embodiments, the trimerization domain is linked to amino acid residue 495 of the RSV F1 domain. In certain embodiments, the trimerization domain comprises SEQ ID NO:4 and is linked to amino acid residue 495 of the RSV F1 domain.

In certain other embodiments, the trimerization domain is linked to amino acid residue 513 of the RSV F1 domain. In certain embodiments, the trimerization domain comprises SEQ ID NO:3 and is linked to amino acid residue 513 of the RSV F1 domain.

As described above, in certain embodiments, the F1 domain, which is optionally truncated, and the F2 domain are linked by a linking sequence, linking the C-terminal amino acid of the F2 domain to the N-terminal amino acid of the (optionally truncated) F2 domain. In certain embodiments, the linking sequence (or linker) comprises from 1-10 amino acid residues, preferably from 2-9 amino acid residues, preferably from 3-8 amino acid residues, preferably from 4-7 amino acid residues, and more preferably, the linker comprises 5 or 6 amino acid residues. Numerous conformationally neutral linkers are known in the art that can be used according to the disclosure without disrupting the conformation of the pre-fusion RSV F polypeptides. In preferred embodiments, the linker comprises the amino acid sequence GSGSG (SEQ ID NO:5).

In certain embodiments, the F1 domain and/or the F domain are from an RSV A strain. In certain embodiments, the F1 and/or F2 domain are from the RSV A2 strain of SEQ ID NO:1.

In certain embodiments, the F1 and/or F2 domain are from the RSV A2 strain of SEQ ID NO:69.

In certain embodiments, the F1 domain and/or the F domain are from an RSV B strain. In certain embodiments, the F1 and/or F2 domain are from the RSV B strain of SEQ ID NO:2.

In certain embodiments, the F1 and F2 domains are from the same RSV strain. In certain embodiments, the pre-fusion RSV F polypeptides are chimeric polypeptides, i.e., comprising F1 and F2 domains that are from different RSV strains.

In certain embodiments, the level of expression of the pre-fusion RSV F polypeptides of the disclosure is increased, as compared to a full-length wild-type RSV F polypeptide or a wild-type ectodomain (i.e., without the transmembrane and cytoplasmic region) without the mutation(s). In certain embodiments, the level of expression is increased at least five-fold, preferably up to ten-fold. In certain embodiments, the level of expression is increased more than ten-fold.

The pre-fusion RSV F polypeptides according to the disclosure are stable, i.e., do not readily change into the post-fusion conformation upon processing of the polypeptides, such as, e.g., purification, freeze-thaw cycles, and/or storage, etc.

In certain embodiments, the pre-fusion RSV F polypeptides according to the disclosure have an increased stability upon storage at 4° C. as compared to an RSV F polypeptide without the mutation(s). In certain embodiments, the polypeptides are stable upon storage at 4° C. for at least 30 days, preferably at least 60 days, preferably at least 6 months, even more preferably at least 1 year. With "stable upon storage," it is meant that the polypeptides still display the at least one epitope specific for the pre-fusion-specific antibody (e.g., CR9501) upon storage of the polypeptide in solution (e.g., culture medium) at 4° C. for at least 30 days, e.g., as determined using a method as described in Example 8 or 10. In certain embodiments, the polypeptides display the at least one pre-fusion-specific epitope for at least 6 months, preferably for at least 1 year upon storage of the pre-fusion RSV F polypeptides at 4° C.

In certain embodiments, the pre-fusion RSV F polypeptides according to the disclosure have an increased stability when subjected to heat, as compared to RSV F polypeptides without the mutation(s). In certain embodiments, the pre-fusion RSV F polypeptides are heat stable for at least 30 minutes at a temperature of 55° C., preferably at 58° C., more preferably at 60° C. With "heat stable" it is meant that the polypeptides still display the at least one pre-fusion-specific epitope after having been subjected for at least 30 minutes to an increased temperature (i.e., a temperature of 55° C. or above), e.g., as determined using a method as described in Example 9.

In certain embodiments, the polypeptides display the at least one pre-fusion-specific epitope after being subjected to 1 to 6 freeze-thaw cycles in an appropriate formulation buffer.

In certain preferred embodiments, the pre-fusion RSV F polypeptide of the disclosure comprises an amino acid sequence selected from the group consisting of SEQ ID NOS:90-94. In certain embodiments, the pre-fusion RSV F polypeptide of the disclosure consists of an amino acid sequence selected from the group consisting of SEQ ID NOS:90-94.

As used throughout this disclosure, nucleotide sequences are provided from 5' to 3' direction, and amino acid sequences from N-terminus to C-terminus, as customary in the art.

In certain embodiments, the encoded polypeptides according to the disclosure further comprise a leader sequence, also referred to as "signal sequence" or "signal peptide," corresponding to amino acids 1-26 of SEQ ID NO:1, SEQ ID NO:2 or SEQ ID NO:69. This is a short (typically 5-30 amino acids long) peptide present at the N-terminus of the majority of newly synthesized proteins that are destined toward the secretory pathway. In certain embodiments, the polypeptides according to the disclosure do not comprise a leader sequence.

In certain embodiments, the polypeptides comprise a HIS-Tag. A His-Tag or polyhistidine-tag is an amino acid motif in proteins that consists of at least five histidine (H) residues, often at the N- or C-terminus of the protein, which is generally used for purification purposes.

In certain embodiments, the polypeptides do not comprise a HIS-Tag. According to the disclosure, it has surprisingly been shown that when the HIS-tag is deleted, the level of expression and the stability are increased as compared to polypeptides with a HIS-tag.

This disclosure further provides nucleic acid molecules encoding the RSV F polypeptides according to the disclosure.

In preferred embodiments, the nucleic acid molecules encoding the polypeptides according to the disclosure are codon-optimized for expression in mammalian cells, preferably human cells. Methods of codon-optimization are known and have been described previously (e.g., WO 96/09378). A sequence is considered codon-optimized if at least one non-preferred codon as compared to a wild-type sequence is replaced by a codon that is more preferred. Herein, a non-preferred codon is a codon that is used less frequently in an organism than another codon coding for the same amino acid, and a codon that is more preferred is a codon that is used more frequently in an organism than a non-preferred codon. The frequency of codon usage for a specific organism can be found in codon frequency tables, such as. Preferably, more than one non-preferred codon, preferably most or all non-preferred codons, are replaced by codons that are more preferred. Preferably, the most frequently used codons in an organism are used in a codon-optimized sequence. Replacement by preferred codons generally leads to higher expression.

It will be understood by a skilled person that numerous different polynucleotides and nucleic acid molecules can encode the same polypeptide as a result of the degeneracy of the genetic code. It is also understood that skilled persons may, using routine techniques, make nucleotide substitutions that do not affect the polypeptide sequence encoded by the nucleic acid molecules to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may or may not include introns.

Nucleic acid sequences can be cloned using routine molecular biology techniques, or generated de novo by DNA synthesis, which can be performed using routine procedures by service companies having business in the field of DNA synthesis and/or molecular cloning (e.g., GENEART®, GENSCRIPTS®, INVITROGEN®, and EUROFINS®).

The disclosure also provides vectors comprising a nucleic acid molecule as described above. In certain embodiments, a nucleic acid molecule according to the disclosure is thus part of a vector. Such vectors can easily be manipulated by methods well known to the person skilled in the art and can, for instance, be designed for being capable of replication in prokaryotic and/or eukaryotic cells. In addition, many vectors can be used for transformation of eukaryotic cells and will integrate in whole or in part into the genome of such cells, resulting in stable host cells comprising the desired nucleic acid in their genome. The vector used can be any vector that is suitable for cloning DNA and that can be used for transcription of a nucleic acid of interest. Suitable vectors according to the disclosure are, e.g., adenovectors, such as, e.g., Ad26 or Ad35, alphavirus, paramyxovirus, vaccinia virus, herpes virus, retroviral vectors, etc. The person skilled in the art is capable of choosing suitable expression vectors and inserting the nucleic acid sequences of the disclosure in a functional manner.

Host cells comprising the nucleic acid molecules encoding the pre-fusion RSV F polypeptides also form part of the disclosure. The pre-fusion RSV F polypeptides may be produced through recombinant DNA technology involving expression of the molecules in host cells, e.g., Chinese hamster ovary (CHO) cells, tumor cell lines, BHK cells, human cell lines such as HEK293 cells, PER.C6® cells, or yeast, fungi, insect cells, and the like, or transgenic animals or plants. In certain embodiments, the cells are from a multicellular organism. In certain embodiments, they are of vertebrate or invertebrate origin. In certain embodiments, the cells are mammalian cells. In certain embodiments, the cells are human cells. In general, the production of recombinant proteins, such as the pre-fusion RSV F polypeptides of the disclosure, in a host cell comprises the introduction of a heterologous nucleic acid molecule encoding the polypeptide in expressible format into the host cell, culturing the cells under conditions conducive to expression of the nucleic acid molecule and allowing expression of the polypeptide in the cell. The nucleic acid molecule encoding a protein in expressible format may be in the form of an expression cassette, and usually requires sequences capable of bringing about expression of the nucleic acid, such as enhancer(s), promoter, polyadenylation signal, and the like. The person skilled in the art is aware that various promoters can be used to obtain expression of a gene in host cells. Promoters can be constitutive or regulated, and can be obtained from various sources, including viruses, prokaryotic, or eukaryotic sources, or artificially designed.

Cell culture media are available from various vendors, and a suitable medium can be routinely chosen for a host cell to express the protein of interest, here, the pre-fusion RSV F polypeptides. The suitable medium may or may not contain serum.

A "heterologous nucleic acid molecule" (also referred to herein as "transgene") is a nucleic acid molecule that is not naturally present in the host cell. It is introduced into, for instance, a vector by standard molecular biology techniques. A transgene is generally operably linked to expression control sequences. This can, for instance, be done by placing the nucleic acid encoding the transgene(s) under the control of a promoter. Further regulatory sequences may be added. Many promoters can be used for expression of a transgene(s), and are known to the skilled person, e.g., these may comprise viral, mammalian, synthetic promoters, and the like. A non-limiting example of a suitable promoter for obtaining expression in eukaryotic cells is a CMV-promoter (U.S. Pat. No. 5,385,839), e.g., the CMV immediate early promoter, for instance, comprising nt. −735 to +95 from the CMV immediate early gene enhancer/promoter. A polyadenylation signal, for example, the bovine growth hormone polyA signal (U.S. Pat. No. 5,122,458), may be present behind the transgene(s). Alternatively, several widely used expression vectors are available in the art and from commercial sources, e.g., the pcDNA and pEF vector series of Invitrogen, pMSCV and pTK-Hyg from BD Sciences, pCMV-Script from Stratagene, etc., which can be used to recombinantly express the protein of interest, or to obtain suitable promoters and/or transcription terminator sequences, polyA sequences, and the like.

The cell culture can be any type of cell culture, including adherent cell culture, e.g., cells attached to the surface of a culture vessel or to microcarriers, as well as suspension culture. Most large-scale suspension cultures are operated as batch or fed-batch processes because they are the most straightforward to operate and scale up. Nowadays, continuous processes based on perfusion principles are becoming more common and are also suitable. Suitable culture media are also well known to the skilled person and can generally be obtained from commercial sources in large quantities, or custom-made according to standard protocols. Culturing can be done, for instance, in dishes, roller bottles or in bioreactors, using batch, fed-batch, continuous systems, and the like. Suitable conditions for culturing cells are known (see, e.g., *Tissue Culture*, Academic Press, Kruse and Paterson, editors (1973), and R. I. Freshney, *Culture of animal cells: A manual of basic technique*, fourth edition (Wiley-Liss Inc., 2000, ISBN 0-471-34889-9)).

Further provided are compositions comprising a pre-fusion RSV F polypeptide and/or a nucleic acid molecule, and/or a vector, as described above. Thus provided are compositions comprising a pre-fusion RSV F polypeptide that displays an epitope that is present in a pre-fusion conformation of the RSV F protein but is absent in the post-fusion conformation. Also provided are compositions comprising a nucleic acid molecule and/or a vector, encoding such pre-fusion RSV F polypeptide. Further provided are immunogenic compositions comprising a pre-fusion RSV F polypeptide, and/or a nucleic acid molecule, and/or a vector, as described above. The disclosure also provides the use of a stabilized pre-fusion RSV F polypeptide, a nucleic acid molecule, and/or a vector, according to the disclosure, for inducing an immune response against RSV F protein in a subject. Further provided are methods for inducing an immune response against RSV F protein in a subject, comprising administering to the subject a pre-fusion RSV F polypeptide, and/or a nucleic acid molecule, and/or a vector, according to the disclosure. Also provided are pre-fusion RSV F polypeptides, nucleic acid molecules, and/or vectors, according to the disclosure, for use in inducing an immune response against RSV F protein in a subject. Further provided is the use of the pre-fusion RSV F polypeptides, and/or nucleic acid molecules, and/or vectors according to the disclosure for the manufacture of a medicament for use in inducing an immune response against RSV F protein in a subject.

The pre-fusion RSV F polypeptides, nucleic acid molecules, or vectors of the disclosure may be used for prevention (prophylaxis) and/or treatment of RSV infections. In certain embodiments, the prevention and/or treatment may be targeted at patient groups that are susceptible to RSV infection. Such patient groups include, but are not limited to, e.g., the elderly (e.g., >50 years old, >60 years old, and preferably >65 years old), the young (e.g., <5 years old, <1 year old), hospitalized patients and patients who have been treated with an antiviral compound but have shown an inadequate antiviral response.

The pre-fusion RSV F polypeptides, nucleic acid molecules and/or vectors according to the disclosure may be used, e.g., in stand-alone treatment and/or prophylaxis of a disease or condition caused by RSV, or in combination with other prophylactic and/or therapeutic treatments, such as (existing or future) vaccines, antiviral agents and/or monoclonal antibodies.

The disclosure further provides methods for preventing and/or treating RSV infection in a subject utilizing the pre-fusion RSV F polypeptides, nucleic acid molecules and/or vectors according to the disclosure. In a specific embodiment, a method for preventing and/or treating RSV infection in a subject comprises administering to a subject in need thereof an effective amount of a pre-fusion RSV F polypeptide, nucleic acid molecule and/or a vector, as described above. A therapeutically effective amount refers to an amount of a polypeptide, nucleic acid molecule or vector that is effective for preventing, ameliorating and/or treating a disease or condition resulting from infection by RSV. Prevention encompasses inhibiting or reducing the spread of RSV or inhibiting or reducing the onset, development or progression of one or more of the symptoms associated with infection by RSV. "Amelioration" as used in herein may refer to the reduction of visible or perceptible disease symptoms, viremia, or any other measurable manifestation of RSV infection.

For administering to subjects, such as humans, the disclosure may employ pharmaceutical compositions comprising a pre-fusion RSV F polypeptide, a nucleic acid molecule and/or a vector as described herein, and a pharmaceutically acceptable carrier or excipient. In the present context, the term "pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see *Remington's Pharmaceutical Sciences*, 18th edition, A. R. Gennaro, Ed., Mack Publishing Company [1990]; *Pharmaceutical Formulation Development of Peptides and Proteins*, S. Frokjaer and L. Hovgaard, Eds., Taylor & Francis [2000]; and *Handbook of Pharmaceutical Excipients*, 3rd edition, A. Kibbe, Ed., Pharmaceutical Press [2000]). The RSV F polypeptides or nucleic acid molecules are preferably formulated and administered as a sterile solution, although it may also be possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g., pH 5.0 to 7.5. The RSV F polypeptides typically are in a solution having a suitable pharmaceutically acceptable buffer, and the composition may also contain a salt. Optionally, stabilizing agent may be present, such as albumin. In certain embodiments, detergent is added. In certain embodiments, the RSV F polypeptides may be formulated into an injectable preparation.

In certain embodiments, a composition according to the disclosure further comprises one or more adjuvants. Adjuvants are known in the art to further increase the immune response to an applied antigenic determinant. The terms "adjuvant" and "immune stimulant" are used interchangeably herein, and are defined as one or more substances that cause stimulation of the immune system. In this context, an adjuvant is used to enhance an immune response to the RSV F polypeptides of the disclosure. Examples of suitable adjuvants include aluminium salts such as aluminium hydroxide and/or aluminium phosphate; oil-emulsion compositions (or oil-in-water compositions), including squalene-water emulsions, such as MF59 (see, e.g., WO 90/14837); saponin formulations, such as, for example, QS21 and Immunostimulating Complexes (ISCOMS) (see, e.g., U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, and the like; eukaryotic proteins (e.g., antibodies or fragments thereof (e.g., directed against the antigen itself or CD1a, CD3, CD7, CD80) and ligands to receptors (e.g., CD40L, GMCSF, GCSF, etc., which stimulate immune response upon interaction with recipient cells. In certain embodiments, the compositions of the disclosure comprise aluminium as an adjuvant, e.g., in the form of aluminium hydroxide, aluminium phosphate, aluminium potassium phosphate, or combinations thereof, in concentrations of 0.05 to 5 mg, e.g., from 0.075 to 1.0 mg, of aluminium content per dose.

The pre-fusion RSV F polypeptides may also be administered in combination with or conjugated to nanoparticles, such as, e.g., polymers, liposomes, virosomes, and virus-like particles. The pre-fusion F polypeptides may be combined with, encapsidated in or conjugated to the nanoparticles with or without adjuvant. Encapsulation within liposomes is described, e.g., in U.S. Pat. No. 4,235,877. Conjugation to macromolecules is disclosed, for example, in U.S. Pat. No. 4,372,945 or U.S. Pat. No. 4,474,757.

In other embodiments, the compositions do not comprise adjuvants.

In certain embodiments, the disclosure provides methods for making a vaccine against respiratory syncytial virus (RSV) comprising providing a composition according to the disclosure and formulating it into a pharmaceutically acceptable composition. The term "vaccine" refers to an agent or composition containing an active component effective to induce a certain degree of immunity in a subject against a certain pathogen or disease, which will result in at least a decrease (up to complete absence) of the severity, duration or other manifestation of symptoms associated with infection by the pathogen or the disease. In this disclosure, the vaccine comprises an effective amount of a pre-fusion RSV F polypeptide and/or a nucleic acid molecule encoding a pre-fusion RSV F polypeptide, and/or a vector comprising the nucleic acid molecule, which results in an immune response against the F protein of RSV. This provides a method of preventing serious lower respiratory tract disease leading to hospitalization and the decrease in frequency of complications such as pneumonia and bronchiolitis due to RSV infection and replication in a subject. The term "vaccine" according to the disclosure implies that it is a pharmaceutical composition, and thus typically includes a pharmaceutically acceptable diluent, carrier or excipient. It may or may not comprise further active ingredients. In certain embodiments, it may be a combination vaccine that further comprises other components that induce an immune response, e.g., against other proteins of RSV and/or against other infectious agents. The administration of further active components may, for instance, be done by separate administration or by administering combination products of the vaccines of the disclosure and the further active components.

Compositions may be administered to a subject, e.g., a human subject. The total dose of the RSV F polypeptides in a composition for a single administration can, for instance, be about 0.01 µg to about 10 mg, e.g., 1 µg to 1 mg, e.g., 10 µg to 100 µg. Determining the recommended dose will be carried out by experimentation and is routine for those skilled in the art.

Administration of the compositions according to the disclosure can be performed using standard routes of administration. Non-limiting embodiments include parenteral administration, such as intradermal, intramuscular, subcutaneous, transcutaneous, or mucosal administration, e.g., intranasal, oral, and the like. In one embodiment, a composition is administered by intramuscular injection. The skilled person knows the various possibilities to administer a composition, e.g., a vaccine, in order to induce an immune response to the antigen(s) in the vaccine.

A "subject" as used herein preferably is a mammal, for instance, a rodent, e.g., a mouse, a cotton rat, or a non-human primate, or a human. Preferably, the subject is a human subject.

The polypeptides, nucleic acid molecules, vectors, and/or compositions may also be administered, either as prime, or as boost, in a homologous or heterologous prime-boost regimen. If a boosting vaccination is performed, typically, such a boosting vaccination will be administered to the same subject at a time between one week and one year, preferably between two weeks and four months, after administering the composition to the subject for the first time (which is, in such cases, referred to as "priming vaccination"). In certain embodiments, the administration comprises a prime and at least one booster administration.

In addition, the polypeptides of the disclosure may be used as a diagnostic tool, for example, to test the immune status of an individual by establishing whether there are antibodies in the serum of such individual capable of binding to the polypeptide of the disclosure. The disclosure thus also relates to an in vitro diagnostic method for detecting the presence of an RSV infection in a patient, the method comprising the steps of: a) contacting a biological sample obtained from the patient with a polypeptide according to the disclosure; and b) detecting the presence of antibody-polypeptide complexes.

The disclosure further provides a method for stabilizing the pre-fusion conformation of an RSV F polypeptide comprising introducing one or more mutations in an RSV F1 domain, as compared to the wild-type RSV F1 domain, wherein the one or more mutations are selected from the group consisting of:

(a) a stabilizing mutation in the HRA region between the secondary structure elements in pre-fusion F that are transformed to one large coiled coil in post-fusion F; and (b) introduction of two cysteine residues close to the three-fold axis at the bottom of the pre-fusion RSV-F head N-terminal to the pre-fusion stem (residues 493-525), N-terminal of HRB that covalently cross-link the F1 subunits in the trimer.

In certain embodiments, the mutation in the HRA region is at position 161.

In certain embodiments, the mutation in the HRA region is at position 173.

In certain embodiments, the mutation in the HRA region is at position 182.

In certain embodiments, the introduction of two cysteine residues is at position 486 and 489.

In certain embodiments, the introduction of two cysteine residues is at position 486 and 487.

Stabilized pre-fusion RSV F polypeptides obtainable and/or obtained by such method also form part of the disclosure, as well as uses thereof as described above.

The disclosure is further explained in the following examples. The examples do not limit the disclosure in any way. They merely serve to clarify the disclosure.

EXAMPLES

Example 1

Preparation of Stable Pre-Fusion RSV F Polypeptides—Linkers and Trimerization Domains In the patent application PCT/EP2014/058353 (now published as WO 2014/174018), stabilized variants of soluble pre-fusion F protein (sF) were designed by stabilizing the two main regions that initiate refolding. The first strategy was to arrest the fusion peptide in its position and prevent it from getting released from the head region by fixing and joining the F1-F2 domains by a short loop. Release of the fusion peptide can be prevented by re-establishing a covalent connection of the N-terminus of F1 to C-terminus of F2. As shown in this example, several different linkers have been tried. The insertion of a 5-amino acid loop between F1 and F2, in particular, comprising the amino acid sequence GSGSG (SEQ ID NO:5), was most successful.

The other unstable region is the second heptad repeat (HRB) region that forms the trimeric helical stem region in pre-fusion F protein. Deletion of the transmembrane domain (TM) in the soluble F protein further destabilizes this region, which was compensated by the addition of different heterologous trimerization domains. The fully processed mature RSV-F ectodomain was fused C-terminally to different trimerization domains and at different positions (i.e., the F1 domain was truncated at different amino acid residues).

Several constructs were made based on either RSV A2 or B1 strains. Different trimerization domains were linked to the RSV F1 domain, which was truncated at different positions. Trimerization domains that were tested included the Fibritin motif (comprising the amino acid sequence GYIPEAPRDGQAYVRKDGEWVLLSTFL (SEQ ID NO:4)), and the "Fibritin long" motif, a longer, N-terminal extended Fibritin domain that includes its natural helical regions (comprising the amino acid sequence SSLQGD-VQALQEAGYIPEAPRDGQAYVRKDGEWVLLSTFL (SEQ ID NO:6)), that were added to the RSV F1 domain in frame (in register) with the presumed heptad repeat of the HRB region.

Further constructs that were made comprised heptad ideal helical trimeric coiled coils, or Isoleucine Zipper domains (IZ) (Suzuki et al., *Protein Engineering* 11:1051-1055 (1998)), comprising the amino acid sequence IEAIEKK (SEQ ID NO:7). According to the disclosure, different IZ domains were used, referred to as Isoleucine Zipper (L), comprising the amino acid sequence (I)EKKIEAIEK-KIEAIEKKIEAIEAIEKKIEA (SEQ ID NO:8) and Isoleucine Zipper (S), comprising the amino acid sequence EKKIEAIEKKIEAIEKKIEA (SEQ ID NO:3).

These IZ domains are comparable in structure to GCN4; however, the IZ domains are not natural sequences but designed to be optimal trimerization domains and, therefore, more stable.

Further constructs were made with other known trimerization domains:

```
GCN4II
                                     (SEQ ID NO: 9)
EDKIEEILSKIYHIENEIARIKKLIGEA

Optimized GCN4II
                                    (SEQ ID NO: 10)
EDKVEELLSKIYHIENRIARIEKLVGEA Matrillin-1 (long version)
                                    (SEQ ID NO: 11)
EEDPCECKSIVKFQTKVEELINTLQQKLEAVAKRIEALENKII Matrillin-1 short version that only contains
zipper domain:
                                    (SEQ ID NO: 12)
EELINTLQQKLEAVAKRIEALENKII
```

The following constructs were made:
Construct F18 comprised the Fibritin trimerization domain (SEQ ID NO:4) linked to amino acid residue 513 of the F1 domain.
Construct F19 comprised the Fibritin trimerization domain (SEQ ID NO:4) linked to amino acid residue 499 of the F1 domain.
Construct F20 comprised the Isoleucine Zipper (L) domain (SEQ ID NO:8) linked to amino acid residue 516 of the F1 domain and comprising additional modifications in HRB to optimize the hydrophobic nature of the heptad positions and facilitate in-frame fusion with the IZ domain.
Construct F21 also comprised Isoleucine Zipper (L) domain (SEQ ID NO:8), but linked to amino acid residue 501 of the F1 domain and without additional modifications in the HRB region.
Construct F22 comprised the Isoleucine Zipper (L) domain (SEQ ID NO:8) linked to amino acid residue 495 of the F1 domain and comprising additional modifications in HRB.
Construct F23 comprised the Isoleucine Zipper (S) domain (SEQ ID NO:3) linked to amino acid residue 495.
Construct F46 also comprised the Isoleucine Zipper (S) domain (SEQ ID NO:3) but linked to a longer RSV-F ectodomain, i.e., the F1 domain was truncated after amino acid residue 513.

All constructs comprised a HIS-tag.

The constructs were tested for expression levels, storage stability and antibody binding with the antibody CR9501. The amino acid sequences of the heavy and light chain variable regions, and of the heavy and light chain CDRs of this antibody are given below. CR9501 comprises the binding regions of the antibodies referred to as 58C5 in WO 2012/006596.

The constructs were synthesized and codon-optimized at GENEART® (Life Technologies, Carlsbad, Calif.). The constructs were cloned into pCDNA2004 or generated by standard methods widely known within the field involving site-directed mutagenesis and PCR and sequenced. The expression platform used was the 293Freestyle cells (Life Technologies). The cells were transiently transfected using 293Fectin (Life Technologies) according to the manufacturer's instructions and cultured for 5 days at 37° C. and 10% $CO_2$. The culture supernatant was harvested and spun for 5 minutes at 300 g to remove cells and cellular debris. The spun supernatant was subsequently sterile filtered using a 0.22 µm vacuum filter and stored at 4° C. until use.

Supernatants from day 5 were evaluated for F protein expression by Western blot using the monoclonal antibody CR9503, which comprises the heavy and light chain variable regions of the RSV F antibody Motavizumab (referred to as CR9503). The approximate expression levels of the pre-fusion RSV F protein constructs were assessed using CR9503, an anti-human IR-dye-conjugated secondary antibody (Li-Cor, Lincoln, Nebr.) or an HRP-conjugated mouse anti-human IgG (Jackson ImmunoResearch, West Grove, Pa.). The protein quantities were then estimated using a dilution series of purified RSV standard protein, either by eye or using the Odyssey CLx infrared imaging system. To evaluate construct stability and to identify positive or negative stabilizing effects of introduced trimerization motifs, the constructs capable of binding CR9501 were treated at a range of temperatures from 45° C. to 65° C. for 30 minutes to test the stability of the CR9501 epitope. This procedure is described in detail in Example 9. The results are summarized in Table 1.

TABLE 1

Expression and stability of RSV F constructs with different trimerization motifs

| RSV Protein | Description | | | | Stability* |
|---|---|---|---|---|---|
| | Trimerization motif | Modifications | Termination point | Expression (μg/ml) | |
| F18 | Fibritin | None | 513 | 2 | unstable |
| F19 | Fibritin | None | 499 | 0 | ND |
| F20 | Isoleucine zipper (L) | 502 509 516 Ile | 516 | 0 | ND |
| F21 | Isoleucine zipper (L) | None | 501 | 0 | ND |
| F22 | Isoleucine zipper (L) | K483E + E488K | 495 | 0 | ND |
| F23 | Isoleucine zipper (S) | None | 495 | 0.3 [1] | stable |
| F46 | Isoleucine zipper (S) | None | 513 | Did not express | ND |

*Stability is defined as described in Example 8;
ND: Not determined.
[1] Expression level determined by Western Blot as described in Example 1.

As can be seen in Table 1, the only constructs that were expressed were the Fibritin variant (F18) and F23. Although F18 was trimeric and showed expression, it was unstable upon storage at 4° C. In contrast, F23 was stable at 4° C., binds to the pre-fusion-specific antibodies, but appeared to be monomeric. Therefore, both variants F18 and F23 were used to optimize for both stability and trimerization.

Next, several constructs were made in which the fusion peptide at the N-terminus of F1 was fixed by fusion to the C-terminus of the F2 domain. All constructs comprised a His-tag. Several constructs were made including constructs in which both furin cleavage sites were mutated, resulting in a soluble F protein that still contained the p27 peptide (i.e., F12, F15.1, and F17). In other constructs, the 27-residue region (P27 loop) that is cleaved from the precursor F0 was replaced by an alternative closed loop, either by replacing the region of RSV-F by the "homologous" region of PIV-5 F, the pre-fusion F protein that had been produced and crystallized successfully (F25), or by replacing the region by a minimal (GS)n loop that would bridge the termini of F2 and F1 (F24), or by replacing the region by the central conserved region of RSV-G (F26). Homology modeling of RSV-F based on PIV-5 and in silico measurements resulted in the choice of a minimal loop of five amino acid residues between residues 108 and 136. As a linker, Gly (G) and Ser (S) residues were chosen, which are flexible and polar and have a high chance to be accommodated (F24). Additionally, F137 was mutated to S because the local modifications caused by the loop could displace the hydrophobic F and cause instabilities. This is shown below. In addition, the R106 is mutated to Q and 27 residues (109-135) are replaced by GSGSG (SEQ ID NO:5).

(SEQ ID NO: 2)
PAANNRARREAPQYMNYTINTTKNLNVSISKKRKRR$_{136}$FLGFLLGVG (SEQ ID NO: 17)
PAANNQAR················GSGSGR$_{136}$SLGFLLGVG

As shown in Table 2, all variants showed very low or no expression except for the variant with the short GSGSG (SEQ ID NO:5) loop (F24), which showed a much higher expression (44 μg/ml) compared to wild-type RSV F construct, i.e., a similar construct, without the linker (F11). F24, which was trimeric, however, was unstable upon storage like all the other variants with a C-terminal Fibritin trimerization motif. All variants contained a HIS-tag.

TABLE 2

Expression and stability of RSV F constructs with different F1-F2 linkers

| RSV Protein | Variant | Description | | | Termination point | Expr. (μg/ml) | Stability* |
|---|---|---|---|---|---|---|---|
| | | Trimerization motif | F1, F2 linker | Modifications | | | |
| F11 | B1 | None | None | None | 513 | 2.5 | stable |
| F18 | B1 | Fibritin | None | None | 513 | 2 | unstable |
| F12 | B1 | Fibritin | p27 | Furin site KO | 513 | 0.1 | unstable |
| F15.1 | B1 | None | p27 | Furin site KO | 525 | 0.5 | ND |
| F17 | A2 | Fibritin | p27 | Furin site KO | 513 | 0 | ND |
| F24 | B1 | Fibritin | Q_GSGSG_S (SEQ ID NO: 5) | None | 513 | 44 | unstable |
| F25 | B1 | Fibritin | PIV | None | 513 | 0 | ND |
| F26 | B1 | Fibritin | G CR | None | 513 | 0 | ND |

*Stability is defined as described in Example 8. Expression level determined as described in Example 1.

Next, the most favorable modifications were combined to find the optimal pre-fusion F polypeptides. Combinations were made of variants with the GSGSG (SEQ ID NO:5) loop, C-terminal truncation of F1, and the addition of either fibritin (SEQ ID NO:4) or the Isoleucine Zipper (S) motif (SEQ ID NO:3) (see Table 3).

TABLE 3

Expression and stability of RSV F constructs with combinations of optimizations according to Tables 1 and 2.

| RSV Protein | Variant | Termination point | Description | | | Stability CR9501 epitope) | |
|---|---|---|---|---|---|---|---|
| | | | Trimerization motif | F1, F2 linker | (μg/ml) | Heat (° C.) | Storage |
| F11 | B1 | 513 | None | None | 2.5 | 48 | Stable |
| F23 | B1 | 495 | Isoleucine zipper (S) | None | 0.3 | ND | Stable |

TABLE 3-continued

Expression and stability of RSV F constructs with combinations of optimizations according to Tables 1 and 2.

| RSV Protein | Variant | Termination point | Description Trimerization motif | F1, F2 linker | (µg/ml) | Stability CR9501 epitope) Heat (° C.) | Storage |
|---|---|---|---|---|---|---|---|
| F24 | B1 | 513 | Fibritin | Q_GSGSG_S (SEQ ID NO: 5) | 44 | 51 | Unstable |
| F45 | B1 | 495 | Fibritin | None | 0 | ND | ND |
| F44 | B1 | 495 | Fibritin | Q_GSGSG_S (SEQ ID NO: 5) | 0 | ND | ND |
| F49 | B1 | 495 | None | None | 2 | ND | Stable |
| F50 | A2 | 495 | None | None | 2 | ND | Stable |
| F43 | B1 | 495 | Isoleucine zipper (S) | Q_GSGSG_S (SEQ ID NO: 5) | 0.4 | 53 | Stable |
| F47 | A2 | 495 | Isoleucine zipper (S) | Q_GSGSG_S (SEQ ID NO: 5) | 5 | 52 | Stable |
| F56 | B1 | 513 | Isoleucine zipper (S) | Q_GSGSG_S (SEQ ID NO: 5) | 0.4 | ND | Stable |
| F46 | B1 | 513 | Isoleucine zipper (S) | None | 0 | ND | unstable |
| F42 | B1 | 513 | None | Q_GSGSG_S (SEQ ID NO: 5) | 20 | 54 | Stable |
| F57 | A2 | 513 | None | Q_GSGSG_S (SEQ ID NO: 5) | 2-10 | 54 | Stable |

ND is not determined
*Storage stability as determined in Example 8.
*Heat stability as determined in Example 9.
Expression level as determined by Western blotting (described in Example 1)

Addition of the GSGSG (SEQ ID NO:5) loop always increased the expression of functional constructs as well as the heat stability of the protein. Combination of the GSGSG (SEQ ID NO:5) loop with the truncated F and isoleucine zipper (S) motif (F43, F47) showed good expression, heat stability and good stability upon storage at 4° C. However, these variants were still monomeric. The isoleucine zipper (S) trimerization motif showed higher expression with an F variant that was C-terminally truncated F at position 495 (compare F43 with F56 and F23 with F46). In contrast, for variants with the Fibritin trimerization domain, a truncation at position 513 showed high expression compared to truncation at position 495, which showed no expression (compare F24 with F44).

Because the HIS-tag could interfere with the native folding of the trimers, variants were made without the HIS-tag for the Fibritin and the isoleucine zipper (S) variant (Table 4).

TABLE 4

| Expression and stability of RSV F constructs with and without HIS-tag | | | | | | | | | |
|---|---|---|---|---|---|---|---|---|---|
| RSV Protein | Variant | Trimerization motif | F1, F2 linker | Termination point | Expression µg/ml | Trimerization % | Heat (° C.) | Storage | Tags |
| F24 | B1 | Fibritin | Q_GSGSG_S (SEQ ID NO: 5) | 513 | 44 | Trimeric (SEC) | 51 | unstable | His-tag |
| F24– | B1 | Fibritin | Q_GSGSG_S (SEQ ID NO: 5) | 513 | 55 | 100% (Native) | ND | unstable | None |
| F47 | A2 | Isoleucine zipper (S) | Q_GSGSG_S (SEQ ID NO: 5) | 495 | 5 | 0% (Odyssey) | 52 | stable | His-tag |
| F47– | A2 | Isoleucine zipper (S) | Q_GSGSG_S (SEQ ID NO: 5) | 495 | 10 | 2-5% (Odyssey) | 53 | stable | None |
| A2_F24 | A2 | Fibritin | Q_GSGSG_S (SEQ ID NO: 5) | 513 | 5.3 | Trimeric (Native) | 48.75 | unstable | None |

*Storage stability determined as described in Example 8; Heat stability determined as described in Example 9; ND: not determined.

Strikingly, deletion of the HIS-tag increased expression in F47. Moreover, for F47, it increased the trimeric content slightly and, for F24, it only increased the expression level moderately.

Next, several alternative trimerization domains and truncations were tested in combination with the GSGSG (SEQ ID NO:5) loop stabilized F variant (F47) (see Table 5). All variants have a GSGSG (SEQ ID NO:5) loop and contain a HIS-tag.

TABLE 5

Expression and stability of RSV F variants with alternative trimerization domains

| RSV Protein | Variant | Trimerization motif | Modifications | Termination point | Expression (μg/ml) | Trimerization % | Antibody binding CR9501 | CR9503 |
|---|---|---|---|---|---|---|---|---|
| F47 | A2 | Isoleucine zipper (S) | None | 495 | 5 | 0% | + | + |
| P1 | B1 | Isoleucine zipper (S) | S502T | 502 | 3.5 | 0% | + | + |
| Mat1 | A2 | Matrillin long | None | 520 | 12 | tri and hexamers | − | + |
| Mat2 | A2 | Matrillin short | None | 516 | 0 | ND | − | − |
| Mat3 | A2 | Matrillin short | None | 495 | 1.5 | ND | − | − |
| opt GCN | A2 | GCN4II optimized | None | 516 | 0 | ND | − | − |
| opt GCN + L512K | A2 | GCN4II optimized | L512K | 516 | 1 | ND | + | − |

Antibody binding is defined as binding on the day of harvest (as described in Example 8; + indicates binding; − indicates no binding.
Expression level is determined as described in Example 1.
ND: not determined Only the Matrillin 1 domain (S. A. Dames et al., Nat. Struc. Biol. 5(8), 1998) that contains both the N-terminal zipper domain and the C-terminal part with the cysteine residues that can potentially form inter-trimeric disulfide bridges was found to enable higher expression levels than F47 (Table 5, Matrillin long). Moreover, the variant with the Matrillin long trimerization motif shows trimeric F proteins. However, the product did not bind to the pre-fusion-specific Mab CR9501 and also showed hexameric species, which makes the Matrillin 1 trimerization domain not suitable for production of trimeric native F protein. None of the Matrillin-based or the GCN4II-based zipper motifs showed increased expression or stability relative to F47 (Table 5, Matrillin short, GCN4II optimized). Again, truncation at 495 results in higher expression levels. Addition of a GCN4 motif, which contained an optimized trigger sequence, showed no expression.

GCN4II is a trimerization domain that is used successfully for stabilizing the pre-fusion trimer of parainfluenza type 5 (Yin et al., Nature 439:38-44, 2006) and has also been tried by others to stabilize RSV pre-fusion F (as disclosed in, e.g., WO 2010/149743, WO 2010/149745, WO 2009/079796, and WO 2010/158613). The GCN4II trimerization domain was evaluated and compared with the constructs that contain the Isoleucine Zipper (S) domain (SEQ ID NO:3) or the Fibritin (SEQ ID NO:4) domain (results shown in Table 6). These variants were also compared with anther modifications, i.e., a short linker based on a single Lysine and the L512K mutation. All variants contained a HIS-tag.

TABLE 6

Expression and stability of RSV F variants with GCN4II, L512K and p27 replacement (single amino acid linker (K) between F1 and F2)

| RSV Protein | Variant | Trimerization motif | F1, F2 linker | Modifications | Termination point | Expr. (μg/ml) | Heat (° C.) | Storage* |
|---|---|---|---|---|---|---|---|---|
| F18 | B1 | Fibritin | None | None | 513 | 2 | ND | unstable |
| F24 | B1 | Fibritin | Q_GSGSG_S (SEQ ID NO: 5) | None | 513 | 44 | 51 | unstable |
| F43 | B1 | Isoleucine zipper (S) | Q_GSGSG_S (SEQ ID NO: 5) | None | 495 | 0.4 | 53 | stable |
| P1 | B1 | Isoleucine zipper (S) | Q_GSGSG_S (SEQ ID NO: 5) | S502T | 502 | 3.5 | 54 | ND |
| F42 | B1 | None | Q_GSGSG_S (SEQ ID NO: 5) | None | 513 | 16.1 | 54 | stable |
| P2 | B1 | None | K | None | 513 | 14.3 | 54 | stable |
| P3 | B1 | GCN4II | None | L512K | 516 | 0 | ND | ND |
| P4 | B1 | GCN4II | K | L512K | 516 | 0 | ND | ND |
| P5 | B1 | GCN4II | K | L512K | 516 | 0 | ND | ND |
| P6 | A2 I | GCN4II | K | L512K | 516 | 0 | ND | ND |
| P7 | A2 II | GCN4II | K | L512K | 516 | 0 | ND | ND |

Storage stability determined as described in Example 8;
Expression levels determined as described in Example 1;
Heat stability determined as described in Example 9;
ND: not determined.

The short linkage between F1 and F2 appears to be comparable to the GSGSG loop (SEQ ID NO:5). Addition of the GCN4II motif does not result in any F expression in any of the tested constructs (i.e., the RSV A2 F sequence described in WO 2010/149743 or WO 2010/149745, the RSV A2 F sequence used according to the disclosure, nor the RSV B1 F sequence).

It was shown that the introduction of these two types of modifications, i.e., introduction of a linking sequence and the heterologous trimerization domain, was not enough to enable the expression of stable trimeric pre-fusion F protein. Apart from the two main regions of instability that were stabilized, i.e., the HRB and the fusion peptide, as described above, other regions in the pre-fusion F protein also contribute and/or accommodate the dramatic refolding to post-fusion F, and more positions in the sequence can be optimized to stop the pre-fusion F protein from refolding. Therefore, different amino acid residues in the HRA and HRB domains and in all domains that contact these regions in pre-fusion F were mutated to increase the pre-fusion structure stability, as described in the following Examples.

Example 2

Preparation of Stable Pre-Fusion RSV F Polypeptides—Stabilizing Mutations

Because the trimeric content (for construct F47) and storage stability (for construct F24) was not optimal, further variants were made that contained point mutations to increase expression levels, stability and native trimeric structure. The results are shown in Tables 7 and 8.

TABLE 7

Expression and stability of F47- variants

| RSV Protein | Expression (μg/ml) | Trimerization % | Heat (° C.) |
|---|---|---|---|
| F47- | 10 | 2-5% | 53 |
| F47- + K465E | 6 | 2.4% | ND |
| F47- + D479K | 5 | 29% | 50.77 |
| F47- + K176M | 13 | 5% | ND |
| F47- + K209Q | 9 | 3% | 52.9 |
| F47- + S46G | 38 | 11% | 59.38 |
| F47- + S215P | 8 | 1-2% | 57.21 |
| F47- + N67I | 15 | 2% | 59.84 |
| F47- + K465Q | 18 | 2% | 54.3 |
| F47- S46G + N67I | 31 | 6% | >60 |
| F47- S46G + S215P | 38 | 6% | >60 |
| F47- K465Q + K209Q | 12 | 1% | 53.3 |
| F47- K465Q + S46G | 28 | 7% | 57.7 |
| F47- K465Q + N67I | 17 | 2% | 59 |
| F47- K209Q + N67I | 15 | 4% | >60 |
| F47- K209Q + S215P | 15 | 2% | 56.7 |

ND: not determined;
Expression level determined as described in Example 1.
Heat stability determined as described in Example 9.

Nomenclature of mutations based on wt sequence (SEQ ID NO:1).

All constructs are variants of F47-: type A2, Isoleucine Zipper (S) motif (SEQ ID NO:3), GSGSG (SEQ ID NO:5) linker; termination point 495, no HIS-tag (SEQ ID NO:16). As shown in Table 7, many mutations increased the expression of F47-, but only the variant F47_S46G also showed a higher level of trimers besides the high expression.

Table 8 shows the results of the expression and stability of F24 variants. All variants were of RSV type A2, with fibritin motif, GSGSG (SEQ ID NO:5) linker; termination point 513, no HIS-tag.

TABLE 8

Expression and stability of A2_F24- (SEQ ID NO: 19) variants

| RSV Protein | Expression (μg/ml) | Storage Endpoint | Storage Association phase |
|---|---|---|---|
| A2_F24 | 5.3 | 69 | ND |
| A2_F24 K508E | 5.3 | 64 | ND |
| A2_F24 K498E | 1.7 | ND | ND |
| A2_F24 E487I | 25.0 | 10 | ND |
| A2_F24 E487K | 7.1 | ND | ND |
| A2_F24 E487N | 42.4 | 22 | ND |
| A2_F24 E487P | 12.8 | 46 | ND |
| A2_F24 E487Q* | 14.8 | 50 | ND |
| A2_F24 E487R | 8.7 | 59 | ND |
| A2_F24 E487S | 6.7 | 46 | ND |
| A2_F24 E487Y | 10.5 | 36 | ND |
| A2_F24 D486N | 31.2 | 19 | ND |
| A2_F24 D479N | 5.2 | ND | ND |
| A2_F24 D479K | 1.5 | 62 | ND |
| A2_F24 E472Q | 1.9 | ND | ND |
| A2_F24 E472K | 0.9 | ND | ND |
| A2_F24 K465E | 14.8 | 76 | ND |
| A2_F24 K465Q* | 13.6 | 92 | Not stable |
| A2_F24 E463K | 3.1 | ND | ND |
| A2_F24 E463Q | 6.0 | ND | ND |
| A2_F24 G430S | 4.8 | ND | ND |
| A2_F24 N428R | 5.2 | 35 | ND |
| A2_F24 N426S | 18.6 | 71 | ND |
| A2_F24 K421N | 9.2 | 75 | ND |
| A2_F24 E328K | 9.5 | 21 | ND |
| A2_F24 T311S | 3.5 | 70 | ND |
| A2_F24 I309V | 11.3 | 69 | ND |
| A2_F24 D269V | 0.0 | ND | ND |
| A2_F24 S215P* | 18.7 | 99 | Stable |
| A2_F24 K209Q | 31.4 | 63 | ND |
| A2_F24 V207P | 3.3 | 79 | ND |
| A2_F24 I206P | 5.4 | 55 | ND |
| A2_F24 L204P | 5.9 | ND | ND |
| A2_F24 L203P | 0.8 | ND | ND |
| A2_F24 Q202P | 4.4 | ND | ND |
| A2_F24 K201Q | 21.3 | 62 | ND |
| A2_F24 D194P | 1.9 | ND | ND |
| A2_F24 L193P | 6.5 | 42 | ND |
| A2_F24 V192P | 0.6 | 32 | ND |
| A2_F24 V185N | 50.2 | 38 | ND |
| A2_F24 GV184EG | 3.5 | ND | ND |
| A2_F24 G184N | 59.8 | 37 | ND |
| A2_F24 V178P | 14.8 | 23 | ND |
| A2_F24 A177P | 2.0 | ND | ND |
| A2_F24 K176M | 14.7 | 58 | ND |
| A2_F24 K176E | 0.7 | ND | ND |
| A2_F24 N175P | 34.3 | 55 | ND |
| A2_F24 S169P | 0.5 | ND | ND |
| A2_F24 K168P | 0.1 | ND | ND |
| A2_F24 K166P | 12.3 | 45 | ND |
| A2_F24 V157P | 0.2 | ND | ND |
| A2_F24 E92D | 47.4 | 94 | Not stable |
| A2_F24 K85E | 1.1 | ND | ND |
| A2_F24 K80E | 51.9 | 60 | ND |
| A2_F24 K77E | 22.4 | ND | ND |
| A2_F24 N67I* | 89.8 | 101 | Stable |
| A2_F24 I57V | | ND | ND |
| A2_F24 VI56IV | 16.5 | 54 | ND |
| A2_F24 S46G* | 40.7 | 96 | Not stable |

The *marked constructs were tested for trimerization and were all found to be trimeric.
Expression level determined as described in Example 1.
Endpoint stability is shown here as the percentage of pre-fusion antibody binding (CR9501) after 5 days of storage at 4° C. relative to day 1; Association phase stability is determined as described in Example 10.

Many mutations increased the expression of A2_F24-. For most mutations there was an apparent correlation between improved expression in F47- background (Table 7) and A2_F24- background (Table 8). N67I had more positive impact on F expression in A2_F24- background. The most significant increase in expression was obtained with the single point mutations: S46G, S215P, N67I, K80E, E92D, D486N, G184N, V185N, E487N, N175P, K209Q, E487I, E487Q, K77E, K201Q, N426S and K465Q. In the initial screening using the endpoint stability assay (Example 8), the variants with the highest expression showed the best stability upon storage as well (E92D, K465Q, K465E, N426S, S46G, S215P and N67I). To evaluate if these mutations indeed were stabilizing the pre-fusion conformation, culture supernatants were diluted to 5 and 10 µg/ml based on quantitative Western results and these were stored up to 33 days at 4° C. As single point mutants, only N67I and S215P were completely stable over time (see Example 10).

Subsequently, several mutations that showed high expression and good stability of the pre-fusion conformation were combined to evaluate whether the stabilizations were additive or had a possible synergistic effect (Table 9).

TABLE 9

Expression and stability of variants of A2_F24 with two additional mutations.

| RSV Protein | Expression (µg/ml) | stability* |
|---|---|---|
| A2_F24 K465Q + S46G | 21.8 | Not stable |
| A2_F24 K465Q + N67I | 122.3 | Stable |
| A2_F24 K465Q + E92D | 10.5 | Stable |
| A2_F24 K465Q + S215P | 59.8 | Stable |
| A2_F24 S46G + N67I | 115.5 | Stable |
| A2_F24 S46G + E92D | 14.3 | Not stable |
| A2_F24 N67I + E92D | 134.2 | Stable |
| A2_F24 N67I + S215P | 152.1 | Stable |
| A2_F24 E92D + S215P | 49.1 | Stable |
| A2_F24 K465Q + S215P | 53.3 | Stable |
| A2_F24 S46G + S215P | 43.8 | Stable |

Storage stability refers to the association phase analysis illustrated in Example 10.

Expression level was determined as described in Example 1.

All variants are variants of F24-: type A2, fibritin motif, GSGSG (SEQ ID NO:5) linker; termination point 513, binding to all Mabs, no HIS-tag (SEQ ID NO:19).

When the previously identified point mutations were combined, very interesting synergistic effects could be observed especially in terms of expression levels with the combinations involving N67I as the most potent. All produced double mutants where either N67I and S215P was included were stable after more than 30 days storage at 4° C. (Example 10). Strikingly, the mutation N67I was found to have the strongest effect on expression levels of pre-fusion F when included in the double mutants. Next, combinations with the S215P mutations resulted in a reasonable expression. Combination of N67I with S215P was selected since it led to a very high expression level, and because both point mutations were stable upon storage. Additionally, it was observed that both N67I and S215P had the ability to stabilize some of the mutants that as single mutations were unstable indicating that the region where these two mutations are found is central for the conformation changes the protein undergoes during the transition to the post-fusion conformation.

It thus has been shown that at least some mutations resulted in increased expression levels and increased stabilization of the pre-fusion RSV protein. It is expected that these phenomena are linked. The mutations described in this Example all resulted in increased production of pre-fusion F polypeptides. Only a selection of these polypeptides remained stable upon long storage (see Example 10). The stability assay that was used is based on the loss of the pre-fusion-specific CR9501 epitope in the top of the pre-fusion F protein in a binding assay and it may not be sensitive enough to measure all contributions to stability of the whole protein. The mutation for which only increased expression is observed are therefore (very likely stabilizing) potential mutations that can be combined with other stabilizing mutations to obtain a pre-fusion F construct with high stability and high expression levels.

Next, it was verified whether the N67I-S215P double mutation, like the single mutations, was able to stabilize point mutations that as single mutants were deemed unstable based on the criteria used. Extra mutations were selected based on the favorable expression levels and stability according to Table 8. Triple mutant RSV-F variants were constructed and tested for expression levels and stability (Table 10).

TABLE 10

Expression and stability of variants of F24_N67I + S215P with one additional mutation.

| RSV Protein | Expression (µg/ml) | stability* |
|---|---|---|
| A2_F24 N67I + S215P + K507E | 344.6 | ++ |
| A2_F24 N67I + S215P + E487I | 239.4 | +++ |
| A2_F24 N67I + S215P + E487N | 285.2 | +++ |
| A2_F24 N67I + S215P + E487Q | 360.7 | +++ |
| A2_F24 N67I + S215P + E487R | 130.9 | +++ |
| A2_F24 N67I + S215P + D486N | 292.6 | +++ |
| A2_F24 N67I + S215P + D479N | 97.1 | +++ |
| A2_F24 N67I + S215P + K465Q | 283.3 | +++ |
| A2_F24 N67I + S215P + N426S | 316.3 | +++ |
| A2_F24 N67I + S215P + K421N | 288.4 | +++ |
| A2_F24 N67I + S215P + K209Q | 245.0 | +++ |
| A2_F24 N67I + S215P + K201Q | 231.9 | +++ |
| A2_F24 N67I + S215P + V185N | 445.1 | +++ |
| A2_F24 N67I + S215P + G184N | 326.7 | +++ |
| A2_F24 N67I + S215P + E92D | 308.8 | + |
| A2_F24 N67I + S215P + K80E | 210.6 | + |
| A2_F24 N67I + S215P + S46G | 199.4 | +++ |

All variants are variants of A2_F24_N67I + S215P type A2, fibritin motif, GSGSG (SEQ ID NO: 5) linker; termination point 513, binding to all Mabs, no HIS-tag (SEQ ID NO: 21).
*stability refers to the association phase analysis illustrated in Example 10.
+ means <10% loss of CR9501 binding after 5 days;
++ means <5% loss of CR9501 binding after 5 days;
+++ means 0% loss of CR9501 binding after 5 days.

Again, an additive effect on the expression levels was observed. As expected, D479N and E487R triple mutants express at somewhat lower levels because the single mutants were also among the lowest of the selected mutations (Table 8). Because of the stabilizing effect of the N67I+S215P mutation, additional mutations that are unstable as single mutants resulted in stable pre-fusion F variants when they were added to the A2_F24 N67I+S215P background. Some very illustrative examples are the triple mutants with the additional V185N, G184N or E487N, which showed high expression but low stability as single mutants (Table 8) but showed even higher expression and were highly stable when added to the A2_F24 N67I+S215P background.

Stabilizing Mutations Also Stabilize RSV-F Protein from Other Strains and Also in Processed F Variant.

Several mutations that showed high expression and good stability of the pre-fusion conformation were applied to RSV F proteins of other strains and were applied to a RSV A2 F variant without furin cleavage site mutations (F18: SEQ ID NO:71) to evaluate whether the modifications are a universal solution to stabilize RSV pre-fusion F (Table 11).

TABLE 11

Expression and stability of variants of A2_F18 with additional mutations and F from strain B1 (SEQ ID NO: 2) and type A CL57-v224 (SEQ ID NO: 69).

| RSV protein | Seq ID | Relative* expression (CR9503) | Stability** after day 5, % |
|---|---|---|---|
| A2_F18 | 71 | 0.018 | 0.0 |
| A2_F18 N67I | | 0.449 | 73.2 |
| A2_F18 S215P | | 0.129 | 9.1 |
| A2_F18 E487Q | | 0.006 | NA |
| A2_F18 N67I, S215P | 72 | 0.484 | 103.4 |
| A2_F18 N67I, E487Q | | 0.340 | 92.1 |
| A2_F18 N67I, S215P, E487Q | 76 | 0.355 | 92.7 |
| A2_F18 N67I, S215P, E92D | 78 | 0.318 | 96.0 |
| A2_F18 N67I, S215P, D486N | 79 | 0.522 | 101.3 |
| A2_F18 N67I, S215P, K201N | 77 | 0.643 | 102.7 |
| A2_F18 N67I, S215P, K66E | | 0.800 | 103.0 |
| A2_F18 N67I, S215P, S46G, K66E | | 0.820 | 103.5 |
| A2_F18 N67I, S215P, E487Q, K66E | | 0.704 | 99.5 |
| A2_F18 N67I, S215P, E92D, K66E | | 0.905 | 98.8 |
| A2_F18 N67I, S215P, D486N, K66E | | 0.863 | 96.6 |
| A2_F18 N67I, S215P, K201N, K66E | | 1.021 | 105.5 |
| A2_F18 N67I, S215P, D486N, K66E, I76V | | 0.594 | 95.0 |
| B1_N67I, S215P | 73 | 0.434 | 90.9 |
| B1_N67I, S215P loop | 22 | 0.552 | 108.2 |
| CL57v224_N67I, S215P | 74 | 0.698 | 94.9 |
| CL57v224_N67I, S215P loop | 75 | 0.615 | 98.4 |

Protein expression (concentration in the supernatant of transiently transfected cells) was measured by Quantitative Octet method.
*Relative expression is normalized to expression of A2_F24_N67I, S215P, E487Q (SEQ ID NO: 33)
**Stability—is expressed as % protein concentration measured after storage at 4° C. for 5 days, relative to the day of harvest.
The concentrations were measured by Quantitative Octet method using CR9501 antibody.
NA—data not available: no CR9501 binding was detected.

When the previously identified point mutations were introduced in A2_F18 (SEQ ID NO:71), the stability and expression levels were very similar compared with the single chain F24 (SEQ ID NO:21) variant that contained a short loop between F1 and F2. Again, synergism was observed showing higher expression and stability when mutations were added to variants that contained the N67I or the double mutation N67I, S215P. The double-point mutation N67I, S215P did not only stabilize the pre-fusion F of the A2 strain but also pre-fusion of B1 and CL57-v224 strain (Table 11).

Stabilizing Mutations Also Stabilize Full-Length RSV-F Protein.

Several mutations that showed high expression and good stability of the pre-fusion conformation in the soluble version of RSV-F corresponding to the ectodomain, were applied to the full-length RSV-F protein. The mutations were introduced in full-length RSV-F with or without furin cleavage site mutations. No trimerization domain was fused to these variants (Table 12).

TABLE 12

Expression and stability of variants of full-length versions of A2_F18 and A2_F24 with additional mutations.

| RSV F protein variant* | | | Attributes | |
|---|---|---|---|---|
| Amino acid substitutions | SEQ ID NO: | F1, F2 linker | Expression, fold increase** | Heat-stability*** |
| None (F A2 wild-type, full length) | 1 | none | 1 | – |
| N67I | | none | 1.4 | N.D. |
| S215P | | none | 1.4 | N.D. |
| E92D | | none | 1.4 | N.D. |
| N67I, K465Q | | none | 1.4 | N.D. |
| N67I, S46G | | none | 0.2 | N.D. |
| N67I, E92D | | none | 1.4 | N.D. |
| N67I, K80E | | none | 2.3 | N.D. |
| N67I, G184N | | none | 1.5 | N.D. |
| N67I, V185N | | none | 1.4 | N.D. |
| N67I, E487Q | | none | 2.5 | N.D. |
| N67I, S215P, V185N | | none | 2.7 | N.D. |
| N67I, S215P, K508E | | none | 3.0 | N.D. |
| N67I, S215P, K80E | | none | 3.1 | N.D. |
| N67I, S215P, K465Q | | none | 2.9 | N.D. |
| N67I, S215P | 80 | none | 2.4 | ++ |
| N67I, S215P, G184N | | none | 7.6 | ++ |
| N67I, S215P, E92D | 82 | none | 6.8 | N.D. |
| N67I, S215P, S46G | 88 | none | 6.8 | + |
| N67I, S215P, D486N | 86 | none | 5.9 | +++ |
| N67I, S215P, E487Q | 84 | none | 6.2 | N.D. |
| N67I, S215P, S46G, K66E | | none | 12.1 | +++ |
| N67I, S215P, D486N, K66E | | none | 9.2 | +++ |
| N67I, S215P, S46G, E92D, K66E | | none | 11.8 | +++ |
| N67I, S215P, S46G, E487Q, K66E | | none | 11.0 | +++ |
| N67I, S215P, S46G, D486N, K66E | | none | 10.5 | +++ |
| N67I, S215P, D486N, K66E, I76V | | none | 7.2 | +++ |
| N67I, S215P, S46G, K66E, I76V | | none | 9.7 | +++ |
| N67I, S215P, S46G, K80E | | none | 4.5 | N.D. |
| N67I + S215P + G184N + K80E + E92D + E487Q + S46G | | none | 9.1 | N.D. |
| None | | Q_GSGSG_S (SEQ ID NO: 5) | 3.8 | – |
| N67I, S215P | 81 | Q_GSGSG_S (SEQ ID NO: 5) | 6.2 | N.D. |
| N67I, S215P, G184N | | Q_GSGSG_S (SEQ ID NO: 5) | 7.2 | ++ |
| N67I, S215P, E92D | 83 | Q_GSGSG_S (SEQ ID NO: 5) | 5.9 | N.D. |
| N67I, S215P, S46G | 89 | Q_GSGSG_S (SEQ ID NO: 5) | 5.3 | ++ |
| N67I, S215P, D486N | 87 | Q_GSGSG_S (SEQ ID NO: 5) | 5.2 | +++ |
| N67I, S215P, E487Q | 85 | Q_GSGSG_S (SEQ ID NO: 5) | 4.6 | N.D. |
| N67I, S215P, S46G, K66E | | Q_GSGSG_S (SEQ ID NO: 5) | 11.7 | +++ |
| N67I, S215P, D486N, K66E | | Q_GSGSG_S (SEQ ID NO: 5) | 13.8 | +++ |
| N67I, S215P, D486N, K66E, I76V | | Q_GSGSG_S (SEQ ID NO: 5) | 6.8 | +++ |

TABLE 12-continued

Expression and stability of variants of full-length versions of A2_F18 and A2_F24 with additional mutations.

| RSV F protein variant* | | Attributes | |
|---|---|---|---|
| Amino acid substitutions | SEQ ID NO: | F1, F2 linker | Expression, fold increase** | Heat-stability*** |
| N67I + S215P + G184N + K80E + E92D + E487Q + S46G | | Q_GSGSG_S (SEQ ID NO: 5) | 3.6 | N.D. |

Expression level determined using FACS.
N.D.—not determined.
*all variants are based on RSV A2 F protein sequence.
**comparing to wild-type protein, fold increase of MFI on 9503.
Stability was assessed by heat treatment of the HEK293T cells for 5-10 minutes at 46° C., 55.3° C., 60° C.
***legend for the stability readout
− decrease in binding to pre-fusion-specific Mab CR9501 binding after 46° C. (e.g., wild-type)
+ slight decrease of CR9501 binding after 46° C. but not to same strong extent as wild-type
++ no change in CR9501 binding up to 60° C.; at 60° C. some decrease in CR9501 binding
+++ no change in CR9501 binding at 60° C.

The previously identified stabilizing point mutations were also stabilizing in the full-length F protein. The increase in expression level was less pronounced but showed the same trend. This may be caused by the different background the mutations were introduced in but may also be caused by the different quantification method (FACS versus Western blot) and a biological maximum of expression due to recycling of surface proteins. Introduction of the linking sequence (or short loop) increased expression and stability and the point mutations did so too. The point mutations were not or barely synergistic with the short loop (similar as to what was found for the soluble protein (Tables 9-11).

Because the point mutation at position 67 had such a positive effect on expression level and stability, all amino acid substitutions were tested for this position to study whether the most optimal were chosen or whether these positions can be improved (Table 13).

TABLE 13

Full substitution analysis of expression and stability for position 67 in the A2_F24 background.

| Amino acid substitution | Relative Expression* | Stability** after day 4, % | Stability** after day 10, % |
|---|---|---|---|
| N67A | 1.696 | 0.0 | 0.0 |
| N67C | 1.759 | 16.7 | 0.0 |
| N67D | 1.702 | 0.0 | 0.0 |
| N67E | 1.357 | 0.0 | 0.0 |
| N67F | 2.565 | 102.2 | 108.1 |
| N67G | 0.853 | NA | NA |
| N67H | 1.509 | 0.0 | 0.0 |
| N67I | 3.773 | 98.2 | 102.7 |
| N67K | 0.487 | NA | NA |
| N67L | 3.609 | 107.5 | 96.4 |
| N67M | 2.579 | 87.3 | 78.7 |
| N67P | 2.414 | 14.3 | 0.0 |
| N67Q | 0.955 | NA | NA |
| N67R | 0.523 | NA | NA |
| N67S | 1.277 | 0.0 | 0.0 |
| N67T | 1.577 | 0.0 | 0.0 |
| N67V | 2.457 | 84.2 | 77.0 |
| N67W | 1.794 | 99.9 | 104.3 |
| N67Y | 1.830 | 61.3 | 45.8 |

*Relative expression—protein concentration was measured by Quantitative Octet method using CR9503 antibody and expressed relative to concentration of A2_F24 (SEQ ID NO: 19).
**Stability—is expressed as % protein concentration measured after storage at 4° C. for 5 and 10 days, relatively to the day of harvest.
The concentrations were measured by Quantitative Octet method using CR9501 antibody.
NA—data not available: no CR9501 binding was detected.

As shown in Table 13, primarily hydrophobic residues and particularly Ile, Leu and Met at position 67 were able to increase expression and stability. Ile is the residue that increased expression and stability most. Residues Glu and Gln, the smallest residue Gly and the positively charged residues Arg and Lys had the most destabilizing effect at position 67 on the pre-fusion conformation.

Example 3

Preparation of Stable Pre-Fusion RSV F Polypeptides According to this Disclosure In the research that led to this disclosure, further stabilized variants of soluble pre-fusion F protein (sF) were designed by stabilizing the two main regions that initiate refolding. The first strategy was to prevent the refolding of the HRA region into a coiled coil. The second strategy was to construct disulfide bridges N-terminal to HRB to prevent the relocation of the HRB to form the six-helix bundle by docking onto the HRA coiled coil.

The constructs were tested for expression levels, storage stability and antibody binding with the antibody CR9501. The amino acid sequences of the heavy and light chain variable regions, and of the heavy and light chain CDRs of this antibody are given below. CR9501 comprises the binding regions of the antibodies referred to as 58C5 in WO 2012/006596. The constructs were synthesized and codon-optimized by GENEART® (Life Technologies, Carlsbad, Calif.). The constructs were cloned into pCDNA2004 or generated by standard methods widely known within the field involving site-directed mutagenesis and PCR and sequenced. The expression platform used was the 293Freestyle cells (Life Technologies). The cells were transiently transfected using 293Fectin (Life Technologies) according to the manufacturer's instructions and cultured for 5 days at 37° C. and 10% $CO_2$. The culture supernatant was harvested and spun for 5 minutes at 300 g to remove cells and cellular debris. The spun supernatant was subsequently sterile filtered using a 0.22 µm vacuum filter and stored at 4° C. until use.

Supernatants from day 5 were evaluated for F protein expression by Western blot using the monoclonal antibody CR9503, which comprises the heavy and light chain variable regions of the RSV F antibody Motavizumab (referred to as CR9503). The approximate expression levels of the pre-fusion RSV F protein constructs were assessed using CR9503, an anti-human IR-dye-conjugated secondary antibody (Li-Cor, Lincoln, Nebr.) or an HRP-conjugated mouse anti-human IgG (Jackson ImmunoResearch, West Grove, Pa.). The protein quantities were then estimated using a dilution series of purified RSV standard protein, either by eye or using the Odyssey CLx infrared imaging system. To evaluate construct stability and to identify positive or negative stabilizing effects of introduced trimerization motifs, the constructs were tested for binding to pre-fusion-specific antibodies after 5, 14 or 30 days of storage at 4° C. This procedure is described in detail in Example 10.

Next, the most favorable modifications were combined to find the optimal pre-fusion F polypeptides. Combinations were made of variants with the GSGSG (SEQ ID NO:5) loop, C-terminal truncation of F1, and the addition of fibritin (SEQ ID NO:4). Variants were made that contained point mutations to increase expression levels, stability and native trimeric structure. All variants were of RSV type A2, with fibritin motif, GSGSG (SEQ ID NO:5) linker; termination point 513, no HIS-tag.

According to the disclosure, the amino acid mutations that stabilize the pre-fusion conformation of the RSV F protein can be grouped into different categories that stabilize the conformation in different manners.

Amino Acid Residues 161, 173, 174, 182 and 214

In order to refold from the pre-fusion to the post-fusion conformation, the region between residues 160 and 215 has to transform from an assembly of helices, loops and strands to a long continuous helix. This region demonstrates the most dramatic structural transition. Part of this region actually has the highest alpha-helix prediction. The actual helical structures in the pre-fusion crystal structure are shown below in gray highlights. This whole region is transformed into one large helix when it refolds to the post-fusion conformation. In the bottom sequence, the residues are highlighted in gray with the highest helix prediction based on Agadir (http://agadir.crg.es/). It is clear from this comparison that the C-terminal part that is maintained in a beta-hairpin, a connecting loop and a helix in the pre-fusion conformation (residues 187-202) has a high tendency to form an alpha-helix.

```
                                                    (SEQ ID NO: 17)
150       160       170       180       190       200       210
SGVAVSKVLHLEGEVNKIKSALLSTNKAVVSLSNGVSVLTSKVLDLKNYIDKQLLPIVNKQSC

Hhhhhhhh     hhhhhhhhhh  sssssss   ssssssss   hhhhh    hhhhh

SGVAVSKVLHLEGEVNKIKSALLSTNKAVVSLSNGVSVLTSKVLDLKNYIDKQLLPIVNKQSC

Underlined residues have bad angles according to Ramachandran-plot.
```

The sequence of residues 150-212 of RSV-F is shown above. On the second line, the secondary structures of the top line are indicated by h (for helix) and s (for strands) based on the crystal structure. Helices are highlighted with gray shading. The bottom line is the same sequence in which the helices are shaded gray, based on the helix propensity of the sequence.

The regions that need optimization are the loop regions in between the secondary structural elements (helices and strands) in the labile HRA of pre-fusion RSV-F. One of the positions in HRA that needs optimization in order to stabilize the pre-fusion conformation of RSV-F is position 161 in the turn between helices α2 (residues 148-157) and α3 (residues 163-172). There are several reasons why optimization of this position could increase the stability of this region:

The turn positions the negative charge of Glu161 close to the negative charge of Glu163, resulting in destabilizing negative repulsion;

The Ramachandran plot shows that residue 161 has bad/unfavorable dihydral angles;

Residue 161 has a high B-factor that reflects high mobility (and suggests instability);

Residues 160-172 display high helix propensity.

In this example, residue Glu161 was replaced by Pro to reduce the negative repulsion and stabilize the turn and prevent it from refolding, or residue Glu161 was replaced by Gln to reduce the negative charge repulsion, or residue Glu161 was replaced by Gly because it allows a broader range of dihydral angles.

For the region of α2-turn-α3 (residues 153-168), the Brookhaven database was searched for a structurally homologous helix-turn-helix from a stable protein that does not refold in order to find a residue that could replace the unfavorable Glu161. A high structural homology was discovered with a turn in a helix-turn-helix of several proteins that all had a Proline at the homologous 161 position (PDB codes 2hgs, 3kal, 2o2z, 2zk3, and 2zqp). According to the alignment shown below, the substitution of Glu161 by Pro is a good structural solution to stabilize this turn and prevent it from refolding.

```
                                        (SEQ ID NO: 17)
    AVSKVLHLEGEVNKIK RSV-F HRA 153-168

(SEQ ID NO: 95)
    KVQQELSRPGMLEMLL 2hgs (SEQ ID NO: 96)
    KIQQELAKPGVLERFV 3kal (SEQ ID NO: 97)
    SVLPNLLVPGICEAIK 2o2z
```

-continued
```
                                        (SEQ ID NO: 17)
    avSKVLH-LEGEVNKIK RSV-F HRA 153-168

(SEQ ID NO: 98)
    ikTPLVDdLPGAEEAMS 1zk3

(SEQ ID NO: 17)
    AVSKVLH-LEGEVNKIK RSV-F HRA 153-168

(SEQ ID NO: 99)
    IMQILVTvVPALEKLSK 2zqp
```

In certain embodiments, residue Ser173 was replaced by Pro to stabilize the turn and prevent it from refolding. In certain embodiments, residue Thr174 was replaced by Pro to stabilize the turn and prevent it from refolding.

The Ramachandran plot shows that the amino acid residue 182 in the turn between β3 and β4 also has bad/unfavorable dihydral angles. Optimization of this position could increase the stability of the turn and stabilize the β-hairpin.

For the region of β3-turn-β4 (residues 177-189), the Brookhaven database was searched for a structurally homologous β-hairpin from a stable protein that does not refold in order to find a residue that could replace the unfavorable Ser182. A high structural homology was discovered with a turn in a β-hairpin of a putative electron transfer protein that had a Proline at the homologous 182 position (PDB code 3me8). According to the alignment shown below, the substitution of Ser182 by Pro is a good structural solution to stabilize this turn and prevent it from refolding.

(SEQ ID NO: 49)
AVVSISNGV-SVLT (SEQ ID NO: 100)
VVVLsPElQiKDYI

Cysteine Bridge Formation in the Bottom of the Head Region Between Residues 486, 487, and 489

The negatively charged amino acid residues 486, 487 and 489 are part of a switch mechanism that controls the transition between the pre-fusion and post-fusion RSV-F structure. Mutation of Glu487 to Gln will impair this switch and stabilize contact between the protomers in the trimer. These same residue positions can also be used to engineer disulfide bridges between the protomers. Mutations of two residues by cysteines as described above will reduce the negative charge repulsion and allow disulfide bridges that will further stabilize the pre-fusion trimer.

Variants were made that contained point mutations that stabilize the turns between the secondary structural elements in the HRA region of RSV-F pre-fusion protein to increase stability and expression levels of the pre-fusion conformation. The results are shown in Table 14.

TABLE 14

Expression and stability of A2_F24- (SEQ ID NO: 19) variants

| protein description | expression relative to A2 F24- | Stability day 5-7 | Stability day 30 |
|---|---|---|---|
| A2 F24- E161P | 2.739 | 75.08 | 66.24 |
| A2 F24- E161Q | 0.410 | 133.71 | N.A. |
| A2 F24- E161G | 0.391 | 106.42 | N.A. |
| A2 F24- S173P | 1.182 | 85.78 | N.A. |
| A2 F24- I214P | 0.288 | 80.20 | N.A. |
| A2 F24- T174P | 0.448 | 39.82 | N.A. |
| A2 F24- S182P | 2.296 | 87.19 | N.A. |
| A2 F24- N67I S215P E161P | 35.766 | 97.67 | 100.56 |
| A2 F24- N67I S215P E161Q | 9.545 | 104.40 | 96.60 |
| A2 F24- N67I S215P E161G | 12.035 | 93.70 | 81.91 |
| A2 F24- N67I S215P S173P | 21.747 | 103.43 | 71.89 |
| A2 F24- N67I S215P I214P | 8.053 | 99.47 | 68.17 |
| A2 F24- N67I S215P T174P | 5.431 | N.A. | N.A. |
| A2 F24- N67I S215P S182P | 14.948 | N.A. | N.A. |

All variants are variants of A2_F24 type A2 that contain a fibritin motif and GSGSG (SEQ ID NO: 5) linker between F1 and F2; termination point 513, (SEQ ID NO: 19).
Stability is expressed as % protein concentration measured by Q octet (Example 10) after storage at 4° C. for 5-30 days, relative to the day of harvest.
The concentrations were measured by Quantitative Octet method using CR9502 antibody.
NA: data not available: no CR9502 binding was detected.
ND: Not determined Of the single point mutations, substitution of positions 173, 182 and especially 161 to Proline resulted in higher expression levels and stability. Removing the charge of residue 161 did stabilize the proteins but did not increase expression levels. The same point mutations had a similar effect in a stabilized pre-fusion F sequence that contained the additional stabilizing N67I and S215P mutation. Mutation of residues 182, 173 and especially 161 to Proline showed the highest increase in stability and expression levels.

The E161P mutations that showed high expression and good stability of the pre-fusion conformation was also applied to soluble RSV A2 F ectodomain variants without furin cleavage site mutations (F18: SEQ ID NO:71) to evaluate whether the modifications are a universal solution to stabilize RSV pre-fusion F (Table 15).

TABLE 15

Expression and stability of variants of A2_F18 (SEQ ID NO: 71) with additional mutations

| RSV protein | SEQ ID | relative expression* | stability** after 15 days (%) |
|---|---|---|---|
| A2_F18 | 71 | 0.1 | 0.0 |
| A2_F18 N67I | | 19.6 | 29 |
| A2_F18 S215P | | 8.4 | 4 |
| A2_F18 E487Q | | 0.0 | ND |
| A2_F18 E161P | | 4.2 | 0 |
| A2_F18 N67I, S215P | 72 | 32.1 | 95 |
| A2_F18 N67I, E161P | | 34.2 | 72 |
| A2_F18 N67I, S215P, E161P | | 56.1 | 79 |
| A2_F18 N67I, S215P, E161P, E487Q | | 55.5 | 91 |
| A2_F18 N67I, S215P, E487Q | 76 | 21.8 | 95 |

Protein expression (concentration in the supernatant of transiently transfected cells) was measured by Quantitative Octet method.
*Relative expression is normalized to expression of A2_F24_N67I, S215P, E487Q (seq ID NO: 33).
**Stability—is expressed as % protein concentration measured by Q octet (Example 10) after storage at 4° C. for 5 days, relative to the day of harvest.
The concentrations were measured by Quantitative Octet method using CR9501 antibody.
ND: Not determined.

The E161P mutation also showed a high increase in expression levels in the processed RSV-F protein. When combined with stabilizing point mutations at, e.g., positions 67, 215 and 487, the E161P mutation resulted in pre-fusion F variants with high expression levels and high stability.

Cysteine Bridge Formation in the Bottom of the Head Region Between Residues 486, 487, and 489

The negatively charged amino acid residues 486, 487 and 489 are part of a switch mechanism that controls the transition between the pre-fusion and post-fusion RSV-F structure. Mutation of Glu487 to Gln will impair this switch and stabilize contact between the protomers in the trimer (previous patent P00). These same residue positions can also be used to engineer disulfide bridges between the protomers. Mutations of two residues to cysteines of which one is a negatively charged residue 486, 486 or 489, will reduce the negative charge repulsion and allow disulfide bridges that will further stabilize the pre-fusion trimer. Several of such variants were tested for expression level and stability of the pre-fusion conformation (Table 16).

TABLE 16

Expression and stability of A2_F24- (SEQ ID NO: 19) variants

| protein description | Expression relative to A2 F24- | Stability day 30 |
|---|---|---|
| A2 F24 D489C L481C | 0 | |
| A2 F24 D489C V482C | 0 | N.D. |
| A2 F24 D489C D479C | 0 | N.D. |
| A2 F24 D489C T374C | 0 | N.D. |
| A2 F24 D489C L375C | 0 | N.D. |

TABLE 16-continued

Expression and stability of A2_F24- (SEQ ID NO: 19) variants

| protein description | Expression relative to A2 F24- | Stability day 30 |
|---|---|---|
| A2 F24 D489C P376C | 0 | N.D. |
| A2 F24 D489C S377C | 0 | N.D. |
| A2 F24 D489C T335C | 0 | N.D. |
| A2 F24 D489C D338C | 0 | N.D. |
| A2 F24 D489C S398C | 0 | N.D. |
| A2 F24 D486C E487C | 0.524 | N.D. |
| A2 F24 D489C D486C | 0.062 | N.D. |
| A2 F24 N67I S215P D489C D486C | 3.875 | 76.02 |
| A2 F24 N67I S215P D489C S398C | 0.003 | N.D. |
| A2 F24 N67I S215P D486C E487C | 7.315 | 79.39 |

All variants are variants of A2_F24- type A2 that contain a fibritin motif and GSGSG (SEQ ID NO: 5) linker between F1 and F2; termination point 513, (SEQ ID NO: 19).
Stability—is expressed as % protein concentration by Q octet (Example 10) measured after storage at 4° C. for 5-30 days, relative to the day of harvest.
The concentrations were measured by Quantitative Octet method using CR9502 antibody.
ND: Not determined.

In the metastable F24 background (SEQ ID NO:19), only a disulfide bridge between residues 486 and 487 resulted in a pre-fusion protein with reasonable expression and stability. Because inter-protomeric disulfides need a correct alignment of opposing side chains, the disulfide connectivity may be more successful in a more stable F protein compared to the metastable F24 variant. Therefore, several of the disulfides were also engineered in the F24 variant that contained the two stabilizing mutations N67I and S215P. Indeed, in the stabilized background, the proteins with engineered disulfides expressed to much higher levels. Again, the variant with the cysteine mutations at positions 486 and 487 expressed to the highest level and expression level was 14 times higher compared with the unstabilized variant without the N67I and S215P mutation. Stability of the protein in the supernatant was reasonable and still contained 79% pre-fusion conformation. Higher stability may be reached when the protein is purified. Stability may not have reached 100% because not 100% of the cysteines were connected inter-protomeric as shown in Examples 4 and 5.

Example 4

Western Blotting

Culture supernatants were run reduced on 4-12% (w/v) Bis-Tris NuPAGE gels (Life Technology) and blotted using the IBLOT® technology (Life Technology). The blots were probed with CR9503 (sequences given below in Table 18) and developed with either a conjugated mouse anti-human IgG (Jackson ImmunoResearch, West Grove, Pa.) or an IRDye800CW-conjugated affinity-purified anti-human IgG (rabbit) (Rockland Immunochemicals, Gilbertsville, Pa.). In FIG. 1, the expression of DM=Double mutant (N67I+S215P=SEQ ID NO:21) and DM+CC=Double mutant+DE486CC=SEQ ID NO:94 can be seen. Clear difference between the two proteins could be observed when analyzed reduced and non-reduced. Reduced, both proteins migrate as a monomeric species around 55 kDa. Non-reduced, the vast majority of the DM is still found as a monomer while the DM+CC predominant species is much higher and predominantly trimeric. This proves that substitution of residues 486 and 487 to cysteine results in a trimer with predominantly inter-protomeric disulfide bridges.

Example 5

NativePAGE

For initial determination of the multimeric state of the pre-fusion F polypeptides according to the disclosure, culture supernatants from transiently transfected cells were analyzed in a NativePAGE Bis-Tris gel system (Life Technologies). Subsequently, the gels were blotted using the IBLOT® technology according to the manufacturer's instructions (Life Technologies). An RSV F protein-specific antibody CR9503 (sequences given below in Table 18) was used as primary probe for the detection of pre-fusion RSV F protein and followed by an HRP-conjugated mouse anti-human IgG (Jackson ImmunoResearch, West Grove, Pa.) or an IRDye800CW-conjugated affinity-purified anti-human IgG (rabbit) (Rockland Immunochemicals, Gilbertsville, Pa.). The blots were developed with either standard film (KODAK®) or using the Odyssey CLx infrared imaging system. FIG. 2 shows the NativePAGE analysis of supernatants from Lane 2: DM=Double mutant (N67I+S215P=SEQ ID NO:21) and Lane 1: DM+CC=Double mutant+DE486CC=SEQ ID NO:5. Both the DM and the DM+CC are primarily trimeric on native page, showing that the introduction of disulphides may not lead to intertrimeric cross-linking. Since the DM+CC expresses less well than the DM, the missing monomer (arrow) may be due to the fact that it is below the limit of detection.

Example 6

Expression of Pre-Fusion F Protein

Expression plasmids encoding the recombinant pre-fusion RSV F protein were generated by standard methods widely known within the art, involving site-directed mutagenesis and PCR. The expression platform used was the 293Freestyle cells (Life Technologies, Renfreshire, UK). The cells were transiently transfected using 293Fectin (Life Technologies) according to the manufacturer's instructions and cultured in a shaking incubator for 5 days at 37° C. and 10% $CO_2$. The culture supernatant was harvested and spun for 5 minutes at 300 g to remove cells and cellular debris. The spun supernatant was subsequently sterile filtered using a 0.22 μm vacuum filter and stored at 4° C. until use.

Example 7

Purification of Pre-Fusion RSV F Protein

The recombinant polypeptides were purified by a two-step purification protocol applying a cat-ion exchange column for the initial purification and subsequently a SUPERDEX® 200 column for the polishing step to remove residual contaminants. For the initial ion-exchange step, the culture supernatant was diluted with 2 volumes of 50 mM NaOAc pH 5.0 and passed over a 5 ml HiTrap Capto S column at 5 ml per minute. Subsequently, the column was washed with 10 column volumes (CV) of 20 mM NaOAc, 50 mM NaCl, 0.01% (v/v) TWEEN® 20, pH 5 and eluted 2 CV of 20 mM NaOAc, I M NaCl, 0.01% (v/v) TWEEN® 20, pH 5. The eluate was concentrated using a spin concentrator and the protein was further purified using a SUPERDEX® 200 column using 40 mM Tris, 500 mM NaCl, 0.01% (v/v) TWEEN® 20, pH 7.4 as running buffer. In FIG. 3A, the chromatogram from the gel filtration column is shown and the dominant peak contains the pre-fusion RSV F protein.

The fractions containing this peak were again pooled and the protein concentration was determined using OD280 and stored at 4° C. until use. In FIG. 3B, a reduced SDS-PAGE analysis of the final protein preparation is shown and, as can be seen, the purity was >95%. The identity of the band was verified using Western blotting and protein F-specific antibodies (not shown). Next, the purified protein was tested on NativePAGE and compared with a reference stable trimeric pre-fusion F protein (SEQ ID NO:21) (FIG. 3C).

Example 8

Endpoint Stability Assay

The verification of the pre-fusion conformation of the expressed polypeptides according to the disclosure was done using the octet technology using the pre-fusion-specific antibodies CR9501 or CR9502, or the non-conformation-specific antibody CR9503, which comprises the heavy and light chain variable regions of the commercially available antibody Motavizumab. The antibodies were biotinylated by standard protocols and immobilized on streptavidin biosensors (FORTEBIO®, Portsmouth, UK). The procedure was as follows. After equilibration of the sensors in kinetic buffer (FORTEBIO®) for 60 seconds, the chips were transferred to PBS with 5 µg/ml of the desired antibody. The loading was carried out for 250 seconds. Subsequently, another equilibration step was included for 200 seconds in kinetic buffer. Lastly, the chips were transferred to the expression culture supernatant containing the pre-fusion RSV F polypeptides and the total binding signal after 1200 seconds was recorded. This phase is also referred to as the association phase. This was done immediately after harvest (day 1) as well as 5 days later (day 5) and the difference in the CR9501 binding was used as a screening tool to identify mutations capable of stabilizing the pre-fusion conformation. A construct was deemed stable if less than 20% loss of binding was observed at day 5 and, if not, it was deemed unstable. Stable constructs could then undergo a more stringent stability test if needed. The data analysis was done using the FORTEBIO® Data Analysis 6.4 software (FORTEBIO®).

Example 9

Heat Stability Assay

The stabilizing potential of introduced features into the RSV F polypeptides was estimated by heat stress. For that purpose, culture supernatant from transiently transfected cells or purified protein was heated using a range of temperatures. The samples were subsequently cooled on ice to prevent further heat-induced conformational changes and probed using the CR9501 antibody on the octet technology platform as described in Example 11. The responses obtained at the end of the association phase at the different temperatures were plotted as a function of the temperature and fitted by non-linear regression using the Prism software. This resulted in an estimation of the temperature where the antibody binding level is 50% of the maximum and this value could be used to compare different constructs in terms of pre-fusion heat stability.

Example 10

Association Phase Stability Assay

To assess the stability of various point mutations, the octet binding assay was developed by using association phase analysis. The CR9501 antibody or CR9502 antibody was used as probes for the pre-fusion conformation of the RSV-F protein. To reduce potential concentration bias of the endpoint assay, the data points were used from the entire association phase of the experiment. The data were compensated for the amount of bound antibody on the chip. The measurements were done at days 1, 5 and 33, and the shapes of the curves from the three days were compared. If identical curves were obtained, the construct was deemed stable and, if not, unstable.

Example 11

Quantitative Octet

To measure concentration of the pre-fusion RSV F protein in cell culture supernatants, quantitative Octet-based method was used. The CR9501 and CR9503 antibodies were biotinylated by standard protocols and immobilized on Streptavidin biosensors (FORTEBIO®, Portsmouth, UK). Afterwards, the coated biosensors were blocked in mock cell culture supernatant. Quantitative experiment was performed as follows: temperature 30° C., shaking speed 1000 rpm, time of the assay 300 seconds. Concentration of the protein in the cell culture supernatant was calculated using standard curve. The standard curve was prepared for each coated antibody using the A2_F24 N67I+S215P (SEQ NO:21) protein, diluted in mock cell culture supernatant. The measurement was done on the day of supernatant harvest (day 1) and after storage of the supernatant at 4° C. for 5 days or longer. The difference in the concentration determined with the CR9501 or CR9502 was used as a screening tool to identify mutations capable of stabilizing the pre-fusion conformation. A construct was deemed stable if less than 20% decrease of measured concentration was observed at day 5. The data analysis was done using the FORTEBIO® Data Analysis 6.4 software (FORTEBIO®).

Example 12

Preclinical Evaluation of Pre-Fusion F Immunogenicity

To evaluate the immunogenicity of a stabilized pre-fusion RSV F (A2F24, N67I, S215P) (SEQ ID NO:21), mice were immunized according to Table 19 with 0.5 or 5 µg in a prime—boost regimen at week 0 and week 4. As shown in FIG. 4, mice immunized with pre-fusion F showed higher VNA titers than mice immunized with post-fusion RSV F.

TABLE 19

Immunization scheme

| Group | Preparation | Dose | Adjuvant | N |
|---|---|---|---|---|
| 1 | Post-fusion F | 0.5 µg | — | 9 |
| 2 | Post-fusion F | 5 µg | — | 9 |
| 3 | Pre-fusion F | 0.5 µg | — | 9 |
| 4 | Pre-fusion F | 5 µg | — | 9 |
| 5 | Post-fusion F | 0.5 µg | Poly(I:C) | 9 |
| 6 | Pre-fusion F | 0.5 µg | Poly(I:C) | 9 |
| 8 | FI-RSV | 1/75 | — | 8 |
| 9 | PBS | | — | 3 |

Next, cotton rats were immunized with two different doses of RSV-F in either the post-fusion or the pre-fusion conformation (Table 20). Animals were immunized i.m. at week 0 and week 4. FIG. 5 demonstrates high neutralizing antibody titers at the day of challenge (week 7).

TABLE 20

Groups, immunogen and dose for immunogenicity evaluation and efficacy in cotton rats

| Group | Preparation | Dose | Adjuvant |
|---|---|---|---|
| 1 | Post-fusion F | 0.5 μg | — |
| 2 | Post-fusion F | 5 μg | — |
| 3 | Pre-fusion F | 0.5 μg | — |
| 4 | Pre-fusion F | 5 μg | — |
| 9 | Pre-fusion F | 0.5 μg | Poly IC |
| 10 | Pre-fusion F | 5 μg | Poly IC |
| 11 | Pre-fusion F | 0.5 μg | Adju Phos |
| 12 | Pre-fusion F | 5 μg | Adju Phos |
| 13 | Ad26.RSV.F$_{A2}$ | $10^8$ | — |
| 14 | PBS | — | — |

Five days after challenge, the lung and nose viral load was measured (see FIG. 6).

As shown, the pre-fusion F polypeptides according to the disclosure are able to induce a strong protective immune response that reduced viral load in the lung and even in the nose.

TABLE 17

Standard amino acids, abbreviations and properties

| Amino Acid | 3-Letter | 1-Letter | Side chain polarity | Side chain charge (pH 7.4) |
|---|---|---|---|---|
| alanine | Ala | A | non-polar | Neutral |
| arginine | Arg | R | polar | Positive |
| asparagine | Asn | N | polar | Neutral |
| aspartic acid | Asp | D | polar | Negative |
| cysteine | Cys | C | non-polar | Neutral |
| glutamic acid | Glu | E | polar | Negative |
| glutamine | Gln | Q | polar | Neutral |
| glycine | Gly | G | non-polar | Neutral |
| histidine | His | H | polar | positive (10%) neutral (90%) |
| isoleucine | Ile | I | non-polar | Neutral |
| leucine | Leu | L | non-polar | Neutral |
| lysine | Lys | K | polar | Positive |
| methionine | Met | M | non-polar | Neutral |
| phenylalanine | Phe | F | non-polar | Neutral |
| proline | Pro | P | non-polar | Neutral |
| serine | Ser | S | polar | Neutral |
| threonine | Thr | T | polar | Neutral |
| tryptophan | Trp | W | non-polar | Neutral |
| tyrosine | Tyr | Y | polar | Neutral |
| valine | Val | V | non-polar | Neutral |

TABLE 18

Amino acid sequences of antibodies CR9501 and CR9502

| Ab | VH domain | VH CDR1 | VH CDR2 | VH CDR3 |
|---|---|---|---|---|
| CR9501 | Amino acids 1-125 of SEQ ID NO: 53 | GASINSDNYYWT (SEQ ID NO: 54) | HISYTGNTYYTPSLKS (SEQ ID NO: 55) | CGAYVLISNCGWFDS (SEQ ID NO: 56) |
| CR9502 | Amino acids 1-121 of SEQ ID NO: 57 | GFTFSGHTIA (SEQ ID NO: 58) | WVSTNNGNTEYAQKIQG (SEQ ID NO: 59) | EWLVMGGFAFDH (SEQ ID NO: 60) |

| Ab | VL domain | VL CDR1 | VL CDR2 | VL CDR3 |
|---|---|---|---|---|
| CR9501 | Amino acids 1-107 of SEQ ID NO: 61 | QASQDISTYLN (SEQ ID NO: 62) | GASNLET (SEQ ID NO: 63) | QQYQYLPYT (SEQ ID NO: 64) |
| CR9502 | Amino acids 1-110 of SEQ ID NO: 65 | GANNIGSQNVH (SEQ ID NO: 66) | DDRDRPS (SEQ ID NO: 67) | QVWDSSRDQAVI (SEQ ID NO: 68) |

The amino acid sequence of several of the pre-fusion RSV F constructs is given below. It is noted that the amino acid numbering in the different constructs described herein is based on the wild-type sequence (SEQ ID NO:1), which means that all amino acids from position 1 to and including position 108 of the pre-fusion constructs correspond to the amino acid positions 1-108 of the wild-type sequence, whereas the numbering of the amino acids from position 138 to the end is shifted 22 amino acids, i.e., L138 in the wild-type sequence (SEQ ID NO:1) corresponds to L116 in all the pre-fusion constructs. This is due to the fact that a deletion has been made in the pre-fusion constructs, i.e., in the insertion of the GSGSG (SEQ ID NO:5) linker, the actual numbering in F1 is not the same between constructs. Thus, the numbering used with respect to the specific mutations according to the disclosure, e.g., S215P, refers to the position of the amino acid in the wild-type sequence.

Sequences

RSV F protein A2 full-length sequence (SEQ ID NO: 1)
MELLILKANAITTILTAVTFCFASGQNITEEFYQSTCSAVSKGYLSALRTGWYTSVITIELS
NIKKNKCNGTDAKIKLIKQELDKYKNAVTELQLLMQSTPATNNRARRELPRFMNYTLN

| Sequences |
|---|
| NAKKTNVTLSKKRKRRFLGFLLGVGSAIASGVAVSKVLHLEGEVNKIKSALLSTNKAVV
SLSNGVSVLTSKVLDLKNYIDKQLLPIVNKQSCSISNIETVIEFQQKNNRLLEITREFSVNA
GVTTPVSTYMLTNSELLSLINDMPITNDQKKLMSNNVQIVRQQSYSIMSIIKEEVLAYVV
QLPLYGVIDTPCWKLHTSPLCTTNTKEGSNICLTRTDRGWYCDNAGSVSFFPQAETCKV
QSNRVFCDTMNSLTLPSEVNLCNVDIFNPKYDCKIMTSKTDVSSSVITSLGAIVSCYGKT
KCTASNKNRGIIKTFSNGCDYVSNKGVDTSVGNTLYYVNKQEGKSLYVKGEPIINFYD
PLVFPSDEFDASISQVNEKINQSLAFIRKSDELLHNVAVKSTTNIMITTIIIVIIVILLSLIAV
GLLLYCKARSTPVTLSKDQLSGINNIAFSN RSV F protein B1 full-length sequence
(SEQ ID NO: 2)
MELLIHRLSAIFLTLAINALYLTSSQNITEEFYQSTCSAVSRGYFSALRTGWYTSVITIELS
NIKETKCNGTDTKVKLIQELDKYKNAVTELQLLMQNTPAANNRARREAPQYMNYTIN
TTKNLNVSISKKRKRRFLGFLLGVGSAIASGIAVSKVLHLEGEVNKIKNALLSTNKAVVS
LSNGVSVLTSKVLDLKNYINNQLLPIVNQQSCRISNIETVIEFQQKNSRLLEINREFSVNAG
VTTPLSTYMLTNSELLSLINDMPITNDQKKLMSSNVQIVRQQSYSIMSIIKEEVLAYVVQL
PIYGVIDTPCWKLHTSPLCTTNIKEGSNICLTRTDRGWYCDNAGSVSFFPQADTCKVQSN
RVFCDTMNSLTLPSEVSLCNTDIFNSKYDCKIMTSKTDISSSVITSLGAIVSCYGKTKCTA
SNKNRGIIKTFSNGCDYVSNKGVDTSVGNTLYYVNKLEGKNLYVKGEPIINYYDPLVF
PSDEFDASISQVNEKINQSLAFIRRSDELLHNVTGKSTTNIMITTIIIVIIVVLLSLIAIGLLL
YCKAKNTPVTLSKDQLSGINNIAFSK

SEQ ID NO: 3
EKKIEAIEKKIEAIEKKIEA

SEQ ID NO: 4
GYIPEAPRDGQAYVRKDGEWVLLSTFL

SEQ ID NO: 5
GSGSG

F8: RSV A2, wt ectodomain
(SEQ ID NO: 13)
MELLILKANAITTILTAVTFCFASGQNITEEFYQSTCSAVSKGYLSALRTGWYTSVITIELS
NIKKNKCNGTDAKIKLIQELDKYKNAVTELQLLMQSTPATNNRARRELPRFMNYTLN
NAKKTNVTLSKKRKRRFLGFLLGVGSAIASGVAVSKVLHLEGEVNKIKSALLSTNKAVV
SLSNGVSVLTSKVLDLKNYIDKQLLPIVNKQSCSISNIETVIEFQQKNNRLLEITREFSVNA
GVTTPVSTYMLTNSELLSLINDMPITNDQKKLMSNNVQIVRQQSYSIMSIIKEEVLAYVV
QLPLYGVIDTPCWKLHTSPLCTTNTKEGSNICLTRTDRGWYCDNAGSVSFFPQAETCKV
QSNRVFCDTMNSLTLPSEVNLCNVDIFNPKYDCKIMTSKTDVSSSVITSLGAIVSCYGKT
KCTASNKNRGIIKTFSNGCDYVSNKGVDTSVGNTLYYVNKQEGKSLYVKGEPIINFYD
PLVFPSDEFDASISQVNEKINQSLAFIRKSDELLHHHHHHH F11: RSV B1, wt ectodomain
(SEQ ID NO: 14)
MELLIHRLSAIFLTLAINALYLTSSQNITEEFYQSTCSAVSRGYFSALRTGWYTSVITIELS
NIKETKCNGTDTKVKLIQELDKYKNAVTELQLLMQNTPAANNRARREAPQYMNYTIN
TTKNLNVSISKKRKRRFLGFLLGVGSAIASGIAVSKVLHLEGEVNKIKNALLSTNKAVVS
LSNGVSVLTSKVLDLKNYINNQLLPIVNQQSCRISNIETVIEFQQKNSRLLEINREFSVNAG
VTTPLSTYMLTNSELLSLINDMPITNDQKKLMSSNVQIVRQQSYSIMSIIKEEVLAYVVQL
PIYGVIDTPCWKLHTSPLCTTNIKEGSNICLTRTDRGWYCDNAGSVSFFPQADTCKVQSN
RVFCDTMNSLTLPSEVSLCNTDIFNSKYDCKIMTSKTDISSSVITSLGAIVSCYGKTKCTA
SNKNRGIIKTFSNGCDYVSNKGVDTSVGNTLYYVNKLEGKNLYVKGEPIINYYDPLVF
PSDEFDASISQVNEKINQSLAFIRRSDELLHHHHHHH F47: RSV A2, linker stabilized, IZ(S)
(SEQ ID NO: 15)
MELLILKANAITTILTAVTFCFASGQNITEEFYQSTCSAVSKGYLSALRTGWYTSVITIELS
NIKKNKCNGTDAKIKLIQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSISNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTSVGNTLYYVNKQEGKSLYVKGEPIINFYDPLVFPSDEFDASISQVEKKIEAIEK
KIEAIEKKIEAGGIEGRHHHHHHH F47-: RSV A2, linker stabilized, IZ(S)
(SEQ ID NO: 16)
MELLILKANAITTILTAVTFCFASGQNITEEFYQSTCSAVSKGYLSALRTGWYTSVITIELS
NIKKNKCNGTDAKIKLIQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSISNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN |

| Sequences |
|---|

KGVDTVSVGNTLYYVNKQEGKSLYVKGEPIINFYDPLVFPSDEFDASISQVEKKIEAIEK
KIEAIEKKIEAGG

F43: RSV B1, linker stabilized, IZ(S)

(SEQ ID NO: 17)

MELLIHRLSAIFLTLAINALYLTSSQNITEEFYQSTCSAVSRGYFSALRTGWYTSVITIELS
NIKETKCNGTDTKVKLIKQELDKYKNAVTELQLLMQNTPAANNQARGSGSGRSLGFLL
GVGSAIASGIAVSKVLHLEGEVNKIKNALLSTNKAVVSLSNGVSVLTSKVLDLKNYINN
QLLPIVNQQSCRISNIETVIEFQQKNSRLLEINREFSVNAGVTTPLSTYMLTNSELLSLIND
MPITNDQKKLMSSNVQIVRQQSYSIMSIIKEEVLAYVVQLPIYGVIDTPCWKLHTSPLCTT
NIKEGSNICLTRTDRGWYCDNAGSVSFFPQADICKVQSNRVFCDTMNSLTLPSEVSLCN
TDIFNSKYDCKIMTSKTDISSSVITSLGAIVSCYGKTKCTASNKNRGIIKTFSNGCDYVSN
KGVDTVSVGNTLYYVNKLEGKNLYVKGEPIINYYDPLVFPSDEFDASISQVEKKIEAIEK
KIEAIEKKIEAGGIEGRHHHHHH

F24: RSV B1, linker stabilized, fibritin (SEQ ID NO: 18)

MELLIHRLSAIFLTLAINALYLTSSQNITEEFYQSTCSAVSRGYFSALRTGWYTSVITIELS
NIKETKCNGTDTKVKLIKQELDKYKNAVTELQLLMQNTPAANNQARGSGSGRSLGFLL
GVGSAIASGIAVSKVLHLEGEVNKIKNALLSTNKAVVSLSNGVSVLTSKVLDLKNYINN
QLLPIVNQQSCRISNIETVIEFQQKNSRLLEINREFSVNAGVTTPLSTYMLTNSELLSLIND
MPITNDQKKLMSSNVQIVRQQSYSIMSIIKEEVLAYVVQLPIYGVIDTPCWKLHTSPLCTT
NIKEGSNICLTRTDRGWYCDNAGSVSFFPQADTCKVQSNRVFCDTMNSLTLPSEVSLCN
TDIFNSKYDCKIMTSKTDISSSVITSLGAIVSCYGKTKCTASNKNRGIIKTFSNGCDYVSN
KGVDTVSVGNTLYYVNKLEGKNLYVKGEPIINYYDPLVFPSDEFDASISQVNEKINQSLA
FIRRSDELLSAIGGYIPEAPRDGQAYVRKDGEWVLLSTFLGGIEGRHHHHHH

A2_F24: RSV A2, linker stabilized, fibritin (SEQ ID NO: 19)

MELLILKANAITTILTAVTFCFASGQNITEEFYQSTCSAVSKGYLSALRTGWYTSVITIELS
NIKKNKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSISNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR

F24-: RSV B1, linker stabilized, fibritin (SEQ ID NO: 20)

MELLIHRLSAIFLTLAINALYLTSSQNITEEFYQSTCSAVSRGYFSALRTGWYTSVITIELS
NIKETKCNGTDTKVKLIKQELDKYKNAVTELQLLMQNTPAANNQARGSGSGRSLGFLL
GVGSAIASGIAVSKVLHLEGEVNKIKNALLSTNKAVVSLSNGVSVLTSKVLDLKNYINN
QLLPIVNQQSCRISNIETVIEFQQKNSRLLEINREFSVNAGVTTPLSTYMLTNSELLSLIND
MPITNDQKKLMSSNVQIVRQQSYSIMSIIKEEVLAYVVQLPIYGVIDTPCWKLHTSPLCTT
NIKEGSNICLTRTDRGWYCDNAGSVSFFPQADTCKVQSNRVFCDTMNSLTLPSEVSLCN
TDIFNSKYDCKIMTSKTDISSSVITSLGAIVSCYGKTKCTASNKNRGIIKTFSNGCDYVSN
KGVDTVSVGNTLYYVNKLEGKNLYVKGEPIINYYDPLVFPSDEFDASISQVNEKINQSLA
FIRRSDELLSAIGGYIPEAPRDGQAYVRKDGEWVLLSTFLGGIEGR

A2_F24 N67I + S215P: A2, linker stabilized, fibritin (SEQ ID NO: 21)

MELLILKANAITTILTAVTFCFASGQNITEEFYQSTCSAVSKGYLSALRTGWYTSVITIELS
NIKK<u>I</u>KCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSI<u>P</u>NIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR

F24-N67I + S215P: RSV B1, linker stabilized, fibritin (SEQ ID NO: 22)

MELLIHRLSAIFLTLAINALYLTSSQNITEEFYQSTCSAVSRGYFSALRTGWYTSVITIELS
NIKE<u>I</u>KCNGTDTKVKLIKQELDKYKNAVTELQLLMQNTPAANNQARGSGSGRSLGFLLG
VGSAIASGIAVSKVLHLEGEVNKIKNALLSTNKAVVSLSNGVSVLTSKVLDLKNYINNQ
LPIVNQQSCRI<u>P</u>NIETVIEFQQKNSRLLEINREFSVNAGVTTPLSTYMLTNSELLSLINDMPI
TNDQKKLMSSNVQIVRQQSYSIMSIIKEEVLAYVVQLPIYGVIDTPCWKLHTSPLCTTNIK
EGSNICLTRTDRGWYCDNAGSVSFFPQADTCKVQSNRVFCDTMNSLTLPSEVSLCNTDI
FNSKYDCKIMTSKTDISSSVITSLGAIVSCYGKTKCTASNKNRGIIKTFSNGCDYVSNKGV
DTVSVGNTLYYVNKLEGKNLYVKGEPIINYYDPLVFPSDEFDASISQVNEKINQSLAFIRR
SDELLSAIGGYIPEAPRDGQAYVRKDGEWVLLSTFLGGIEGR

| Sequences |
| --- |

A2_F24 N67I + E92D: RSV A2, linker stabilized, fibritin
(SEQ ID NO: 23)
MELLILKANAITTILTAVTFCFASGQNITEEFYQSTCSAVSKGYLSALRTGWYTSVITIELS
NIKKIKCNGTDAKIKLIKQELDKYKNAVTDLQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSISNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPUNFYDPLVFPSDEFDASISQVNEKINQSLA
FIRKSDELLSAIGGYIPEAPRDGQAYVRKDGEWVLLSTFLGGIEGR F24- N67I + E92D RSV B1, linker stabilized, fibritin
(SEQ ID NO: 24)
MELLIHRLSAIFLTLAINALYLTSSQNITEEFYQSTCSAVSRGYFSALRTGWYTSVITIELS
NIKEIKCNGTDTKVKLIKQELDKYKNAVTDLQLLMQNTPAANNQARGSGSGRSLGFLL
GVGSAIASGIAVSKVLHLEGEVNKIKNALLSTNKAVVSLSNGVSVLTSKVLDLKNYINN
QLLPIVNQQSCRISNIETVIEFQQKNSRLLEINREFSVNAGVTTPLSTYMLTNSELLSLIND
MPITNDQKKLMSSNVQIVRQQSYSIMSIIKEEVLAYVVQLPIYGVIDTPCWKLHTSPLCTT
NIKEGSNICLTRTDRGWYCDNAGSVSFFPQADTCKVQSNRVFCDTMNSLTLPSEVSLCN
TDIFNSKYDCKIMTSKTDISSSVITSLGAIVSCYGKTKCTASNKNRGIIKTFSNGCDYVSN
KGVDTVSVGNTLYYVNKLEGKNLYVKGEPIINYYDPLVFPSDEFDASISQVNEKINQSLA
FIRRSDELLSAIGGYIPEAPRDGQAYVRKDGEWVLLSTFLGGIEGR A2_F24 N67I + K465Q RSV A2, linker stabilized, fibritin
(SEQ ID NO: 25)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGQSLYVKGEPIINFYDPLVFPSDEFDASISQVNEKINQSLA
FIRKSDELLSAIGGYIPEAPRDGQAYVRKDGEWVLLSTFLGGIEGR F24- N67I + K465Q RSV B1, linker stabilized, fibritin
(SEQ ID NO: 26)
MELLIHRLSAIFLTLAINALYLTSSQNITEEFYQSTCSAVSRGYFSALRTGWYTSVITIELS
NIKEIKCNGTDTKVKLIKQELDKYKNAVTELQLLMQNTPAANNQARGSGSGRSLGFLLG
VGSAIASGIAVSKVLHLEGEVNKIKNALLSTNKAVVSLSNGVSVLTSKVLDLKNYINNQL
LPIVNQQSCRIPNIETVIEFQQKNSRLLEINREFSVNAGVTTPLSTYMLTNSELLSLINDMPI
TNDQKKLMSSNVQIVRQQSYSIMSIIKEEVLAYVVQLPIYGVIDTPCWKLHTSPLCTTNIK
EGSNICLTRTDRGWYCDNAGSVSFFPQADTCKVQSNRVFCDTMNSLTLPSEVSLCNTDI
FNSKYDCKIMTSKTDISSSVITSLGAIVSCYGKTKCTASNKNRGIIKTFSNGCDYVSNKGV
DTVSVGNTLYYVNKLEGQNLYVKGEPIINYYDPLVFPSDEFDASISQVNEKINQSLAFIRR
SDELLSAIGGYIPEAPRDGQAYVRKDGEWVLLSTFLGGIEGR A2_F24 N67I + S46G RSV A2, linker stabilized, fibritin
(SEQ ID NO: 27)
MELLILKANAITTILTAVTFCFASGQNITEEFYQSTCSAVSKGYLGALRTGWYTSVITIELS
NIKKIKCNGTDAKIKLIKQELDKYKNAVTDLQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSISNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR F24- N67I + S46G RSV B1, linker stabilized, fibritin
(SEQ ID NO: 28)
MELLIHRLSAIFLTLAINALYLTSSQNITEEFYQSTCSAVSRGYFGALRTGWYTSVITIELS
NIKEIKCNGTDTKVKLIKQELDKYKNAVTDLQLLMQNTPAANNQARGSGSGRSLGFLL
GVGSAIASGIAVSKVLHLEGEVNKIKNALLSTNKAVVSLSNGVSVLTSKVLDLKNYINN
QLLPIVNQQSCRISNIETVIEFQQKNSRLLEINREFSVNAGVTTPLSTYMLTNSELLSLIND
MPITNDQKKLMSSNVQIVRQQSYSIMSIIKEEVLAYVVQLPIYGVIDTPCWKLHTSPLCTT
NIKEGSNICLTRTDRGWYCDNAGSVSFFPQADTCKVQSNRVFCDTMNSLTLPSEVSLCN
TDIFNSKYDCKIMTSKTDISSSVITSLGAIVSCYGKTKCTASNKNRGIIKTFSNGCDYVSN
KGVDTVSVGNTLYYVNKLEGKNLYVKGEPIINYYDPLVFPSDEFDASISQVNEKINQSLA
FIRRSDELLSAIGGYIPEAPRDGQAYVRKDGEWVLLSTFLGGIEGR A2_F24 E92D + S215P: A2, linker stabilized, fibritin
(SEQ ID NO: 29)
MELLILKANAITTILTAVTFCFASGQNITEEFYQSTCSAVSKGYLSALRTGWYTSVITIELS
NIKKNKCNGTDAKIKLIKQELDKYKNAVTDLQLLMQSTPATNNQARGSGSGRSLGFLLG
VGSAIASGVAVSKVLHLEGEVNKIKSALLSTNKAVVSLSNGVSVLTSKVLDLKNYIDKQ

```
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR

F24-E92D + S215P: RSV B1, linker stabilized, fibritin
                                                      (SEQ ID NO: 30)
MELLIHRLSAIFLTLAINALYLTSSQNITEEFYQSTCSAVSRGYFSALRTGWYTSVITIELS
NIKETKCNGTDTKVKLIKQELDKYKNAVTDLQLLMQNTPAANNQARGSGSGRSLGFLL
GVGSAIASGIAVSKVLHLEGEVNKIKNALLSTNKAVVSLSNGVSVLTSKVLDLKNYINN
QLLPIVNQQSCSRIPNIETVIEFQQKNSRLLEINREFSVNAGVTTPLSTYMLTNSELLSIND
MPITNDQKKLMSNNVQIVRQQSYSIMSIIKEEVLAYVVQLPIYGVIDTPCWKLHTSPLCTT
NIKEGSNICLTRTDRGWYCDNAGSVSFFPQADTCKVQSNRVFCDTMNSLTLPSEVSLCN
TDIFNSKYDCKIMTSKTDISSSVITSLGAIVSCYGKTKCTASNKNRGIIKTFSNGCDYVSN
KGVDTVSVGNTLYYVNKLEGKNLYVKGEPIINYYDPLVFPSDEFDASISQVNEKINQSLA
FIRRSDELLSAIGGYIPEAPRDGQAYVRKDGEWVLLSTFLGGIEGR A2_F24 N67I + S215P + K508E: A2, linker stabilized, fibritin
                                                      (SEQ ID NO: 31)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRESDELLSAIGGYIPEAPRDGQAYVRKDGEWVLLSTFLGGIEGR A2_F24 N67I + S215P + E487I: A2, linker stabilized, fibritin
                                                      (SEQ ID NO: 32)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDIFDASISQVNEKINQSLAF
IRKSDELLSAIGGYIPEAPRDGQAYVRKDGEWVLLSTFLGGIEGR A2_F24 N67I + S215P + E487Q: A2, linker stabilized, fibritin
                                                      (SEQ ID NO: 33)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDQFDASISQVNEKINQSLA
FIRKSDELLSAIGGYIPEAPRDGQAYVRKDGEWVLLSTFLGGIEGR A2_F24 N67I + S215P + E487N: A2, linker stabilized, fibritin
                                                      (SEQ ID NO: 34)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDNFDASISQVNEKINQSLA
FIRKSDELLSAIGGYIPEAPRDGQAYVRKDGEWVLLSTFLGGIEGR A2_F24 N67I + S215P + D486N: A2, linker stabilized, fibritin
                                                      (SEQ ID NO: 35)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
```

-continued

Sequences

KGVDTVSVGNTLYYVNKQEGKSLYVKGEPIINFYDPLVFPSNEFDASISQVNEKINQSLA
FIRKSDELLSAIGGYIPEAPRDGQAYVRKDGEWVLLSTFLGGIEGR

A2_F24 N67I + S215P + K465E: A2, linker stabilized, fibritin
(SEQ ID NO: 36)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGESLYVKGEPIINFYDPLVFPSDEFDASISQVNEKINQSLA
FIRKSDELLSAIGGYIPEAPRDGQAYVRKDGEWVLLSTFLGGIEGR A2_F24 N67I + S215P + K465Q: A2, linker stabilized, fibritin
(SEQ ID NO: 37)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGQSLYVKGEPIINFYDPLVFPSDEFDASISQVNEKINQSLA
FIRKSDELLSAIGGYIPEAPRDGQAYVRKDGEWVLLSTFLGGIEGR A2_F24 N67I + S215P + N426S: A2, linker stabilized, fibritin
(SEQ ID NO: 38)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASSKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR A2_F24 N67I + S215P + K421N: A2, linker stabilized, fibritin
(SEQ ID NO: 39)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTNCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR A2_F24 N67I + S215P + K209Q: A2, linker stabilized, fibritin
(SEQ ID NO: 40)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNQQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR A2_F24 N67I + S215P + K201Q: A2, linker stabilized, fibritin
(SEQ ID NO: 41)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDQQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR

| Sequences |
| --- |

A2_F24 N67I + S215P + V185N: A2, linker stabilized, fibritin
(SEQ ID NO: 42)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGNSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCIASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR A2_F24 N67I + S215P + G184N: A2, linker stabilized, fibritin
(SEQ ID NO: 43)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNNVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR A2_F24 N67I + S215P + N175P: A2, linker stabilized, fibritin
(SEQ ID NO: 44)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTPKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR A2_F24 N67I + S215P + E92D: A2, linker stabilized, fibritin
(SEQ ID NO: 45)
MELLILKANAITTILTAVTFCFASGQNITEEFYQSTCSAVSKGYLSALRTGWYTSVITIELS
NIKKIKCNGTDAKIKLIKQELDKYKNAVTDLQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR A2_F24 N67I + S215P + K80E: A2, linker stabilized, fibritin
(SEQ ID NO: 46)
MELLILKANAITTILTAVTFCFASGQNITEEFYQSTCSAVSKGYLSALRTGWYTSVITIELS
NIKKIKCNGTDAKIKLIEQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR A2_F24 N67I + S215P + K77E: A2, linker stabilized, fibritin
(SEQ ID NO: 47)
MELLILKANAITTILTAVTFCFASGQNITEEFYQSTCSAVSKGYLSALRTGWYTSVITIELS
NIKKIKCNGTDAKIELIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR A2_F24 N67I + S215P + S46G: A2, linker stabilized, fibritin
(SEQ ID NO: 48)
MELLILKANAITTILTAVTFCFASGQNITEEFYQSTCSAVSKGYLGALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ

| Sequences |
|---|
| LLPIVNKQSCSI<u>PN</u>IETVIEFQQKNNRLLEITREFSVNAGVTTPVSTYMLTNSELLSLINDM<br>PITNDQKKLMSNNVQIVRQQSYSIMSIIKEEVLAYVVQLPLYGVIDTPCWKLHTSPLCTT<br>NTKEGSNICLTRTDRGWYCDNAGSVSFFPQAETCKVQSNRVFCDTMNSLTLPSEVNLCN<br>VDIFNPKYDCKIMTSKTDVSSSVITSLGAIVSCYGKTKCTASNKNRGIIKTFSNGCDYVSN<br>KGVDTVSVGNTLYYVNKQEGKSLYVKGEPIINFYDPLVFPSDEFDASISQVNEKINQSLA<br>FIRKSDELLSAIGGYIPEAPRDGQAYVRKDGEWVLLSTFLGGIEGR |

A2_F24: RSV S46G A2, linker stabilized, fibritin (SEQ ID NO: 49)

MELLILKANAITTILTAVTFCFASGQNITEEFYQSTCSAVSKGYL<u>G</u>ALRTGWYTSVITIELS
NIKKNKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSISNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR

A2_F24: RSV K465Q A2, linker stabilized, fibritin (SEQ ID NO: 50)

MELLILKANAITTILTAVTFCFASGQNITEEFYQSTCSAVSKGYLSALRTGWYTSVITIELS
NIKKNKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSISNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEG<u>Q</u>SLYVKGEPIINFYDPLVFPSDEFDASISQVNEKINQSLA
FIRKSDELLSAIGGYIPEAPRDGQAYVRKDGEWVLLSTFLGGIEGR

A2_F24: RSV N67I A2, linker stabilized, fibritin (SEQ ID NO: 51)

MELLILKANAITTILTAVTFCFASGQNITEEFYQSTCSAVSKGYLSALRTGWYTSVITIELS
NIKK<u>I</u>KCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSISNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR

A2_F24: RSV E92D A2, linker stabilized, fibritin (SEQ ID NO: 52)

MELLILKANAITTILTAVTFCFASGQNITEEFYQSTCSAVSKGYLSALRTGWYTSVITIELS
NIKKNKCNGTDAKIKLIKQELDKYKNAVT<u>D</u>LQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSISNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLSAIGGYIPEAPRDGQAYVRKDGEWVLLSTFLGGIEGR

RSV F protein CL57-v224 full-length sequence (SEQ ID NO: 69)

MELPILKTNAITTILAAVTLCFASSQNITEEFYQSTCSAVSKGYLSALRTGWYTSVITIELS
NIKENKCNGTDAKVKLIKQELDKYKNAVTELQLLMQSTPAANNRARRELPRFMNYTLN
NTKNNNVTLSKKRKRRFLGFLLGVGSAIASGIAVSKVLHLEGEVNKIKSALLSTNKAVV
SLSNGVSVLTSKVLDLKNYIDKQLLPIVNKQSCSISNIETVIEFQQKNNRLLEITREFSVNA
GVTTPVSTYMLTNSELLSLINDMPITNDQKKLMSNNVQIVRQQSYSIMSIIKEEVLAYVV
QLPLYGVIDTPCWKLHTSPLCTTNTKEGSNICLTRTDRGWYCDNAGSVSFFPQAETCKV
QSNRVFCDTMNSLTLPSEVNLCNIDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP
LVFPSDEFDASISQVNEKINQSLAFIRKSDELLHNVNVGKSTTNIMITTIIIVIIVILLLLIAV
GLFLYCKARSTPVTLSKDQLSGINNIAFSN

Ectodomain, RSV CL57-v224

(SEQ ID NO: 70)

MELPILKTNAITTILAAVTLCFASSQNITEEFYQSTCSAVSKGYLSALRTGWYTSVITIELS
NIKENKCNGTDAKVKLIKQELDKYKNAVTELQLLMQSTPAANNRARRELPRFMNYTLN
NTKNNNVTLSKKRKRRFLGFLLGVGSAIASGIAVSKVLHLEGEVNKIKSALLSTNKAVV
SLSNGVSVLTSKVLDLKNYIDKQLLPIVNKQSCSISNIETVIEFQQKNNRLLEITREFSVNA
GVTTPVSTYMLTNSELLSLINDMPITNDQKKLMSNNVQIVRQQSYSIMSIIKEEVLAYVV
QLPLYGVIDTPCWKLHTSPLCTTNTKEGSNICLTRTDRGWYCDNAGSVSFFPQAETCKV
QSNRVFCDTMNSLTLPSEVNLCNIDIFNPKYDCKIMTSKTDVSSSVITSLGAIVSCYGKTK

| Sequences |
|---|
| CTASNKNRGIIKTFSNGCDYVSNKGVDTVSVGNTLYYVNKQEGKSLYVKGEPIINFYDP<br>LVFPSDEFDASISQVNEKINQSLAFIRKSDELL |

PreF, RSV A2, fibritin (SEQ ID NO: 71)

MELLILKANAITTILTAVTFCFASGQNITEEFYQSTCSAVSKGYLSALRTGWYTSVITIELS
NIKKNKCNGTDAKIKLIKQELDKYKNAVTELQLLMQSTPATNNRARRELPRFMNYTLN
NAKKTNVTLSKKRKRRFLGFLLGVGSAIASGVAVSKVLHLEGEVNKIKSALLSTNKAVV
SLSNGVSVLTSKVLDLKNYIDKQLLPIVNKQSCSISNIETVIEFQQKNNRLLEITREFSVNA
GVTTPVSTYMLTNSELLSLINDMPITNDQKKLMSNNVQIVRQQSYSIMSIIKEEVLAYVV
QLPLYGVIDTPCWKLHTSPLCTTNTKEGSNICLTRTDRGWYCDNAGSVSFFPQAETCKV
QSNRVFCDTMNSLTLPSEVNLCNVDIFNPKYDCKIMTSKTDVSSSVITSLGAIVSCYGKT
KCTASNKNRGIIKTFSNGCDYVSNKGVDTVSVGNTLYYVNKQEGKSLYVKGEPIINFYD
PLVFPSDEFDASISQVNEKINQSLAFIRKSDELLSAIGGYIPEAPRDGQAYVRKDGEWVLL
STFL

PreF N67I S215P, RSV A2, fibritin (SEQ ID NO: 72)

MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNRARRELPRFMNYTLN
AKKINVTLSKKRKRRFLGFLLGVGSAIASGVAVSKVLHLEGEVNKIKSALLSTNKAVVS
LSNGVSVLTSKVLDLKNYIDKQLLPIVNKQSCSIPNIETVIEFQQKNNRLLEITREFSVNAG
VTTPVSTYMLTNSELLSLINDMPITNDQKKLMSNNVQIVRQQSYSIMSIIKEEVLAYVVQ
LPLYGVIDTPCWKLHTSPLCTTNTKEGSNICLTRTDRGWYCDNAGSVSFFPQAETCKVQ
SNRVFCDTMNSLTLPSEVNLCNVDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP
LVFPSDEFDASISQVNEKINQSLAFIRKSDELLSAIGGYIPEAPRDGQAYVRKDGEWVLLS
TFL

PreF N67I S215P, RSV B1, fibritin (SEQ ID NO: 73)

MELLIHRLSAIFLTLAINALYLTSSQNITEEFYQSTCSAVSRGYFSALRTGWYTSVITIELS
NIKEIKCNGTDTKVKLIKQELDKYKNAVTELQLLMQNTPAANNRARREAPQYMNYTIN
TTKNLNVSISKKRKRRFLGFLLGVGSAIASGIAVSKVLHLEGEVNKIKNALLSTNKAVVS
LSNGVSVLTSKVLDLKNYINNQLLPIVNQQSCRIPNIETVIEFQQKNSRLLEINREFSVNAG
VTTPLSTYMLINSELLSLINDMPITNDQKKLMSSNVQIVRQQSYSIMSIIKEEVLAYVVQL
PIYGVIDTPCWKLHTSPLCTTNIKEGSNICLTRTDRGWYCDNAGSVSFFPQADTCKVQSN
RVFCDTMNSLTLPSEVSLCNTDIFNSKYDCKIMTSKTDISSSVITSLGAIVSCYGKTKCTA
SNKNRGIIKTFSNGCDYVSNKGVDTVSVGNTLYYVNKLEGKNLYVKGEPIINYYDPLVF
PSDEFDASISQVNEKINQSLAFIRRSDELLSAIGGYIPEAPRDGQAYVRKDGEWVLLSTFL

RSV N67I S215P, RSV CL57-v224, fibritin (SEQ ID NO: 74)

MELPILKTNAITTILAAVTLCFASSQNITEEFYQSTCSAVSKGYLSALRTGWYTSVITIELS
NIKEIKCNGTDAKVKLIKQELDKYKNAVTELQLLMQSTPAANNRARRELPRFMNYTLN
NTKNNNVTLSKKRKRRFLGFLLGVGSAIASGIAVSKVLHLEGEVNKIKSALLSTNKAVV
SLSNGVSVLTSKVLDLKNYIDKQLLPIVNKQSCSIPNIETVIEFQQKNNRLLEITREFSVNA
GVTTPVSTYMLTNSELLSLINDMPITNDQKKLMSNNVQIVRQQSYSIMSIIKEEVLAYVV
QLPLYGVIDTPCWKLHTSPLCTTNTKEGSNICLTRTDRGWYCDNAGSVSFFPQAETCKV
QSNRVFCDTMNSLTLPSEVNLCNIDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP
LVFPSDEFDASISQVNEKINQSLAFIRKSDELLSAIGGYIPEAPRDGQAYVRKDGEWVLLS
TFL

PreFL N67I S215P, RSV B1, fibritin, Loop (SEQ ID NO: 22)

MELLIHRLSAIFLTLAINALYLTSSQNITEEFYQSTCSAVSRGYFSALRTGWYTSVITIELS
NIKEIKCNGTDTKVKLIKQELDKYKNAVTELQLLMQNTPAANNQARGSGSGRSLGFLLG
VGSAIASGIAVSKVLHLEGEVNKIKNALLSTNKAVVSLSNGVSVLTSKVLDLKNYINNQL
LPIVNQQSCRIPNIETVIEFQQKNSRLLEINREFSVNAGVTTPLSTYMLTNSELLSLINDMPI
TNDQKKLMSSNVQIVRQQSYSIMSIIKEEVLAYVVQLPIYGVIDTPCWKLHTSPLCTTNIK
EGSNICLTRTDRGWYCDNAGSVSFFPQADTCKVQSNRVFCDTMNSLTLPSEVSLCNTDI
FNSKYDCKIMTSKTDISSSVITSLGAIVSCYGKTKCTASNKNRGIIKTFSNGCDYVSNKGV
DTVSVGNTLYYVNKLEGKNLYVKGEPIINYYDPLVFPSDEFDASISQVNEKINQSLAFIRR
SDELLSAIGGYIPEAPRDGQAYVRKDGEWVLLSTFL

PreFL N67I S215P, RSV CL57-v224, fibritin, Loop (SEQ ID NO: 75)

MELPILKTNAITTILAAVTLCFASSQNITEEFYQSTCSAVSKGYLSALRTGWYTSVITIELS
NIKEIKCNGTDAKVKLIKQELDKYKNAVTELQLLMQSTPAANNQARGSGSGRSLGFLLG
VGSAIASGIAVSKVLHLEGEVNKIKSALLSTNKAVVSLSNGVSVLTSKVLDLKNYIDKQL
LPIVNKQSCSIPNIETVIEFQQKNNRLLEITREFSVNAGVTTPVSTYMLTNSELLSLINDMPI
TNDQKKLMSNNVQIVRQQSYSIMSIIKEEVLAYVVQLPLYGVIDTPCWKLHTSPLCTTNT
KEGSNICLTRTDRGWYCDNAGSVSFFPQAETCKVQSNRVFCDTMNSLTLPSEVNLCNIDI
FNPKYDCKIMTSKTDVSSSVITSLGAIVSCYGKTKCTASNKNRGIIKTFSNGCDYVSNKG
VDTVSVGNTLYYVNKQEGKSLYVKGEPIINFYDPLVFPSDEFDASISQVNEKINQSLAFIR
KSDELLSAIGGYIPEAPRDGQAYVRKDGEWVLLSTFL

| Sequences |
| --- |

PreF N67I S215P E487Q, RSV A2, fibritin
(SEQ ID NO: 76)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNRARRELPRFMNYTLNN
AKKTNVTLSKKRKRRFLGFLLGVGSAIASGVAVSKVLHLEGEVNKIKSALLSTNKAVVS
LSNGVSVLTSKVLDLKNYIDKQLLPIVNKQSCSIPNIETVIEFQQKNNRLLEITREFSVNAG
VTTPVSTYMLTNSELLSLINDMPITNDQKKLMSNNVQIVRQQSYSIMSIIKEEVLAYVVQ
LPLYGVIDTPCWKLHTSPLCTTNTKEGSNICLTRTDRGWYCDNAGSVSFFPQAETCKVQ
SNRVFCDTMNSLTLPSEVNLCNVDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP
LVFPSDQFDASISQVNEKINQSLAFIRKSDELLSAIGGYIPEAPRDGQAYVRKDGEWVLLS
TFL PreF N67I S215P K201N, RSV A2, fibritin
(SEQ ID NO: 77)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNRARRELPRFMNYTLNN
AKKTNVTLSKKRKRRFLGFLLGVGSAIASGVAVSKVLHLEGEVNKIKSALLSTNKAVVS
LSNGVSVLTSKVLDLKNYIDNQLLPIVNKQSCSIPNIETVIEFQQKNNRLLEITREFSVNAG
VTTPVSTYMLTNSELLSLINDMPITNDQKKLMSNNVQIVRQQSYSIMSIIKEEVLAYVVQ
LPLYGVIDTPCWKLHTSPLCTTNTKEGSNICLTRTDRGWYCDNAGSVSFFPQAETCKVQ
SNRVFCDTMNSLTLPSEVNLCNVDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP
LVFPSDEFDASISQVNEKINQSLAFIRKSDELLSAIGGYIPEAPRDGQAYVRKDGEWVLLS
TFL PreF N67I S215P E92D, RSV A2, fibritin
(SEQ ID NO: 78)
MELLILKANAITTILTAVTFCFASGQNITEEFYQSTCSAVSKGYLSALRTGWYTSVITIELS
NIKKIKCNGTDAKIKLIKQELDKYKNAVTDLQLLMQSTPATNNRARRELPRFMNYTLNN
AKKTNVTLSKKRKRRFLGFLLGVGSAIASGVAVSKVLHLEGEVNKIKSALLSTNKAVVS
LSNGVSVLTSKVLDLKNYIDKQLLPIVNKQSCSIPNIETVIEFQQKNNRLLEITREFSVNAG
VTTPVSTYMLTNSELLSLINDMPITNDQKKLMSNNVQIVRQQSYSIMSIIKEEVLAYVVQ
LPLYGVIDTPCWKLHTSPLCTTNTKEGSNICLTRTDRGWYCDNAGSVSFFPQAETCKVQ
SNRVFCDTMNSLTLPSEVNLCNVDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP
LVFPSDEFDASISQVNEKINQSLAFIRKSDELLSAIGGYIPEAPRDGQAYVRKDGEWVLLS
TFL PreF N67I S215P D486N, RSV A2, fibritin
(SEQ ID NO: 79)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPAINNRARRELPRFMNYTLNN
AKKTNVTLSKKRKRRFLGFLLGVGSAIASGVAVSKVLHLEGEVNKIKSALLSTNKAVVS
LSNGVSVLTSKVLDLKNYIDKQLLPIVNKQSCSIPNIETVIEFQQKNNRLLEITREFSVNAG
VTTPVSTYMLTNSELLSLINDMPITNDQKKLMSNNVQIVRQQSYSIMSIIKEEVLAYVVQ
LPLYGVIDTPCWKLHTSPLCTTNTKEGSNICLTRTDRGWYCDNAGSVSFFPQAETCKVQ
SNRVFCDTMNSLTLPSEVNLCNVDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP
LVFPSNEFDASISQVNEKINQSLAFIRKSDELLSAIGGYIPEAPRDGQAYVRKDGEWVLLS
TFL Fwt N67I S215P, membrane-bound RSV F, A2,
(SEQ ID NO: 80)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNRARRELPRFMNYTLNN
AKKTNVTLSKKRKRRFLGFLLGVGSAIASGVAVSKVLHLEGEVNKIKSALLSTNKAVVS
LSNGVSVLTSKVLDLKNYIDKQLLPIVNKQSCSIPNIETVIEFQQKNNRLLEITREFSVNAG
VTTPVSTYMLTNSELLSLINDMPITNDQKKLMSNNVQIVRQQSYSIMSIIKEEVLAYVVQ
LPLYGVIDTPCWKLHTSPLCTTNTKEGSNICLTRTDRGWYCDNAGSVSFFPQAETCKVQ
SNRVFCDTMNSLTLPSEVNLCNVDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP
LVFPSDEFDASISQVNEKINQSLAFIRKSDELLHNVAVKSTTNIMITTIIIVIIVILLSLIAVG
LLLYCKARSTPVTLSKDQLSGINNIAFSN Fsl N67I S215P, membrane-bound RSV F, A2,
(SEQ ID NO: 81)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLHNVAVKSTTNIMITTIIIVIIVILLSLIAVGLLLYCKARSTPVTLSKDQLSGIN
NIAFSN -continued

| Sequences |
|---|

Fwt N67I S215P E92D, membrane-bound RSV F, A2,
(SEQ ID NO: 82)
MELLILKANAITTILTAVTFCFASGQNITEEFYQSTCSAVSKGYLSALRTGWYTSVITIELS
NIKKIKCNGTDAKIKLIKQELDKYKNAVTDLQLLMQSTPATNNRARRELPRFMNYTLNN
AKKTNVTLSKKRKRRFLGFLLGVGSAIASGVAVSKVLHLEGEVNKIKSALLSTNKAVVS
LSNGVSVLTSKVLDLKNYIDKQLLPIVNKQSCSIPNIETVIEFQQKNNRLLEITREFSVNAG
VTTPVSTYMLTNSELLSLINDMPITNDQKKLMSNNVQIVRQQSYSIMSIIKEEVLAYVVQ
LPLYGVIDTPCWKLHTSPLCTTNTKEGSNICLTRTDRGWYCDNAGSVSFFPQAETCKVQ
SNRVFCDTMNSLTLPSEVNLCNVDIFNPKYDCKIMTSKTDVSSSVITSLGAIVSCYGKIK
CTASNKNRGIIKTFSNGCDYVSNKGVDTVSVGNTLYYVNKQEGKSLYVKGEPIINFYDP
LVFPSDEFDASISQVNEKINQSLAFIRKSDELLHNVNAVKSTTNIMITTIIIVIIVILLSLIAVG
LLLYCKARSTPVTLSKDQLSGINNIAFSN Fsl N67I S215P E92D, membrane-bound RSV F, A2,
(SEQ ID NO: 83)
MELLILKANAITTILTAVTFCFASGQNITEEFYQSTCSAVSKGYLSALRTGWYTSVITIELS
NIKKIKCNGTDAKIKLIKQELDKYKNAVTDLQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLHNVNAVKSTTNIMITTIIIVIIVILLSLIAVGLLLYCKARSTPVTLSKDQLSGIN
NIAFSN Fwt N67I S215P E487Q, membrane-bound RSV F, A2,
(SEQ ID NO: 84)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNRARRELPRFMNYTLNN
AKKTNVTLSKKRKRRFLGFLLGVGSAIASGVAVSKVLHLEGEVNKIKSALLSTNKAVVS
LSNGVSVLTSKVLDLKNYIDKQLLPIVNKQSCSIPNIETVIEFQQKNNRLLEITREFSVNAG
VTTPVSTYMLTNSELLSLINDMPITNDQKKLMSNNVQIVRQQSYSIMSIIKEEVLAYVVQ
LPLYGVIDTPCWKLHTSPLCTTNTKEGSNICLTRTDRGWYCDNAGSVSFFPQAETCKVQ
SNRVFCDTMNSLTLPSEVNLCNVDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP
LVFPSDQFDASISQVNEKINQSLAFIRKSDELLHNVNAVKSTTNIMITTIIIVIIVILLSLIAV
GLLLYCKARSTPVTLSKDQLSGINNIAFSN Fsl N67I S215P E487Q, membrane-bound RSV F, A2,
(SEQ ID NO: 85)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDQFDASISQVNEKINQSLA
FIRKSDELLHNVNAVKSTTNIMITTIIIVIIVILLSLIAVGLLLYCKARSTPVTLSKDQLSGIN
NIAFSN Fwt N67I S215P D486N, membrane-bound RSV F, A2,
(SEQ ID NO: 86)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNRARRELPRFMNYTLNN
AKKTNVTLSKKRKRRFLGFLLGVGSAIASGVAVSKVLHLEGEVNKIKSALLSTNKAVVS
LSNGVSVLTSKVLDLKNYIDKQLLPIVNKQSCSIPNIETVIEFQQKNNRLLEITREFSVNAG
VTTPVSTYMLTNSELLSLINDMPITNDQKKLMSNNVQIVRQQSYSIMSIIKEEVLAYVVQ
LPLYGVIDTPCWKLHTSPLCTTNTKEGSNICLTRTDRGWYCDNAGSVSFFPQAETCKVQ
SNRVFCDTMNSLTLPSEVNLCNVDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP
LVFPSNEFDASISQVNEKINQSLAFIRKSDELLHNVNAVKSTTNIMITTIIIVIIVILLSLIAVG
LLLYCKARSTPVTLSKDQLSGINNIAFSN Fsl N67I S215P D486N, membrane-bound RSV F, A2,
(SEQ ID NO: 87)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSNEFDASISQVNEKINQSLA
FIRKSDELLHNVNAVKSTTNIMITTIIIVIIVILLSLIAVGLLLYCKARSTPVTLSKDQLSGIN
NIAFSN

Sequences

Fwt N67I S215P S46G, membrane-bound RSV F, A2,
(SEQ ID NO: 88)
MELLILKANAITTILTAVTFCFASGQNITEEFYQSTCSAVSKGYLGALRTGWYTSVITIELS
NIKKIKCNGTDAKIKLIKQELDKYKNAVTELQLLMQSTPATNNRARRELPRFMNYTLNN
AKKTNVTLSKKRKRRFLGFLLGVGSAIASGVAVSKVLHLEGEVNKIKSALLSTNKAVVS
LSNGVSVLTSKVLDLKNYIDKQLLPIVNKQSCSIPNIETVIEFQQKNNRLLEITREFSVNAG
VTTPVSTYMLTNSELLSLINDMPITNDQKKLMSNNVQIVRQQSYSIMSIIKEEVLAYVVQ
LPLYGVIDTPCWKLHTSPLCTTNTKEGSNICLTRTDRGWYCDNAGSVSFFPQAETCKVQ
SNRVFCDTMNSLTLPSEVNLCNVDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP
LVFPSDEFDASISQVNEKINQSLAFIRKSDELLHNVNAVKSTTNIMITTIIIVIIVILLSLIAVG
LLLYCKARSTPVTLSKDQLSGINNIAFSN Fsl N67I S215P S46G, membrane-bound RSV F, A2,
(SEQ ID NO: 89)
MELLILKANAITTILTAVTFCFASGQNITEEFYQSTCSAVSKGYLGALRTGWYTSVITIELS
NIKKIKCNGTDAKIKLIKQELDKYKNAVTELQLLMQSTPATNNQARGSGSGRSLGFLLG
VGSAIASGVAVSKVLHLEGEVNKIKSALLSTNKAVVSLSNGVSVLTSKVLDLKNYIDKQ
LLPIVNKQSCSIPNIETVIEFQQKNNRLLEITREFSVNAGVTTPVSTYMLTNSELLSLINDM
PITNDQKKLMSNNVQIVRQQSYSIMSIIKEEVLAYVVQLPLYGVIDTPCWKLHTSPLCTT
NTKEGSNICLTRTDRGWYCDNAGSVSFFPQAETCKVQSNRVFCDTMNSLTLPSEVNLCN
VDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLA
FIRKSDELLHNVNAVKSTTNIMITTIIIVIIVILLSLIAVGLLLYCKARSTPVTLSKDQLSGIN
NIAFSN CR9501 heavy chain
(SEQ ID NO: 53)
QVQLVQSGPGLVKPSQTLALTCNVSGASINSDNYYWTWIRQRPGGGLEWIGHISYTGNT
YYTPSLKSRLSMSLETSQSQFSLRLTSVTAADSAVYFCAACGAYVLISNCGWFDSWGQG
TQVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSC CR9501 light chain
(SEQ ID NO: 61)
EIVMTQSPSSLSASIGDRVTITCQASQDISTYLNWYQQKPGQAPRLLIYGASNLETGVPSR
FTGSGYGTDFSVTISSLQPEDIATYYCQQYQYLPYTFAPGTKVEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC CR9502 heavy chain
(SEQ ID NO: 57)
EVQLLQSGAELKKPGASVKISCKTSGFTFSGHTIAWVRQAPGQGLEWMGWVSTNNGNT
EYAQKIQGRVTMTMDTSTSTVYMELRSLTSDDTAVYFCAREWLVMGGFAFDHWGQGT
LLTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSC CR9502 light chain
(SEQ ID NO: 65)
QSVLTQASSVSVAPGQTARITCGANNIGSQNVHWYQQKPGQAPVLVVYDDRDRPSGIP
DRFSGSNSGNTATLTISRVEAGDEADYYCQVWDSSRDQAVIFGGGTKLTVLGQPKAAPS
VTLFPPSSEELQANKATLVCLISDFYPGAVTVAWKADSSPVKAGVETTTPSKQSNNKYA
ASSYLSLTPEQWKSHRSYSCQVTHEGSTVEKTIAPTECS PreF N67I E161P S215P E487Q, RSV A2, fibritin
(SEQ ID NO: 90)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNRARRELPRFMNYTLNN
AKKTNVTLSKKRKRRFLGFLLGVGSAIASGVAVSKVLHLPGEVNKIKSALLSTNKAVVS
LSNGVSVLTSKVLDLKNYIDKQLLPIVNKQSCSIPNIETVIEFQQKNNRLLEITREFSVNAG
VTTPVSTYMLTNSELLSLINDMPITNDQKKLMSNNVQIVRQQSYSIMSIIKEEVLAYVVQ
LPLYGVIDTPCWKLHTSPLCTTNTKEGSNICLTRTDRGWYCDNAGSVSFFPQAETCKVQ
SNRVFCDTMNSLTLPSEVNLCNVDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP
LVFPSDQFDASISQVNEKINQSLAFIRKSDELLSAIGGYIPEAPRDGQAYVRKDGEWVLLS
TFL PreF N67I E161P S215P, RSV A2, fibritin
(SEQ ID NO: 91)
MELLILKANAITTILTAVTFCFASGQNITEEFYQSTCSAVSKGYLSALRTGWYTSVITIELS
NIKKIKCNGTDAKIKLIKQELDKYKNAVTELQLLMQSTPATNNRARRELPRFMNYTLNN
AKKTNVTLSKKRKRRFLGFLLGVGSAIASGVAVSKVLHLPGEVNKIKSALLSTNKAVVS
LSNGVSVLTSKVLDLKNYIDKQLLPIVNKQSCSIPNIETVIEFQQKNNRLLEITREFSVNAG
VTTPVSTYMLTNSELLSLINDMPITNDQKKLMSNNVQIVRQQSYSIMSIIKEEVLAYVVQ
LPLYGVIDTPCWKLHTSPLCTTNTKEGSNICLTRTDRGWYCDNAGSVSFFPQAETCKVQ
SNRVFCDTMNSLTLPSEVNLCNVDIFNPKYDCKIMTSKTDVSSSVITSLGAIVSCYGKTK
CTASNKNRGIIKTFSNGCDYVSNKGVDTVSVGNTLYYVNKQEGKSLYVKGEPIINFYDP

| Sequences |
| --- |
| LVFPSDEFDASISQVNEKINQSLAFIRKSDELLSAIGGYIPEAPRDGQAYVRKDGEWVLLS<br>TFL<br><br>PreF N67I S173P S215P, RSV A2, fibritin<br>(SEQ ID NO: 92)<br>MELLILKANAITTILTAVTFCFASGQNITEEFYQSTCSAVSKGYLSALRTGWYTSVITIELS<br>NIKKIKCNGTDAKIKLIKQELDKYKNAVTELQLLMQSTPATNNRARRELPRFMNYTLNN<br>AKKTNVTLSKKRKRRFLGFLLGVGSAIASGVAVSKVLHLEGEVNKIKSALLPTNKAVVS<br>LSNGVSVLTSKVLDLKNYIDKQLLPIVNKQSCSIPNIETVIEFQQKNNRLLEITREFSVNAG<br>VTTPVSTYMLINSELLSLINDMPITNDQKKLMSNNVQIVRQQSYSIMSIIKEEVLAYVVQ<br>LPLYGVIDTPCWKLHTSPLCTTNTKEGSNICLTRTDRGWYCDNAGSVSFFPQAETCKVQ<br>SNRVFCDTMNSLTLPSEVNLCNVDIFNPKYDCKIMTSKTDVSSSVITSLGAIVSCYGKTK<br>CTASNKNRGIIKTFSNGCDYVSNKGVDTVSVGNTLYYVNKQEGKSLYVKGEPIINFYDP<br>LVFPSDEFDASISQVNEKINQSLAFIRKSDELLSAIGGYIPEAPRDGQAYVRKDGEWVLLS<br>TFL<br><br>PreF N67I S182P S215P, RSV A2, fibritin<br>(SEQ ID NO: 93)<br>MELLILKANAITTILTAVTFCFASGQNITEEFYQSTCSAVSKGYLSALRTGWYTSVITIELS<br>NIKKIKCNGTDAKIKLIKQELDKYKNAVTELQLLMQSTPATNNRARRELPRFMNYTLNN<br>AKKTNVTLSKKRKRRFLGFLLGVGSAIASGVAVSKVLHLEGEVNKIKSALLSTNKAVVS<br>LPNGVSVLTSKVLDLKNYIDKQLLPIVNKQSCSIPNIETVIEFQQKNNRLLEITREFSVNAG<br>VTTPVSTYMLTNSELLSLINDMPITNDQKKLMSNNVQIVRQQSYSIMSIIKEEVLAYVVQ<br>LPLYGVIDTPCWKLHTSPLCTTNTKEGSNICLTRTDRGWYCDNAGSVSFFPQAETCKVQ<br>SNRVFCDTMNSLTLPSEVNLCNVDIFNPKYDCKIMTSKTDVSSSVITSLGAIVSCYGKTK<br>CTASNKNRGIIKTFSNGCDYVSNKGVDTVSVGNTLYYVNKQEGKSLYVKGEPIINFYDP<br>LVFPSDEFDASISQVNEKINQSLAFIRKSDELLSAIGGYIPEAPRDGQAYVRKDGEWVLLS<br>TFL<br><br>PreF N67I S215P D486C E487C, RSV A2, fibritin<br>(SEQ ID NO: 94)<br>MELLILKANAITTILTAVTFCFASGQNITEEFYQSTCSAVSKGYLSALRTGWYTSVITIELS<br>NIKKIKCNGTDAKIKLIKQELDKYKNAVTELQLLMQSTPATNNRARRELPRFMNYTLNN<br>AKKTNVILSKKRKRRFLGFLLGVGSAIASGVAVSKVLHLEGEVNKIKSALLSTNKAVVS<br>LSNGVSVLTSKVLDLKNYIDKQLLPIVNKQSCSIPNIETVIEFQQKNNRLLEITREFSVNAG<br>VTTPVSTYMLTNSELLSLINDMPITNDQKKLMSNNVQIVRQQSYSIMSIIKEEVLAYVVQ<br>LPLYGVIDTPCWKLHTSPLCTTNTKEGSNICLTRTDRGWYCDNAGSVSFFPQAETCKVQ<br>SNRVFCDTMNSLTLPSEVNLCNVDIFNPKYDCKIMTSKTDVSSSVITSLGAIVSCYGKTK<br>CTASNKNRGIIKTFSNGCDYVSNKGVDTVSVGNTLYYVNKQEGKSLYVKGEPIINFYDP<br>LVFPSCCFDASISQVNEKINQSLAFIRKSDELLSAIGGYIPEAPRDGQAYVRKDGEWVLLS<br>TFL |

The invention claimed is:

1. A recombinant respiratory syncytial virus (RSV) Fusion (F) polypeptide comprising, from amino-terminus to carboxyl-terminus, an F2 domain, a linking sequence consisting of SEQ ID NO:5, a truncated F1 domain, and a trimerization domain having the amino acid sequence of SEQ ID NO:4 linked to the truncated F1 domain at position 513 of the F polypeptide, wherein the truncated F1 domain comprises at least one mutation, as compared to wild-type F1 domain, selected from the group consisting of:
   (a) a mutation of the amino acid residue E at position 161 to P, Q or G;
   (b) a mutation of the amino acid residue S at position 173 to P; and
   (c) a mutation of the amino acid residue I at position 214 to P,
wherein the numbering of amino acid residues is in accordance with that of SEQ ID NO: 1.

2. The recombinant RSV F polypeptide of claim 1, wherein the F2 domain comprises a mutation of the amino acid residue at position 67 to I, and the truncated F1 domain further comprises a mutation of the amino acid residue at position 215 to P.

3. The recombinant RSV F polypeptide of claim 2, comprising the amino acid sequence of SEQ ID NO: 19, except the mutation of the amino acid residue at position 67 to I, the mutation of the amino acid residue at position 215 to P, and the at least one mutation selected from the group consisting of:
   (a) a mutation of the amino acid residue E at position 161 to P, Q or G;
   (b) a mutation of the amino acid residue S at position 173 to P; and
   (c) a mutation of the amino acid residue I at position 214 to P.

4. A composition comprising the recombinant RSV F polypeptide of claim 1.

5. A method of inducing an immune response against RSV F protein in a subject, the method comprising: administering to the subject an amount of the recombinant RSV F polypeptide of claim 1 to induce the immune response against RSV F protein in the subject.

6. A recombinant respiratory syncytial virus (RSV) Fusion (F) polypeptide comprising, from amino-terminus to carboxyl-terminus, an F2 domain, a linking sequence consisting of SEQ ID NO:5, a truncated F1 domain, and a trimerization domain having the amino acid sequence of SEQ ID NO:4 linked to the truncated F1 domain at position 513 of the F polypeptide, wherein, as compared to wild-type F1 domain, the truncated F1 domain comprises a mutation of the amino acid residue D at position 486 to C and a mutation of the amino acid residue E at position 487 to C, wherein the numbering of amino acid residues is in accordance with that of SEQ ID NO: 1.

7. The recombinant RSV F polypeptide of claim 6, wherein the F2 domain comprises a mutation of the amino acid residue at position 67 to I, and the truncated F1 domain further comprises a mutation of the amino acid residue at position 215 to P.

8. The recombinant RSV F polypeptide of claim 7, comprising the amino acid sequence of SEQ ID NO: 19, except the mutation of the amino acid residue at position 67 to I, the mutation of the amino acid residue at position 215 to P, the mutation of the amino acid residue D at position 486 to C and the mutation of the amino acid residue E at position 487 to C.

9. A composition comprising the recombinant RSV F polypeptide of claim 6.

10. A method of inducing an immune response against RSV F protein in a subject, the method comprising: administering to the subject an amount of the recombinant RSV F polypeptide of claim 6 to induce the immune response against RSV F protein in the subject.

11. The RSV F polypeptide according to claim 1, wherein the RSV F polypeptide is trimeric.

12. The RSV F polypeptide of claim 1, further comprising at least one of a mutation of the amino acid residue at position 67 and a mutation of the amino acid residue at position 215.

13. The RSV F polypeptide according to claim 1, wherein the RSV F polypeptide comprises at least one of a mutation of the amino acid residue N or T at position 67 and a mutation of amino acid residue S at position 215.

14. The RSV F polypeptide of claim 1, wherein at least one of the truncated F1 domain and the F2 domain is from an RSV A strain.

15. The RSV F polypeptide of claim 1, wherein at least one of the truncated F1 domain and the F2 domain is from an RSV B strain.

16. A recombinant respiratory syncytial virus (RSV) F polypeptide comprising an amino acid sequence selected from the group consisting of SEQ ID NO: 90-SEQ ID NO: 94.

17. A composition comprising: the RSV F polypeptide of claim 16.

18. A method of inducing an immune response against RSV F protein in a subject, the method comprising: administering to the subject an amount of the RSV F polypeptide of claim 16 to induce an immune response against RSV F protein in the subject.

19. A vaccine comprising: the RSV F polypeptide of claim 16.

20. A method of prophylaxing and/or treating an RSV F infection in a subject, the method comprising:
   administering to the subject an amount of the RSV F polypeptide of claim 16 to prophylax and/or treat the subject for an RSV infection.

21. A method of producing the RSV F polypeptide of claim 1, the method comprising:
   expressing in a host cell a nucleic acid molecule encoding the RSV F polypeptide.

22. The method according to claim 21, wherein the host cell is a mammalian cell, and the nucleic acid molecule has been codon-optimized for expression in mammalian cells.

\* \* \* \* \*

SEQUENCE LISTING

<160> NUMBER OF SEQ ID NOS: 100

<210> SEQ ID NO 1
<211> LENGTH: 574
<212> TYPE: PRT
<213> ORGANISM: Artificial Sequence
<220> FEATURE:
<223> OTHER INFORMATION: RSV F protein A2 full length sequence

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

-continued

```
Met Gln Ser Thr Pro Ala Thr Asn Arg Ala Arg Glu Leu Pro
             100                 105                 110
Arg Phe Met Asn Tyr Thr Leu Asn Asn Ala Lys Lys Thr Asn Val Thr
        115                 120                 125
Leu Ser Lys Lys Arg Lys Arg Arg Phe Leu Gly Phe Leu Leu Gly Val
    130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asp Lys Gln Leu Leu Pro Ile Val Asn
        195                 200                 205
Lys Gln Ser Cys Ser Ile Ser Asn Ile Glu Thr Val Ile Glu Phe Gln
    210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
    370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
    450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu His Asn Val Asn Ala Val Lys Ser Thr Thr Asn Ile Met Ile Thr
```

```
            515                 520                 525
Thr Ile Ile Ile Val Ile Ile Val Ile Leu Leu Ser Leu Ile Ala Val
            530                 535                 540
Gly Leu Leu Leu Tyr Cys Lys Ala Arg Ser Thr Pro Val Thr Leu Ser
545                 550                 555                 560
Lys Asp Gln Leu Ser Gly Ile Asn Asn Ile Ala Phe Ser Asn
                565                 570
```

<210> SEQ ID NO 2
<211> LENGTH: 574
<212> TYPE: PRT
<213> ORGANISM: Artificial Sequence
<220> FEATURE:
<223> OTHER INFORMATION: RSV F protein B1 full length sequence

<400> SEQUENCE: 2

```
Met Glu Leu Leu Ile His Arg Leu Ser Ala Ile Phe Leu Thr Leu Ala
1               5                   10                  15
Ile Asn Ala Leu Tyr Leu Thr Ser Ser Gln Asn Ile Thr Glu Glu Phe
            20                  25                  30
Tyr Gln Ser Thr Cys Ser Ala Val Ser Arg Gly Tyr Phe Ser Ala Leu
        35                  40                  45
Arg Thr Gly Trp Tyr Thr Ser Val Ile Thr Ile Glu Leu Ser Asn Ile
    50                  55                  60
Lys Glu Thr Lys Cys Asn Gly Thr Asp Thr Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Asn Thr Pro Ala Ala Asn Asn Arg Ala Arg Arg Glu Ala Pro
            100                 105                 110
Gln Tyr Met Asn Tyr Thr Ile Asn Thr Thr Lys Asn Leu Asn Val Ser
        115                 120                 125
Ile Ser Lys Lys Arg Lys Arg Arg Phe Leu Gly Phe Leu Leu Gly Val
    130                 135                 140
Gly Ser Ala Ile Ala Ser Gly Ile Ala Val Ser Lys Val Leu His Leu
145                 150                 155                 160
Glu Gly Glu Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asn Asn Gln Leu Leu Pro Ile Val Asn
        195                 200                 205
Gln Gln Ser Cys Arg Ile Ser Asn Ile Glu Thr Val Ile Glu Phe Gln
    210                 215                 220
Gln Lys Asn Ser Arg Leu Leu Glu Ile Asn Arg Glu Phe Ser Val Asn
225                 230                 235                 240
Ala Gly Val Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Ser Tyr Ser Ile
        275                 280                 285
Met Ser Ile Ile Lys Glu Glu Val Leu Ala Tyr Val Val Gln Leu Pro
    290                 295                 300
Ile Tyr Gly Val Ile Asp Thr Pro Cys Trp Lys Leu His Thr Ser Pro
```

```
                     305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn Ile Met Ile Thr
            515                 520                 525

Thr Ile Ile Ile Val Ile Ile Val Val Leu Leu Ser Leu Ile Ala Ile
        530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570

<210> SEQ ID NO 3
<211> LENGTH: 20
<212> TYPE: PRT
<213> ORGANISM: Artificial Sequence
<220> FEATURE:
<223> OTHER INFORMATION: Trimerization domain

<400> SEQUENCE: 3

Glu Lys Lys Ile Glu Ala Ile Glu Lys Lys Ile Glu Ala Ile Glu Lys
1               5                   10                  15

Lys Ile Glu Ala
            20

<210> SEQ ID NO 4
<211> LENGTH: 27
<212> TYPE: PRT
<213> ORGANISM: Artificial Sequence
<220> FEATURE:
<223> OTHER INFORMATION: Trimerization domain

<400> SEQUENCE: 4

Gly Tyr Ile Pro Glu Ala Pro Arg Asp Gly Gln Ala Tyr Val Arg Lys
1               5                   10                  15
```

```
Asp Gly Glu Trp Val Leu Leu Ser Thr Phe Leu
            20                  25

<210> SEQ ID NO 5
<211> LENGTH: 5
<212> TYPE: PRT
<213> ORGANISM: Artificial Sequence
<220> FEATURE:
<223> OTHER INFORMATION: linker

<400> SEQUENCE: 5

Gly Ser Gly Ser Gly
1               5

<210> SEQ ID NO 6
<211> LENGTH: 40
<212> TYPE: PRT
<213> ORGANISM: Artificial Sequence
<220> FEATURE:
<223> OTHER INFORMATION: Trimerization domain

<400> SEQUENCE: 6

Ser Ser Leu Gln Gly Asp Val Gln Ala Leu Gln Glu Ala Gly Tyr Ile
1               5                   10                  15

Pro Glu Ala Pro Arg Asp Gly Gln Ala Tyr Val Arg Lys Asp Gly Glu
            20                  25                  30

Trp Val Leu Leu Ser Thr Phe Leu
        35                  40

<210> SEQ ID NO 7
<211> LENGTH: 7
<212> TYPE: PRT
<213> ORGANISM: Artificial Sequence
<220> FEATURE:
<223> OTHER INFORMATION: Isoleucine Zipper domain

<400> SEQUENCE: 7

Ile Glu Ala Ile Glu Lys Lys
1               5

<210> SEQ ID NO 8
<211> LENGTH: 31
<212> TYPE: PRT
<213> ORGANISM: Artificial Sequence
<220> FEATURE:
<223> OTHER INFORMATION: Isoleucine Zipper (L)

<400> SEQUENCE: 8

Ile Glu Lys Lys Ile Glu Ala Ile Glu Lys Lys Ile Glu Ala Ile Glu
1               5                   10                  15

Lys Lys Ile Glu Ala Ile Glu Ala Ile Glu Lys Lys Ile Glu Ala
            20                  25                  30

<210> SEQ ID NO 9
<211> LENGTH: 28
<212> TYPE: PRT
<213> ORGANISM: Artificial Sequence
<220> FEATURE:
<223> OTHER INFORMATION: GCN4II

<400> SEQUENCE: 9

Glu Asp Lys Ile Glu Glu Ile Leu Ser Lys Ile Tyr His Ile Glu Asn
1               5                   10                  15

Glu Ile Ala Arg Ile Lys Lys Leu Ile Gly Glu Ala
            20                  25
```

<210> SEQ ID NO 10
<211> LENGTH: 28
<212> TYPE: PRT
<213> ORGANISM: Artificial Sequence
<220> FEATURE:
<223> OTHER INFORMATION: Optimized GCN4II

<400> SEQUENCE: 10

Glu Asp Lys Val Glu Glu Leu Leu Ser Lys Ile Tyr His Ile Glu Asn
1               5                   10                  15

Arg Ile Ala Arg Ile Glu Lys Leu Val Gly Glu Ala
            20                  25

<210> SEQ ID NO 11
<211> LENGTH: 43
<212> TYPE: PRT
<213> ORGANISM: Artificial Sequence
<220> FEATURE:
<223> OTHER INFORMATION: Matrilin -1 (long version)

<400> SEQUENCE: 11

Glu Glu Asp Pro Cys Glu Cys Lys Ser Ile Val Lys Phe Gln Thr Lys
1               5                   10                  15

Val Glu Glu Leu Ile Asn Thr Leu Gln Gln Lys Leu Glu Ala Val Ala
            20                  25                  30

Lys Arg Ile Glu Ala Leu Glu Asn Lys Ile Ile
        35                  40

<210> SEQ ID NO 12
<211> LENGTH: 26
<212> TYPE: PRT
<213> ORGANISM: Artificial Sequence
<220> FEATURE:
<223> OTHER INFORMATION: Matrillin- 1 (short version)

<400> SEQUENCE: 12

Glu Glu Leu Ile Asn Thr Leu Gln Gln Lys Leu Glu Ala Val Ala Lys
1               5                   10                  15

Arg Ile Glu Ala Leu Glu Asn Lys Ile Ile
            20                  25

<210> SEQ ID NO 13
<211> LENGTH: 521
<212> TYPE: PRT
<213> ORGANISM: Artificial Sequence
<220> FEATURE:
<223> OTHER INFORMATION: F8: RSV A2, wt ectodomain

<400> SEQUENCE: 13

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

```
Met Gln Ser Thr Pro Ala Thr Asn Asn Arg Ala Arg Glu Leu Pro
            100                 105                 110

Arg Phe Met Asn Tyr Thr Leu Asn Ala Lys Lys Thr Asn Val Thr
            115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510
```

Leu His His His His His His
        515             520

<210> SEQ ID NO 14
<211> LENGTH: 521
<212> TYPE: PRT
<213> ORGANISM: Artificial Sequence
<220> FEATURE:
<223> OTHER INFORMATION: F11: RSV B1, wt ectodomain

<400> SEQUENCE: 14

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

```
Pro Gln Ala Asp Thr Cys Lys Val Gln Ser Asn Arg Val Phe Cys Asp
        355                 360                 365
Thr Met Asn Ser Leu Thr Leu Pro Ser Glu Val Ser Leu Cys Asn Thr
    370                 375                 380
Asp Ile Phe Asn Ser Lys Tyr Asp Cys Lys Ile Met Thr Ser Lys Thr
385                 390                 395                 400
Asp Ile Ser Ser Ser Val Ile Thr Ser Leu Gly Ala Ile Val Ser Cys
            405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Leu Glu Gly
    450                 455                 460
Lys Asn Leu Tyr Val Lys Gly Glu Pro Ile Ile Asn Tyr Tyr Asp Pro
465                 470                 475                 480
Leu Val Phe Pro Ser Asp Glu Phe Asp Ala Ser Ile Ser Gln Val Asn
            485                 490                 495
Glu Lys Ile Asn Gln Ser Leu Ala Phe Ile Arg Arg Ser Asp Glu Leu
            500                 505                 510
Leu His His His His His His His
        515                 520

<210> SEQ ID NO 15
<211> LENGTH: 507
<212> TYPE: PRT
<213> ORGANISM: Artificial Sequence
<220> FEATURE:
<223> OTHER INFORMATION: F47: RSV A2, linker stabilized, IZ(S)

<400> SEQUENCE: 15

Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu
        35                  40                  45
Arg Thr Gly Trp Tyr Thr Ser Val Ile Thr Ile Glu Leu Ser Asn Ile
    50                  55                  60
Lys Lys Asn Lys Cys Asn Gly Thr Asp Ala Lys Ile Lys Leu Ile Lys
65                  70                  75                  80
Gln Glu Leu Asp Lys Tyr Lys Asn Ala Val Thr Glu Leu Gln Leu Leu
            85                  90                  95
Met Gln Ser Thr Pro Ala Thr Asn Asn Gln Ala Arg Gly Ser Gly Ser
            100                 105                 110
Gly Arg Ser Leu Gly Phe Leu Leu Gly Val Gly Ser Ala Ile Ala Ser
        115                 120                 125
Gly Val Ala Val Ser Lys Val Leu His Leu Glu Gly Glu Val Asn Lys
    130                 135                 140
Ile Lys Ser Ala Leu Leu Ser Thr Asn Lys Ala Val Val Ser Leu Ser
145                 150                 155                 160
Asn Gly Val Ser Val Leu Thr Ser Lys Val Leu Asp Leu Lys Asn Tyr
            165                 170                 175
Ile Asp Lys Gln Leu Leu Pro Ile Val Asn Lys Gln Ser Cys Ser Ile
            180                 185                 190
```

```
Ser Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
                260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
        290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
                340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Glu Lys Lys Ile Glu Ala Ile
465                 470                 475                 480

Glu Lys Lys Ile Glu Ala Ile Glu Lys Lys Ile Glu Ala Gly Gly Ile
                485                 490                 495

Glu Gly Arg His His His His His His
        500                 505

<210> SEQ ID NO 16
<211> LENGTH: 495
<212> TYPE: PRT
<213> ORGANISM: Artificial Sequence
<220> FEATURE:
<223> OTHER INFORMATION: F47-: RSV A2, linker stabilized, IZ(S)

<400> SEQUENCE: 16

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45
```

```
Arg Thr Gly Trp Tyr Thr Ser Val Ile Thr Ile Glu Leu Ser Asn Ile
 50                  55                  60

Lys Lys Asn Lys Cys Asn Gly Thr Asp Ala Lys Ile Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Ser Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Glu Lys Lys Ile Glu Ala Ile
```

```
                465                 470                 475                 480
Glu Lys Lys Ile Glu Ala Ile Glu Lys Ile Glu Ala Gly Gly
                485                 490                 495

<210> SEQ ID NO 17
<211> LENGTH: 505
<212> TYPE: PRT
<213> ORGANISM: Artificial Sequence
<220> FEATURE:
<223> OTHER INFORMATION: F43: RSV B1, linker stabilized, IZ(S)

<400> SEQUENCE: 17

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Ile Ala Val Ser Lys Val Leu His Leu Glu Gly Glu Val Asn Lys
    130                 135                 140

Ile Lys Asn Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asn Asn Gln Leu Leu Pro Ile Val Asn Gln Gln Ser Cys Arg Ile
            180                 185                 190

Ser Asn Ile Glu Thr Val Ile Glu Phe Gln Gln Lys Asn Ser Arg Leu
        195                 200                 205

Leu Glu Ile Asn Arg Glu Phe Ser Val Asn Ala Gly Val Thr Thr Pro
    210                 215                 220

Leu Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Ser Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Ile Tyr Gly Val Ile Asp
        275                 280                 285

Thr Pro Cys Trp Lys Leu His Thr Ser Pro Leu Cys Thr Thr Asn Ile
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Asp Thr Cys
                325                 330                 335

Lys Val Gln Ser Asn Arg Val Phe Cys Asp Thr Met Asn Ser Leu Thr
```

```
                    340                 345                 350

Leu Pro Ser Glu Val Ser Leu Cys Asn Thr Asp Ile Phe Asn Ser Lys
            355                 360                 365

Tyr Asp Cys Lys Ile Met Thr Ser Lys Thr Asp Ile Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
            405                 410                 415

Cys Asp Tyr Val Ser Asn Lys Gly Val Asp Thr Val Ser Val Gly Asn
        420                 425                 430

Thr Leu Tyr Tyr Val Asn Lys Leu Glu Gly Lys Asn Leu Tyr Val Lys
            435                 440                 445

Gly Glu Pro Ile Ile Asn Tyr Tyr Asp Pro Leu Val Phe Pro Ser Asp
            450                 455                 460

Glu Phe Asp Ala Ser Ile Ser Gln Val Glu Lys Lys Ile Glu Ala Ile
465                 470                 475                 480

Glu Lys Lys Ile Glu Ala Ile Glu Lys Lys Ile Glu Ala Gly Gly Ile
            485                 490                 495

Glu Gly Arg His His His His His His
            500                 505

<210> SEQ ID NO 18
<211> LENGTH: 534
<212> TYPE: PRT
<213> ORGANISM: Artificial Sequence
<220> FEATURE:
<223> OTHER INFORMATION: F24: RSV B1, linker stabilized, fibritin

<400> SEQUENCE: 18

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Ile Ala Val Ser Lys Val Leu His Leu Glu Gly Glu Val Asn Lys
    130                 135                 140

Ile Lys Asn Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asn Asn Gln Leu Leu Pro Ile Val Asn Gln Gln Ser Cys Arg Ile
            180                 185                 190

Ser Asn Ile Glu Thr Val Ile Glu Phe Gln Gln Lys Asn Ser Arg Leu
```

```
            195                 200                 205
Leu Glu Ile Asn Arg Glu Phe Ser Val Asn Ala Gly Val Thr Thr Pro
    210                 215                 220

Leu Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Ser Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Ile Tyr Gly Val Ile Asp
        275                 280                 285

Thr Pro Cys Trp Lys Leu His Thr Ser Pro Leu Cys Thr Thr Asn Ile
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Asp Thr Cys
                325                 330                 335

Lys Val Gln Ser Asn Arg Val Phe Cys Asp Thr Met Asn Ser Leu Thr
            340                 345                 350

Leu Pro Ser Glu Val Ser Leu Cys Asn Thr Asp Ile Phe Asn Ser Lys
        355                 360                 365

Tyr Asp Cys Lys Ile Met Thr Ser Lys Thr Asp Ile Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Leu Glu Gly Lys Asn Leu Tyr Val Lys
        435                 440                 445

Gly Glu Pro Ile Ile Asn Tyr Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

His His His His His His
    530

<210> SEQ ID NO 19
<211> LENGTH: 528
<212> TYPE: PRT
<213> ORGANISM: Artificial Sequence
<220> FEATURE:
<223> OTHER INFORMATION: A2_F24: RSV A2, linker stabilized, fibritin

<400> SEQUENCE: 19

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
```

```
                    20                  25                  30
Tyr Gln Ser Thr Cys Ser Ala Val Ser Lys Gly Tyr Leu Ser Ala Leu
                35                  40                  45
Arg Thr Gly Trp Tyr Thr Ser Val Ile Thr Ile Glu Leu Ser Asn Ile
            50                  55                  60
Lys Lys Asn Lys Cys Asn Gly Thr Asp Ala Lys Ile Lys Leu Ile Lys
 65                 70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Gln Ala Arg Gly Ser Gly Ser
                100                 105                 110
Gly Arg Ser Leu Gly Phe Leu Leu Gly Val Gly Ser Ala Ile Ala Ser
            115                 120                 125
Gly Val Ala Val Ser Lys Val Leu His Leu Glu Gly Glu Val Asn Lys
            130                 135                 140
Ile Lys Ser Ala Leu Leu Ser Thr Asn Lys Ala Val Val Ser Leu Ser
145                 150                 155                 160
Asn Gly Val Ser Val Leu Thr Ser Lys Val Leu Asp Leu Lys Asn Tyr
                165                 170                 175
Ile Asp Lys Gln Leu Leu Pro Ile Val Asn Lys Gln Ser Cys Ser Ile
            180                 185                 190
Ser Asn Ile Glu Thr Val Ile Glu Phe Gln Gln Lys Asn Asn Arg Leu
            195                 200                 205
Leu Glu Ile Thr Arg Glu Phe Ser Val Asn Ala Gly Val Thr Thr Pro
            210                 215                 220
Val Ser Thr Tyr Met Leu Thr Asn Ser Glu Leu Leu Ser Leu Ile Asn
225                 230                 235                 240
Asp Met Pro Ile Thr Asn Asp Gln Lys Lys Leu Met Ser Asn Asn Val
                245                 250                 255
Gln Ile Val Arg Gln Gln Ser Tyr Ser Ile Met Ser Ile Ile Lys Glu
            260                 265                 270
Glu Val Leu Ala Tyr Val Val Gln Leu Pro Leu Tyr Gly Val Ile Asp
            275                 280                 285
Thr Pro Cys Trp Lys Leu His Thr Ser Pro Leu Cys Thr Thr Asn Thr
            290                 295                 300
Lys Glu Gly Ser Asn Ile Cys Leu Thr Arg Thr Asp Arg Gly Trp Tyr
305                 310                 315                 320
Cys Asp Asn Ala Gly Ser Val Ser Phe Phe Pro Gln Ala Glu Thr Cys
                325                 330                 335
Lys Val Gln Ser Asn Arg Val Phe Cys Asp Thr Met Asn Ser Leu Thr
                340                 345                 350
Leu Pro Ser Glu Val Asn Leu Cys Asn Val Asp Ile Phe Asn Pro Lys
            355                 360                 365
Tyr Asp Cys Lys Ile Met Thr Ser Lys Thr Asp Val Ser Ser Ser Val
            370                 375                 380
Ile Thr Ser Leu Gly Ala Ile Val Ser Cys Tyr Gly Lys Thr Lys Cys
385                 390                 395                 400
Thr Ala Ser Asn Lys Asn Arg Gly Ile Ile Lys Thr Phe Ser Asn Gly
                405                 410                 415
Cys Asp Tyr Val Ser Asn Lys Gly Val Asp Thr Val Ser Val Gly Asn
            420                 425                 430
Thr Leu Tyr Tyr Val Asn Lys Gln Glu Gly Lys Ser Leu Tyr Val Lys
            435                 440                 445
```

```
Gly Glu Pro Ile Ile Asn Phe Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
                515                 520                 525

<210> SEQ ID NO 20
<211> LENGTH: 528
<212> TYPE: PRT
<213> ORGANISM: Artificial Sequence
<220> FEATURE:
<223> OTHER INFORMATION: F24-: RSV B1, linker stabilized, fibritin

<400> SEQUENCE: 20

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
                20                  25                  30

Tyr Gln Ser Thr Cys Ser Ala Val Ser Arg Gly Tyr Phe Ser Ala Leu
            35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Ile Ala Val Ser Lys Val Leu His Leu Glu Gly Glu Val Asn Lys
    130                 135                 140

Ile Lys Asn Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asn Asn Gln Leu Leu Pro Ile Val Asn Gln Gln Ser Cys Arg Ile
            180                 185                 190

Ser Asn Ile Glu Thr Val Ile Glu Phe Gln Gln Lys Asn Ser Arg Leu
        195                 200                 205

Leu Glu Ile Asn Arg Glu Phe Ser Val Asn Ala Gly Val Thr Thr Pro
    210                 215                 220

Leu Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Ser Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Ile Tyr Gly Val Ile Asp
        275                 280                 285
```

Thr Pro Cys Trp Lys Leu His Thr Ser Pro Leu Cys Thr Thr Asn Ile
            290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Asp Thr Cys
                325                 330                 335

Lys Val Gln Ser Asn Arg Val Phe Cys Asp Thr Met Asn Ser Leu Thr
            340                 345                 350

Leu Pro Ser Glu Val Ser Leu Cys Asn Thr Asp Ile Phe Asn Ser Lys
        355                 360                 365

Tyr Asp Cys Lys Ile Met Thr Ser Lys Thr Asp Ile Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Leu Glu Gly Lys Asn Leu Tyr Val Lys
        435                 440                 445

Gly Glu Pro Ile Ile Asn Tyr Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 21
<211> LENGTH: 528
<212> TYPE: PRT
<213> ORGANISM: Artificial Sequence
<220> FEATURE:
<223> OTHER INFORMATION: A2_F24 N67I+S215P: A2, linker stabilized,
      fibritin

<400> SEQUENCE: 21

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser

```
            115                 120                 125
Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 22
```

```
<211> LENGTH: 528
<212> TYPE: PRT
<213> ORGANISM: Artificial Sequence
<220> FEATURE:
<223> OTHER INFORMATION: F24-N67I+S215P: RSV B1, linker stabilized,
      fibritin (

<400> SEQUENCE: 22
```

| Met<br>1 | Glu | Leu | Leu | Ile<br>5 | His | Arg | Leu | Ser | Ala<br>10 | Ile | Phe | Leu | Thr | Leu<br>15 | Ala |
|---|---|---|---|---|---|---|---|---|---|---|---|---|---|---|---|
| Ile | Asn | Ala | Leu<br>20 | Tyr | Leu | Thr | Ser<br>25 | Ser | Gln | Asn | Ile | Thr<br>30 | Glu | Glu | Phe |
| Tyr | Gln | Ser<br>35 | Thr | Cys | Ser | Ala | Val<br>40 | Ser | Arg | Gly | Tyr | Phe<br>45 | Ser | Ala | Leu |
| Arg | Thr<br>50 | Gly | Trp | Tyr | Thr | Ser<br>55 | Val | Ile | Thr | Ile | Glu<br>60 | Leu | Ser | Asn | Ile |
| Lys<br>65 | Glu | Ile | Lys | Cys | Asn<br>70 | Gly | Thr | Asp | Thr | Lys<br>75 | Val | Lys | Leu | Ile | Lys<br>80 |
| Gln | Glu | Leu | Asp | Lys<br>85 | Tyr | Lys | Asn | Ala | Val<br>90 | Thr | Glu | Leu | Gln | Leu<br>95 | Leu |
| Met | Gln | Asn | Thr<br>100 | Pro | Ala | Ala | Asn | Asn<br>105 | Gln | Ala | Arg | Gly | Ser<br>110 | Gly | Ser |
| Gly | Arg | Ser<br>115 | Leu | Gly | Phe | Leu | Leu<br>120 | Gly | Val | Gly | Ser | Ala<br>125 | Ile | Ala | Ser |
| Gly | Ile<br>130 | Ala | Val | Ser | Lys | Val<br>135 | Leu | His | Leu | Glu | Gly<br>140 | Glu | Val | Asn | Lys |
| Ile<br>145 | Lys | Asn | Ala | Leu | Leu<br>150 | Ser | Thr | Asn | Lys | Ala<br>155 | Val | Val | Ser | Leu | Ser<br>160 |
| Asn | Gly | Val | Ser | Val<br>165 | Leu | Thr | Ser | Lys | Val<br>170 | Leu | Asp | Leu | Lys | Asn<br>175 | Tyr |
| Ile | Asn | Asn | Gln<br>180 | Leu | Leu | Pro | Ile | Val<br>185 | Asn | Gln | Gln | Ser | Cys<br>190 | Arg | Ile |
| Pro | Asn | Ile<br>195 | Glu | Thr | Val | Ile | Glu<br>200 | Phe | Gln | Gln | Lys | Asn<br>205 | Ser | Arg | Leu |
| Leu | Glu<br>210 | Ile | Asn | Arg | Glu | Phe<br>215 | Ser | Val | Asn | Ala | Gly<br>220 | Val | Thr | Thr | Pro |
| Leu<br>225 | Ser | Thr | Tyr | Met | Leu<br>230 | Thr | Asn | Ser | Glu | Leu<br>235 | Leu | Ser | Leu | Ile | Asn<br>240 |
| Asp | Met | Pro | Ile | Thr<br>245 | Asn | Asp | Gln | Lys | Lys<br>250 | Leu | Met | Ser | Ser | Asn<br>255 | Val |
| Gln | Ile | Val | Arg<br>260 | Gln | Gln | Ser | Tyr | Ser<br>265 | Ile | Met | Ser | Ile | Ile<br>270 | Lys | Glu |
| Glu | Val | Leu<br>275 | Ala | Tyr | Val | Val | Gln<br>280 | Leu | Pro | Ile | Tyr | Gly<br>285 | Val | Ile | Asp |
| Thr | Pro<br>290 | Cys | Trp | Lys | Leu | His<br>295 | Thr | Ser | Pro | Leu | Cys<br>300 | Thr | Thr | Asn | Ile |
| Lys<br>305 | Glu | Gly | Ser | Asn | Ile<br>310 | Cys | Leu | Thr | Arg | Thr<br>315 | Asp | Arg | Gly | Trp | Tyr<br>320 |
| Cys | Asp | Asn | Ala | Gly<br>325 | Ser | Val | Ser | Phe | Phe<br>330 | Pro | Gln | Ala | Asp | Thr<br>335 | Cys |
| Lys | Val | Gln | Ser<br>340 | Asn | Arg | Val | Phe | Cys<br>345 | Asp | Thr | Met | Asn | Ser<br>350 | Leu | Thr |
| Leu | Pro | Ser<br>355 | Glu | Val | Ser | Leu | Cys<br>360 | Asn | Thr | Asp | Ile | Phe<br>365 | Asn | Ser | Lys |
| Tyr | Asp | Cys | Lys | Ile | Met | Thr | Ser | Lys | Thr | Asp | Ile | Ser | Ser | Ser | Val |

```
            370                 375                 380
Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Leu Glu Gly Lys Asn Leu Tyr Val Lys
                435                 440                 445

Gly Glu Pro Ile Ile Asn Tyr Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
            515                 520                 525

<210> SEQ ID NO 23
<211> LENGTH: 528
<212> TYPE: PRT
<213> ORGANISM: Artificial Sequence
<220> FEATURE:
<223> OTHER INFORMATION: A2_F24 N67I+E92D: RSV A2, linker stabilized,
      fibritin

<400> SEQUENCE: 23

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Asn Asn Gln Ala Arg Gly Ser Gly Ser
                100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
        130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
                180                 185                 190

Ser Asn Ile Glu Thr Val Ile Glu Phe Gln Gln Lys Asn Asn Arg Leu
            195                 200                 205
```

Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
            245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
            515                 520                 525

<210> SEQ ID NO 24
<211> LENGTH: 528
<212> TYPE: PRT
<213> ORGANISM: Artificial Sequence
<220> FEATURE:
<223> OTHER INFORMATION: F24- N67I+E92D RSV B1, linker stabilized,
      fibritin

<400> SEQUENCE: 24

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
            35                  40                  45

```
Arg Thr Gly Trp Tyr Thr Ser Val Ile Thr Ile Glu Leu Ser Asn Ile
 50                  55                  60

Lys Glu Ile Lys Cys Asn Gly Thr Asp Thr Lys Val Lys Leu Ile Lys
 65                  70                  75                  80

Gln Glu Leu Asp Lys Tyr Lys Asn Ala Val Thr Asp Leu Gln Leu Leu
                 85                  90                  95

Met Gln Asn Thr Pro Ala Ala Asn Asn Gln Ala Arg Gly Ser Gly Ser
                100                 105                 110

Gly Arg Ser Leu Gly Phe Leu Leu Gly Val Gly Ser Ala Ile Ala Ser
                115                 120                 125

Gly Ile Ala Val Ser Lys Val Leu His Leu Glu Gly Glu Val Asn Lys
    130                 135                 140

Ile Lys Asn Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asn Asn Gln Leu Leu Pro Ile Val Asn Gln Gln Ser Cys Arg Ile
                180                 185                 190

Ser Asn Ile Glu Thr Val Ile Glu Phe Gln Gln Lys Asn Ser Arg Leu
    195                 200                 205

Leu Glu Ile Asn Arg Glu Phe Ser Val Asn Ala Gly Val Thr Thr Pro
210                 215                 220

Leu Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Ser Asn Val
                245                 250                 255

Gln Ile Val Arg Gln Gln Ser Tyr Ser Ile Met Ser Ile Ile Lys Glu
                260                 265                 270

Glu Val Leu Ala Tyr Val Val Gln Leu Pro Ile Tyr Gly Val Ile Asp
    275                 280                 285

Thr Pro Cys Trp Lys Leu His Thr Ser Pro Leu Cys Thr Thr Asn Ile
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Asp Thr Cys
                325                 330                 335

Lys Val Gln Ser Asn Arg Val Phe Cys Asp Thr Met Asn Ser Leu Thr
                340                 345                 350

Leu Pro Ser Glu Val Ser Leu Cys Asn Thr Asp Ile Phe Asn Ser Lys
    355                 360                 365

Tyr Asp Cys Lys Ile Met Thr Ser Lys Thr Asp Ile Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Leu Glu Gly Lys Asn Leu Tyr Val Lys
    435                 440                 445

Gly Glu Pro Ile Ile Asn Tyr Tyr Asp Pro Leu Val Phe Pro Ser Asp
450                 455                 460
```

```
Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
            515                 520                 525

<210> SEQ ID NO 25
<211> LENGTH: 528
<212> TYPE: PRT
<213> ORGANISM: Artificial Sequence
<220> FEATURE:
<223> OTHER INFORMATION: A2_F24 N67I+K465Q RSV A2, linker stabilized,
      fibritin

<400> SEQUENCE: 25

Met Glu Leu Leu Ile Leu Lys Ala Asn Ala Ile Thr Thr Ile Leu Thr
1               5                   10                  15

Ala

```
Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
                340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Gln Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 26
<211> LENGTH: 528
<212> TYPE: PRT
<213> ORGANISM: Artificial Sequence
<220> FEATURE:
<223> OTHER INFORMATION: F24- N67I+K465Q RSV B1, linker stabilized,
      fibritin

<400> SEQUENCE: 26

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Ile Ala Val Ser Lys Val Leu His Leu Glu Gly Glu Val Asn Lys
```

```
              130                 135                 140
Ile Lys Asn Ala Leu Leu Ser Thr Asn Lys Ala Val Ser Leu Ser
145                 150                 155                 160

Asn Gly Val Ser Val Leu Thr Ser Lys Val Leu Asp Leu Lys Asn Tyr
                165                 170                 175

Ile Asn Asn Gln Leu Leu Pro Ile Val Asn Gln Gln Ser Cys Arg Ile
            180                 185                 190

Pro Asn Ile Glu Thr Val Ile Glu Phe Gln Gln Lys Asn Ser Arg Leu
                195                 200                 205

Leu Glu Ile Asn Arg Glu Phe Ser Val Asn Ala Gly Val Thr Thr Pro
210                 215                 220

Leu Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Ser Asn Val
                245                 250                 255

Gln Ile Val Arg Gln Gln Ser Tyr Ser Ile Met Ser Ile Ile Lys Glu
                260                 265                 270

Glu Val Leu Ala Tyr Val Val Gln Leu Pro Ile Tyr Gly Val Ile Asp
            275                 280                 285

Thr Pro Cys Trp Lys Leu His Thr Ser Pro Leu Cys Thr Thr Asn Ile
        290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Asp Thr Cys
                325                 330                 335

Lys Val Gln Ser Asn Arg Val Phe Cys Asp Thr Met Asn Ser Leu Thr
                340                 345                 350

Leu Pro Ser Glu Val Ser Leu Cys Asn Thr Asp Ile Phe Asn Ser Lys
            355                 360                 365

Tyr Asp Cys Lys Ile Met Thr Ser Lys Thr Asp Ile Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Leu Glu Gly Gln Asn Leu Tyr Val Lys
            435                 440                 445

Gly Glu Pro Ile Ile Asn Tyr Tyr Asp Pro Leu Val Phe Pro Ser Asp
        450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
            515                 520                 525

<210> SEQ ID NO 27
<211> LENGTH: 528
<212> TYPE: PRT
<213> ORGANISM: Artificial Sequence
```

<220> FEATURE:
<223> OTHER INFORMATION: A2_F24 N67I+S46G RSV A2, linker stabilized, fibritin

<400> SEQUENCE: 27

| Met | Glu | Leu | Leu | Ile | Leu | Lys | Ala | As

```
                385                 390                 395                 400
        Thr Ala Ser Asn Lys Asn Arg Gly Ile Ile Lys Thr Phe Ser Asn Gly
                        405                 410                 415

Cys Asp Tyr Val Ser Asn Lys Gly Val Asp Thr Val Ser Val Gly Asn
                        420                 425                 430

Thr Leu Tyr Tyr Val Asn Lys Gln Glu Gly Lys Ser Leu Tyr Val Lys
                        435                 440                 445

Gly Glu Pro Ile Ile Asn Phe Tyr Asp Pro Leu Val Phe Pro Ser Asp
                        450                 455                 460

Glu Phe Asp Ala Ser Ile Ser Gln Val Asn Glu Lys Ile Asn Gln Ser
        465                 470                 475                 480

Leu Ala Phe Ile Arg Lys Ser Asp Glu Leu Leu Ser Ala Ile Gly Gly
                        485                 490                 495

Tyr Ile Pro Glu Ala Pro Arg Asp Gly Gln Ala Tyr Val Arg Lys Asp
                        500                 505                 510

Gly Glu Trp Val Leu Leu Ser Thr Phe Leu Gly Gly Ile Glu Gly Arg
                        515                 520                 525

<210> SEQ ID NO 28
<211> LENGTH: 528
<212> TYPE: PRT
<213> ORGANISM: Artificial Sequence
<220> FEATURE:
<223> OTHER INFORMATION: F24- N67I+S46G RSV B1, linker stabilized,
      fibritin

<400> SEQUENCE: 28

Met Glu Leu Leu Ile His Arg Leu Ser Ala Ile Phe Leu Thr Leu Ala
        1               5                   10                  15

Ile Asn Ala Leu Tyr Leu Thr Ser Ser Gln Asn Ile Thr Glu Glu Phe
                        20                  25                  30

Tyr Gln Ser Thr Cys Ser Ala Val Ser Arg Gly Tyr Phe Gly Ala Leu
                        35                  40                  45

Arg Thr Gly Trp Tyr Thr Ser Val Ile Thr Ile Glu Leu Ser Asn Ile
        50                  55                  60

Lys Glu Ile Lys Cys Asn Gly Thr Asp Thr Lys Val Lys Leu Ile Lys
        65                  70                  75                  80

Gln Glu Leu Asp Lys Tyr Lys Asn Ala Val Thr Asp Leu Gln Leu Leu
                        85                  90                  95

Met Gln Asn Thr Pro Ala Ala Asn Asn Gln Ala Arg Gly Ser Gly Ser
                        100                 105                 110

Gly Arg Ser Leu Gly Phe Leu Leu Gly Val Gly Ser Ala Ile Ala Ser
                        115                 120                 125

Gly Ile Ala Val Ser Lys Val Leu His Leu Glu Gly Glu Val Asn Lys
                        130                 135                 140

Ile Lys Asn Ala Leu Leu Ser Thr Asn Lys Ala Val Val Ser Leu Ser
        145                 150                 155                 160

Asn Gly Val Ser Val Leu Thr Ser Lys Val Leu Asp Leu Lys Asn Tyr
                        165                 170                 175

Ile Asn Asn Gln Leu Leu Pro Ile Val Asn Gln Gln Ser Cys Arg Ile
                        180                 185                 190

Ser Asn Ile Glu Thr Val Ile Glu Phe Gln Gln Lys Asn Ser Arg Leu
                        195                 200                 205

Leu Glu Ile Asn Arg Glu Phe Ser Val Asn Ala Gly Val Thr Thr Pro
        210                 215                 220
```

```
Leu Ser Thr Tyr Met Leu Thr Asn Ser Glu Leu Ser Leu Ile Asn
225                 230                 235                 240

Asp Met Pro Ile Thr Asn Asp Gln Lys Lys Leu Met Ser Ser Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Ile Tyr Gly Val Ile Asp
        275                 280                 285

Thr Pro Cys Trp Lys Leu His Thr Ser Pro Leu Cys Thr Thr Asn Ile
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Asp Thr Cys
                325                 330                 335

Lys Val Gln Ser Asn Arg Val Phe Cys Asp Thr Met Asn Ser Leu Thr
            340                 345                 350

Leu Pro Ser Glu Val Ser Leu Cys Asn Thr Asp Ile Phe Asn Ser Lys
        355                 360                 365

Tyr Asp Cys Lys Ile Met Thr Ser Lys Thr Asp Ile Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Leu Glu Gly Lys Asn Leu Tyr Val Lys
        435                 440                 445

Gly Glu Pro Ile Ile Asn Tyr Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 29
<211> LENGTH: 528
<212> TYPE: PRT
<213> ORGANISM: Artificial Sequence
<220> FEATURE:
<223> OTHER INFORMATION: A2_F24 E92D+S215P: A2, linker stabilized,
      fibritin

<400> SEQUENCE: 29

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60
```

```
Lys Lys Asn Lys Cys Asn Gly Thr Asp Ala Lys Ile Lys Leu Ile Lys
 65                  70                  75                  80

Gln Glu Leu Asp Lys Tyr Lys Asn Ala Val Thr Asp Leu Gln Leu Leu
                 85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480
```

```
Leu Ala Phe Ile Arg Lys Ser Asp Glu Leu Ser Ala Ile Gly Gly
                485                 490                 495
Tyr Ile Pro Glu Ala Pro Arg Asp Gly Gln Ala Tyr Val Arg Lys Asp
            500                 505                 510
Gly Glu Trp Val Leu Leu Ser Thr Phe Leu Gly Gly Ile Glu Gly Arg
        515                 520                 525

<210> SEQ ID NO 30
<211> LENGTH: 528
<212> TYPE: PRT
<213> ORGANISM: Artificial Sequence
<220> FEATURE:
<223> OTHER INFORMATION: F24-E92D+S215P: RSV B1, linker stabilized,
      fibritin

<400> SEQUENCE: 30

Met Glu Leu Leu Ile His Arg Leu Ser Ala Ile Phe Leu Thr Leu Ala
1               5                   10                  15
Ile Asn Ala Leu Tyr Leu Thr Ser Ser Gln Asn Ile Thr Glu Glu Phe
            20                  25                  30
Tyr Gln Ser Thr Cys Ser Ala Val Ser Arg Gly Tyr Phe Ser Ala Leu
        35                  40                  45
Arg Thr Gly Trp Tyr Thr Ser Val Ile Thr Ile Glu Leu Ser Asn Ile
    50                  55                  60
Lys Glu Thr Lys Cys Asn Gly Thr Asp Thr Lys Val Lys Leu Ile Lys
65                  70                  75                  80
Gln Glu Leu Asp Lys Tyr Lys Asn Ala Val Thr Asp Leu Gln Leu Leu
                85                  90                  95
Met Gln Asn Thr Pro Ala Ala Asn Asn Gln Ala Arg Gly Ser Gly Ser
            100                 105                 110
Gly Arg Ser Leu Gly Phe Leu Leu Gly Val Gly Ser Ala Ile Ala Ser
        115                 120                 125
Gly Ile Ala Val Ser Lys Val Leu His Leu Glu Gly Glu Val Asn Lys
    130                 135                 140
Ile Lys Asn Ala Leu Leu Ser Thr Asn Lys Ala Val Val Ser Leu Ser
145                 150                 155                 160
Asn Gly Val Ser Val Leu Thr Ser Lys Val Leu Asp Leu Lys Asn Tyr
                165                 170                 175
Ile Asn Asn Gln Leu Leu Pro Ile Val Asn Gln Gln Ser Cys Arg Ile
            180                 185                 190
Pro Asn Ile Glu Thr Val Ile Glu Phe Gln Gln Lys Asn Ser Arg Leu
        195                 200                 205
Leu Glu Ile Asn Arg Glu Phe Ser Val Asn Ala Gly Val Thr Thr Pro
    210                 215                 220
Leu Ser Thr Tyr Met Leu Thr Asn Ser Glu Leu Leu Ser Leu Ile Asn
225                 230                 235                 240
Asp Met Pro Ile Thr Asn Asp Gln Lys Lys Leu Met Ser Ser Asn Val
                245                 250                 255
Gln Ile Val Arg Gln Gln Ser Tyr Ser Ile Met Ser Ile Ile Lys Glu
            260                 265                 270
Glu Val Leu Ala Tyr Val Val Gln Leu Pro Ile Tyr Gly Val Ile Asp
        275                 280                 285
Thr Pro Cys Trp Lys Leu His Thr Ser Pro Leu Cys Thr Thr Asn Ile
    290                 295                 300
Lys Glu Gly Ser Asn Ile Cys Leu Thr Arg Thr Asp Arg Gly Trp Tyr
305                 310                 315                 320
```

```
Cys Asp Asn Ala Gly Ser Val Ser Phe Phe Pro Gln Ala Asp Thr Cys
                325                 330                 335

Lys Val Gln Ser Asn Arg Val Phe Cys Asp Thr Met Asn Ser Leu Thr
            340                 345                 350

Leu Pro Ser Glu Val Ser Leu Cys Asn Thr Asp Ile Phe Asn Ser Lys
        355                 360                 365

Tyr Asp Cys Lys Ile Met Thr Ser Lys Thr Asp Ile Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Leu Glu Gly Lys Asn Leu Tyr Val Lys
        435                 440                 445

Gly Glu Pro Ile Ile Asn Tyr Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Arg Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 31
<211> LENGTH: 528
<212> TYPE: PRT
<213> ORGANISM: Artificial Sequence
<220> FEATURE:
<223> OTHER INFORMATION: A2_F24 N67I+S215P+K508E: A2, linker stabilized,
      fibritin

<400> SEQUENCE: 31

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
```

```
              145                 150                 155                 160
Asn Gly Val Ser Val Leu Thr Ser Lys Val Leu Asp Leu Lys Asn Tyr
                    165                 170                 175

Ile Asp Lys Gln Leu Leu Pro Ile Val Asn Lys Gln Ser Cys Ser Ile
                    180                 185                 190

Pro Asn Ile Glu Thr Val Ile Glu Phe Gln Gln Lys Asn Asn Arg Leu
                    195                 200                 205

Leu Glu Ile Thr Arg Glu Phe Ser Val Asn Ala Gly Val Thr Thr Pro
        210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                    245                 250                 255

Gln Ile Val Arg Gln Gln Ser Tyr Ser Ile Met Ser Ile Ile Lys Glu
                    260                 265                 270

Glu Val Leu Ala Tyr Val Val Gln Leu Pro Leu Tyr Gly Val Ile Asp
                    275                 280                 285

Thr Pro Cys Trp Lys Leu His Thr Ser Pro Leu Cys Thr Thr Asn Thr
        290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                    325                 330                 335

Lys Val Gln Ser Asn Arg Val Phe Cys Asp Thr Met Asn Ser Leu Thr
                    340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
                    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                    405                 410                 415

Cys Asp Tyr Val Ser Asn Lys Gly Val Asp Thr Val Ser Val Gly Asn
                    420                 425                 430

Thr Leu Tyr Tyr Val Asn Lys Gln Glu Gly Lys Ser Leu Tyr Val Lys
                    435                 440                 445

Gly Glu Pro Ile Ile Asn Phe Tyr Asp Pro Leu Val Phe Pro Ser Asp
        450                 455                 460

Glu Phe Asp Ala Ser Ile Ser Gln Val Asn Glu Lys Ile Asn Gln Ser
465                 470                 475                 480

Leu Ala Phe Ile Arg Glu Ser Asp Glu Leu Leu Ser Ala Ile Gly Gly
                    485                 490                 495

Tyr Ile Pro Glu Ala Pro Arg Asp Gly Gln Ala Tyr Val Arg Lys Asp
                    500                 505                 510

Gly Glu Trp Val Leu Leu Ser Thr Phe Leu Gly Gly Ile Glu Gly Arg
            515                 520                 525

<210> SEQ ID NO 32
<211> LENGTH: 528
<212> TYPE: PRT
<213> ORGANISM: Artificial Sequence
<220> FEATURE:
<223> OTHER INFORMATION: A2_F24 N67I+S215P+E487I: A2, linker stabilized,
      fibritin
```

<400> SEQUENCE: 32

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly

```
                    405                 410                 415
Cys Asp Tyr Val Ser Asn Lys Gly Val Asp Thr Val Ser Val Gly Asn
                420                 425                 430

Thr Leu Tyr Tyr Val Asn Lys Gln Glu Gly Lys Ser Leu Tyr Val Lys
                435                 440                 445

Gly Glu Pro Ile Ile Asn Phe Tyr Asp Pro Leu Val Phe Pro Ser Asp
        450                 455                 460

Ile Phe Asp Ala Ser Ile Ser Gln Val Asn Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
            515                 520                 525

<210> SEQ ID NO 33
<211> LENGTH: 528
<212> TYPE: PRT
<213> ORGANISM: Artificial Sequence
<220> FEATURE:
<223> OTHER INFORMATION: A2_F24 N67I+S215P+E487Q: A2, linker stabilized,
      fibritin

<400> SEQUENCE: 33

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240
```

```
Asp Met Pro Ile Thr Asn Asp Gln Lys Lys Leu Met Ser Asn Asn Val
            245                 250                 255

Gln Ile Val Arg Gln Gln Ser Tyr Ser Ile Met Ser Ile Ile Lys Glu
        260                 265                 270

Glu Val Leu Ala Tyr Val Val Gln Leu Pro Leu Tyr Gly Val Ile Asp
    275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Gln Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 34
<211> LENGTH: 528
<212> TYPE: PRT
<213> ORGANISM: Artificial Sequence
<220> FEATURE:
<223> OTHER INFORMATION: A2_F24 N67I+S215P+E487N: A2, linker stabilized,
      fibritin

<400> SEQUENCE: 34

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80
```

```
Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Asn Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495
```

```
Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 35
<211> LENGTH: 528
<212> TYPE: PRT
<213> ORGANISM: Artificial Sequence
<220> FEATURE:
<223> OTHER INFORMATION: A2_F24 N67I+S215P+D486N: A2, linker stabilized,
      fibritin

<400> SEQUENCE: 35

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335
```

```
Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
            370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
            405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asn
            450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
            485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
            515                 520                 525

<210> SEQ ID NO 36
<211> LENGTH: 528
<212> TYPE: PRT
<213> ORGANISM: Artificial Sequence
<220> FEATURE:
<223> OTHER INFORMATION: A2_F24 N67I+S215P+K465E: A2, linker stabilized,
      fibritin

<400> SEQUENCE: 36

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
            85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
            130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
```

```
            165                 170                 175
Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Glu Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 37
<211> LENGTH: 528
<212> TYPE: PRT
<213> ORGANISM: Artificial Sequence
<220> FEATURE:
<223> OTHER INFORMATION: A2_F24 N67I+S215P+K465Q: A2, linker stabilized,
      fibritin

<400> SEQUENCE: 37
```

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
            165                 170                 175

Ile Asp Lys Gln Leu Leu Pro Ile Val Asn Lys Gln Ser Cys Ser Ile
        180                 185                 190

Pro Asn Ile Glu Thr Val Ile Glu Phe Gln Gln Lys Asn Asn Arg Leu
    195                 200                 205

Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
            245                 250                 255

Gln Ile Val Arg Gln Gln Ser Tyr Ser Ile Met Ser Ile Ile Lys Glu
        260                 265                 270

Glu Val Leu Ala Tyr Val Val Gln Leu Pro Leu Tyr Gly Val Ile Asp
    275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
            325                 330                 335

Lys Val Gln Ser Asn Arg Val Phe Cys Asp Thr Met Asn Ser Leu Thr
        340                 345                 350

Leu Pro Ser Glu Val Asn Leu Cys Asn Val Asp Ile Phe Asn Pro Lys
    355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
            405                 410                 415

Cys Asp Tyr Val Ser Asn Lys Gly Val Asp Thr Val Ser Val Gly Asn
```

```
                     420                 425                 430
Thr Leu Tyr Tyr Val Asn Lys Gln Glu Gly Gln Ser Leu Tyr Val Lys
            435                 440                 445

Gly Glu Pro Ile Ile Asn Phe Tyr Asp Pro Leu Val Phe Pro Ser Asp
        450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 38
<211> LENGTH: 528
<212> TYPE: PRT
<213> ORGANISM: Artificial Sequence
<220> FEATURE:
<223> OTHER INFORMATION: A2_F24 N67I+S215P+N426S: A2, linker stabilized,
      fibritin

<400> SEQUENCE: 38

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255
```

```
Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
            325                 330                 335

Lys Val Gln Ser Asn Arg Val Phe Cys Asp Thr Met Asn Ser Leu Thr
        340                 345                 350

Leu Pro Ser Glu Val Asn Leu Cys Asn Val Asp Ile Phe Asn Pro Lys
    355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Ser Lys Asn Arg Gly Ile Ile Lys Thr Phe Ser Asn Gly
            405                 410                 415

Cys Asp Tyr Val Ser Asn Lys Gly Val Asp Thr Val Ser Val Gly Asn
        420                 425                 430

Thr Leu Tyr Tyr Val Asn Lys Gln Glu Gly Lys Ser Leu Tyr Val Lys
    435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
            485                 490                 495

Tyr Ile Pro Glu Ala Pro Arg Asp Gly Gln Ala Tyr Val Arg Lys Asp
        500                 505                 510

Gly Glu Trp Val Leu Leu Ser Thr Phe Leu Gly Gly Ile Glu Gly Arg
    515                 520                 525

<210> SEQ ID NO 39
<211> LENGTH: 528
<212> TYPE: PRT
<213> ORGANISM: Artificial Sequence
<220> FEATURE:
<223> OTHER INFORMATION: A2_F24 N67I+S215P+K421N: A2, linker stabilized,
      fibritin

<400> SEQUENCE: 39

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
            85                  90                  95
```

```
Met Gln Ser Thr Pro Ala Thr Asn Asn Gln Ala Arg Gly Ser Gly Ser
                100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
        130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
                180                 185                 190

Pro Asn Ile Glu Thr Val Ile Glu Phe Gln Gln Lys Asn Asn Arg Leu
                195                 200                 205

Leu Glu Ile Thr Arg Glu Phe Ser Val Asn Ala Gly Val Thr Thr Pro
            210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
                260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
            290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
                340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
            370                 375                 380

Ile Thr Ser Leu Gly Ala Ile Val Ser Cys Tyr Gly Lys Thr Asn Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510
```

-continued

```
Gly Glu Trp Val Leu Leu Ser Thr Phe Leu Gly Gly Ile Glu Gly Arg
            515                 520                 525

<210> SEQ ID NO 40
<211> LENGTH: 528
<212> TYPE: PRT
<213> ORGANISM: Artificial Sequence
<220> FEATURE:
<223> OTHER INFORMATION: A2_F24 N67I+S215P+K209Q: A2, linker stabilized,
      fibritin

<400> SEQUENCE: 40

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Gln Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350
```

```
Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
            515                 520                 525

<210> SEQ ID NO 41
<211> LENGTH: 528
<212> TYPE: PRT
<213> ORGANISM: Artificial Sequence
<220> FEATURE:
<223> OTHER INFORMATION: A2_F24 N67I+S215P+K201Q: A2, linker stabilized,
      fibritin

<400> SEQUENCE: 41

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Gln Gln Leu Leu Pro Ile Val Asn Lys Gln Ser Cys Ser Ile
```

```
                 180                 185                 190
Pro Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
            210                 215                 220

Val Ser Thr Tyr Met Leu Thr Asn Ser Glu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
            290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
            370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
            515                 520                 525

<210> SEQ ID NO 42
<211> LENGTH: 528
<212> TYPE: PRT
<213> ORGANISM: Artificial Sequence
<220> FEATURE:
<223> OTHER INFORMATION: A2_F24 N67I+S215P+V185N: A2, linker stabilized,
      fibritin

<400> SEQUENCE: 42

Met Glu Leu Leu Ile Leu Lys Ala Asn Ala Ile Thr Thr Ile Leu Thr
1               5                   10                  15
```

```
Ala Val Thr Phe Cys Phe Ala Ser Gly Gln Asn Ile Thr Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
 50                      55                  60

Lys Lys Ile Lys Cys Asn Gly Thr Asp Ala Lys Ile Lys Leu Ile Lys
 65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Asn Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
```

```
                   435                 440                 445
Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525

<210> SEQ ID NO 43
<211> LENGTH: 528
<212> TYPE: PRT
<213> ORGANISM: Artificial Sequence
<220> FEATURE:
<223> OTHER INFORMATION: A2_F24 N67I+S215P+G184N: A2, linker stabilized,
      fibritin

<400> SEQUENCE: 43

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Asn Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270
```

```
Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
                340                 345                 350

Leu Pro Ser Glu Val Asn Leu Cys Asn Val Asp Ile Phe Asn Pro Lys
                355                 360                 365

Tyr Asp Cys Lys Ile Met Thr Ser Lys Thr Asp Val Ser Ser Ser Val
            370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
            515                 520                 525

<210> SEQ ID NO 44
<211> LENGTH: 528
<212> TYPE: PRT
<213> ORGANISM: Artificial Sequence
<220> FEATURE:
<223> OTHER INFORMATION: A2_F24 N67I+S215P+N175P: A2, linker stabilized,
      fibritin

<400> SEQUENCE: 44

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
                100                 105                 110
```

```
Gly Arg Ser Leu Gly Phe Leu Gly Val Gly Ser Ala Ile Ala Ser
            115                 120                 125

Gly Val Ala Val Ser Lys Val Leu His Leu Glu Gly Glu Val Asn Lys
        130                 135                 140

Ile Lys Ser Ala Leu Leu Ser Thr Pro Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525
```

```
<210> SEQ ID NO 45
<211> LENGTH: 528
<212> TYPE: PRT
<213> ORGANISM: Artificial Sequence
<220> FEATURE:
<223> OTHER INFORMATION: A2_F24 N67I+S215P+E92D: A2, linker stabilized,
      fibritin

<400> SEQUENCE: 45
```

| | | | | | | | | | | | | | | |
|---|---|---|---|---|---|---|---|---|---|---|---|---|---|---|
| Met | Glu | Leu | Leu | Ile | Leu | Lys | Ala | Asn | Ala | Ile | Thr | Thr | Ile | Leu | Thr |
| 1 | | | | 5 | | | | | 10 | | | | | 15 | |
| Ala | Val | Thr | Phe | Cys | Phe | Ala | Ser | Gly | Gln | Asn | Ile | Thr | Glu | Glu | Phe |
| | | 20 | | | | | 25 | | | | | 30 | | | |
| Tyr | Gln | Ser | Thr | Cys | Ser | Ala | Val | Ser | Lys | Gly | Tyr | Leu | Ser | Ala | Leu |
| | | | 35 | | | | | 40 | | | | | 45 | | |
| Arg | Thr | Gly | Trp | Tyr | Thr | Ser | Val | Ile | Thr | Ile | Glu | Leu | Ser | Asn | Ile |
| | 50 | | | | | 55 | | | | | 60 | | | | |
| Lys | Lys | Ile | Lys | Cys | Asn | Gly | Thr | Asp | Ala | Lys | Ile | Lys | Leu | Ile | Lys |
| 65 | | | | | 70 | | | | 75 | | | | | 80 | |
| Gln | Glu | Leu | Asp | Lys | Tyr | Lys | Asn | Ala | Val | Thr | Asp | Leu | Gln | Leu | Leu |
| | | | | 85 | | | | | 90 | | | | | 95 | |
| Met | Gln | Ser | Thr | Pro | Ala | Thr | Asn | Asn | Gln | Ala | Arg | Gly | Ser | Gly | Ser |
| | | | 100 | | | | | 105 | | | | | 110 | | |
| Gly | Arg | Ser | Leu | Gly | Phe | Leu | Leu | Gly | Val | Gly | Ser | Ala | Ile | Ala | Ser |
| | | 115 | | | | | 120 | | | | | 125 | | | |
| Gly | Val | Ala | Val | Ser | Lys | Val | Leu | His | Leu | Glu | Gly | Glu | Val | Asn | Lys |
| 130 | | | | | 135 | | | | | 140 | | | | | |
| Ile | Lys | Ser | Ala | Leu | Leu | Ser | Thr | Asn | Lys | Ala | Val | Val | Ser | Leu | Ser |
| 145 | | | | | 150 | | | | | 155 | | | | | 160 |
| Asn | Gly | Val | Ser | Val | Leu | Thr | Ser | Lys | Val | Leu | Asp | Leu | Lys | Asn | Tyr |
| | | | | 165 | | | | | 170 | | | | | 175 | |
| Ile | Asp | Lys | Gln | Leu | Leu | Pro | Ile | Val | Asn | Lys | Gln | Ser | Cys | Ser | Ile |
| | | | 180 | | | | | 185 | | | | | 190 | | |
| Pro | Asn | Ile | Glu | Thr | Val | Ile | Glu | Phe | Gln | Gln | Lys | Asn | Asn | Arg | Leu |
| | | | 195 | | | | | 200 | | | | | 205 | | |
| Leu | Glu | Ile | Thr | Arg | Glu | Phe | Ser | Val | Asn | Ala | Gly | Val | Thr | Thr | Pro |
| 210 | | | | | 215 | | | | | 220 | | | | | |
| Val | Ser | Thr | Tyr | Met | Leu | Thr | Asn | Ser | Glu | Leu | Leu | Ser | Leu | Ile | Asn |
| 225 | | | | | 230 | | | | | 235 | | | | | 240 |
| Asp | Met | Pro | Ile | Thr | Asn | Asp | Gln | Lys | Lys | Leu | Met | Ser | Asn | Asn | Val |
| | | | | 245 | | | | | 250 | | | | | 255 | |
| Gln | Ile | Val | Arg | Gln | Gln | Ser | Tyr | Ser | Ile | Met | Ser | Ile | Ile | Lys | Glu |
| | | | 260 | | | | | 265 | | | | | 270 | | |
| Glu | Val | Leu | Ala | Tyr | Val | Val | Gln | Leu | Pro | Leu | Tyr | Gly | Val | Ile | Asp |
| | | | 275 | | | | | 280 | | | | | 285 | | |
| Thr | Pro | Cys | Trp | Lys | Leu | His | Thr | Ser | Pro | Leu | Cys | Thr | Thr | Asn | Thr |
| | | | 290 | | | | | 295 | | | | | 300 | | |
| Lys | Glu | Gly | Ser | Asn | Ile | Cys | Leu | Thr | Arg | Thr | Asp | Arg | Gly | Trp | Tyr |
| 305 | | | | | 310 | | | | | 315 | | | | | 320 |
| Cys | Asp | Asn | Ala | Gly | Ser | Val | Ser | Phe | Phe | Pro | Gln | Ala | Glu | Thr | Cys |
| | | | | 325 | | | | | 330 | | | | | 335 | |
| Lys | Val | Gln | Ser | Asn | Arg | Val | Phe | Cys | Asp | Thr | Met | Asn | Ser | Leu | Thr |
| | | | 340 | | | | | 345 | | | | | 350 | | |
| Leu | Pro | Ser | Glu | Val | Asn | Leu | Cys | Asn | Val | Asp | Ile | Phe | Asn | Pro | Lys |
| | | | 355 | | | | | 360 | | | | | 365 | | |

```
Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
            515                 520                 525
```

<210> SEQ ID NO 46
<211> LENGTH: 528
<212> TYPE: PRT
<213> ORGANISM: Artificial Sequence
<220> FEATURE:
<223> OTHER INFORMATION: A2_F24 N67I+S215P+K80E: A2, linker stabilized,
      fibritin

<400> SEQUENCE: 46

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Glu
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
    115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
```

```
            195                 200                 205
Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525
```

<210> SEQ ID NO 47
<211> LENGTH: 528
<212> TYPE: PRT
<213> ORGANISM: Artificial Sequence
<220> FEATURE:
<223> OTHER INFORMATION: A2_F24 N67I+S215P+K77E: A2, linker stabilized, fibritin

<400> SEQUENCE: 47

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30
```

```
Tyr Gln Ser Thr Cys Ser Ala Val Ser Lys Gly Tyr Leu Ser Ala Leu
             35                  40                  45

Arg Thr Gly Trp Tyr Thr Ser Val Ile Thr Ile Glu Leu Ser Asn Ile
 50                  55                  60

Lys Lys Ile Lys Cys Asn Gly Thr Asp Ala Lys Ile Glu Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Gln Ala Arg Gly Ser Gly Ser
             100                 105                 110

Gly Arg Ser Leu Gly Phe Leu Leu Gly Val Gly Ser Ala Ile Ala Ser
             115                 120                 125

Gly Val Ala Val Ser Lys Val Leu His Leu Glu Gly Glu Val Asn Lys
 130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                 165                 170                 175

Ile Asp Lys Gln Leu Leu Pro Ile Val Asn Lys Gln Ser Cys Ser Ile
             180                 185                 190

Pro Asn Ile Glu Thr Val Ile Glu Phe Gln Gln Lys Asn Asn Arg Leu
             195                 200                 205

Leu Glu Ile Thr Arg Glu Phe Ser Val Asn Ala Gly Val Thr Thr Pro
 210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                 245                 250                 255

Gln Ile Val Arg Gln Gln Ser Tyr Ser Ile Met Ser Ile Ile Lys Glu
             260                 265                 270

Glu Val Leu Ala Tyr Val Val Gln Leu Pro Leu Tyr Gly Val Ile Asp
             275                 280                 285

Thr Pro Cys Trp Lys Leu His Thr Ser Pro Leu Cys Thr Thr Asn Thr
 290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                 325                 330                 335

Lys Val Gln Ser Asn Arg Val Phe Cys Asp Thr Met Asn Ser Leu Thr
             340                 345                 350

Leu Pro Ser Glu Val Asn Leu Cys Asn Val Asp Ile Phe Asn Pro Lys
             355                 360                 365

Tyr Asp Cys Lys Ile Met Thr Ser Lys Thr Asp Val Ser Ser Ser Val
 370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                 405                 410                 415

Cys Asp Tyr Val Ser Asn Lys Gly Val Asp Thr Val Ser Val Gly Asn
             420                 425                 430

Thr Leu Tyr Tyr Val Asn Lys Gln Glu Gly Lys Ser Leu Tyr Val Lys
             435                 440                 445

Gly Glu Pro Ile Ile Asn Phe Tyr Asp Pro Leu Val Phe Pro Ser Asp
```

```
                  450               455               460
Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
                515                 520                 525

<210> SEQ ID NO 48
<211> LENGTH: 528
<212> TYPE: PRT
<213> ORGANISM: Artificial Sequence
<220> FEATURE:
<223> OTHER INFORMATION: A2_F24 N67I+S215P+S46G: A2, linker stabilized,
      fibritin

<400> SEQUENCE: 48

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Gly Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285
```

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
                340                 345                 350

Leu Pro Ser Glu Val Asn Leu Cys Asn Val Asp Ile Phe Asn Pro Lys
                355                 360                 365

Tyr Asp Cys Lys Ile Met Thr Ser Lys Thr Asp Val Ser Ser Ser Val
370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Lys Ser Leu Tyr Val Lys
                435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
                515                 520                 525

<210> SEQ ID NO 49
<211> LENGTH: 528
<212> TYPE: PRT
<213> ORGANISM: Artificial Sequence
<220> FEATURE:
<223> OTHER INFORMATION: A2_F24: RSV S46G A2, linker stabilized,
      fibritin

<400> SEQUENCE: 49

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Gly Ala Leu
                35                  40                  45

Arg Thr Gly Trp Tyr Thr Ser Val Ile Thr Ile Glu Leu Ser Asn Ile
50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
                100                 105                 110

Gly Arg Ser Leu Gly Phe Leu Leu Gly Val Gly Ser Ala Ile Ala Ser
                115                 120                 125

```
Gly Val Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Ser Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu Gly Gly Ile Glu Gly Arg
        515                 520                 525
```

<210> SEQ ID NO 50
<211> LENGTH: 528

```
<212> TYPE: PRT
<213> ORGANISM: Artificial Sequence
<220> FEATURE:
<223> OTHER INFORMATION: A2_F24: RSV K465Q A2, linker stabilized,
      fibritin

<400> SEQUENCE: 50
```

| | | | | | | | | | | | | | | | |
|---|---|---|---|---|---|---|---|---|---|---|---|---|---|---|---|
| Met | Glu | Leu | Leu | Ile | Leu | Lys | Ala | Asn | Ala | Ile | Thr | Thr | Ile | Leu | Thr |
| 1 | | | | 5 | | | | | 10 | | | | | 15 | |
| Ala | Val | Thr | Phe | Cys | Phe | Ala | Ser | Gly | Gln | Asn | Ile | Thr | Glu | Glu | Phe |
| | | 20 | | | | | 25 | | | | | 30 | | | |
| Tyr | Gln | Ser | Thr | Cys | Ser | Ala | Val | Ser | Lys | Gly | Tyr | Leu | Ser | Ala | Leu |
| | | 35 | | | | 40 | | | | | 45 | | | | |
| Arg | Thr | Gly | Trp | Tyr | Thr | Ser | Val | Ile | Thr | Ile | Glu | Leu | Ser | Asn | Ile |
| | 50 | | | | | 55 | | | | | 60 | | | | |
| Lys | Lys | Asn | Lys | Cys | Asn | Gly | Thr | Asp | Ala | Lys | Ile | Lys | Leu | Ile | Lys |
| 65 | | | | | 70 | | | | 75 | | | | | 80 | |
| Gln | Glu | Leu | Asp | Lys | Tyr | Lys | Asn | Ala | Val | Thr | Glu | Leu | Gln | Leu | Leu |
| | | | | 85 | | | | | 90 | | | | | 95 | |
| Met | Gln | Ser | Thr | Pro | Ala | Thr | Asn | Asn | Gln | Ala | Arg | Gly | Ser | Gly | Ser |
| | | | 100 | | | | | 105 | | | | | 110 | | |
| Gly | Arg | Ser | Leu | Gly | Phe | Leu | Leu | Gly | Val | Gly | Ser | Ala | Ile | Ala | Ser |
| | | 115 | | | | | 120 | | | | | 125 | | | |
| Gly | Val | Ala | Val | Ser | Lys | Val | Leu | His | Leu | Glu | Gly | Glu | Val | Asn | Lys |
| 130 | | | | | 135 | | | | | 140 | | | | | |
| Ile | Lys | Ser | Ala | Leu | Leu | Ser | Thr | Asn | Lys | Ala | Val | Val | Ser | Leu | Ser |
| 145 | | | | | 150 | | | | | 155 | | | | | 160 |
| Asn | Gly | Val | Ser | Val | Leu | Thr | Ser | Lys | Val | Leu | Asp | Leu | Lys | Asn | Tyr |
| | | | | 165 | | | | | 170 | | | | | 175 | |
| Ile | Asp | Lys | Gln | Leu | Leu | Pro | Ile | Val | Asn | Lys | Gln | Ser | Cys | Ser | Ile |
| | | | 180 | | | | | 185 | | | | | 190 | | |
| Ser | Asn | Ile | Glu | Thr | Val | Ile | Glu | Phe | Gln | Gln | Lys | Asn | Asn | Arg | Leu |
| | | 195 | | | | | 200 | | | | | 205 | | | |
| Leu | Glu | Ile | Thr | Arg | Glu | Phe | Ser | Val | Asn | Ala | Gly | Val | Thr | Thr | Pro |
| 210 | | | | | 215 | | | | | 220 | | | | | |
| Val | Ser | Thr | Tyr | Met | Leu | Thr | Asn | Ser | Glu | Leu | Leu | Ser | Leu | Ile | Asn |
| 225 | | | | | 230 | | | | | 235 | | | | | 240 |
| Asp | Met | Pro | Ile | Thr | Asn | Asp | Gln | Lys | Lys | Leu | Met | Ser | Asn | Asn | Val |
| | | | | 245 | | | | | 250 | | | | | 255 | |
| Gln | Ile | Val | Arg | Gln | Gln | Ser | Tyr | Ser | Ile | Met | Ser | Ile | Ile | Lys | Glu |
| | | | 260 | | | | | 265 | | | | | 270 | | |
| Glu | Val | Leu | Ala | Tyr | Val | Val | Gln | Leu | Pro | Leu | Tyr | Gly | Val | Ile | Asp |
| | | 275 | | | | | 280 | | | | | 285 | | | |
| Thr | Pro | Cys | Trp | Lys | Leu | His | Thr | Ser | Pro | Leu | Cys | Thr | Thr | Asn | Thr |
| 290 | | | | | 295 | | | | | 300 | | | | | |
| Lys | Glu | Gly | Ser | Asn | Ile | Cys | Leu | Thr | Arg | Thr | Asp | Arg | Gly | Trp | Tyr |
| 305 | | | | | 310 | | | | | 315 | | | | | 320 |
| Cys | Asp | Asn | Ala | Gly | Ser | Val | Ser | Phe | Phe | Pro | Gln | Ala | Glu | Thr | Cys |
| | | | | 325 | | | | | 330 | | | | | 335 | |
| Lys | Val | Gln | Ser | Asn | Arg | Val | Phe | Cys | Asp | Thr | Met | Asn | Ser | Leu | Thr |
| | | | 340 | | | | | 345 | | | | | 350 | | |
| Leu | Pro | Ser | Glu | Val | Asn | Leu | Cys | Asn | Val | Asp | Ile | Phe | Asn | Pro | Lys |
| | | 355 | | | | | 360 | | | | | 365 | | | |
| Tyr | Asp | Cys | Lys | Ile | Met | Thr | Ser | Lys | Thr | Asp | Val | Ser | Ser | Ser | Val |
| 370 | | | | | 375 | | | | | 380 | | | | | |

-continued

```
Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Gln Ser Leu Tyr Val Lys
            435                 440                 445

Gly Glu Pro Ile Ile Asn Phe Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
                515                 520                 525
```

<210> SEQ ID NO 51
<211> LENGTH: 528
<212> TYPE: PRT
<213> ORGANISM: Artificial Sequence
<220> FEATURE:
<223> OTHER INFORMATION: A2_F24: RSV N67I A2, linker stabilized, fibritin

<400> SEQUENCE: 51

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Ser Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
```

```
              210                 215                 220
Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                    245                 250                 255

Gln Ile Val Arg Gln Gln Ser Tyr Ser Ile Met Ser Ile Ile Lys Glu
                260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
        290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                    325                 330                 335

Lys Val Gln Ser Asn Arg Val Phe Cys Asp Thr Met Asn Ser Leu Thr
                340                 345                 350

Leu Pro Ser Glu Val Asn Leu Cys Asn Val Asp Ile Phe Asn Pro Lys
            355                 360                 365

Tyr Asp Cys Lys Ile Met Thr Ser Lys Thr Asp Val Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                    405                 410                 415

Cys Asp Tyr Val Ser Asn Lys Gly Val Asp Thr Val Ser Val Gly Asn
                420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
        450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
                    485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
            515                 520                 525

<210> SEQ ID NO 52
<211> LENGTH: 528
<212> TYPE: PRT
<213> ORGANISM: Artificial Sequence
<220> FEATURE:
<223> OTHER INFORMATION: A2_F24: RSV E92D A2, linker stabilized,
      fibritin

<400> SEQUENCE: 52

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45
```

```
Arg Thr Gly Trp Tyr Thr Ser Val Ile Thr Ile Glu Leu Ser Asn Ile
    50              55              60

Lys Lys Asn Lys Cys Asn Gly Thr Asp Ala Lys Ile Lys Leu Ile Lys
65              70              75                          80

Gln Glu Leu Asp Lys Tyr Lys Asn Ala Val Thr Asp Leu Gln Leu Leu
                85              90              95

Met Gln Ser Thr Pro Ala Thr Asn Asn Gln Ala Arg Gly Ser Gly Ser
            100             105             110

Gly Arg Ser Leu Gly Phe Leu Leu Gly Val Gly Ser Ala Ile Ala Ser
            115             120             125

Gly Val Ala Val Ser Lys Val Leu His Leu Glu Gly Glu Val Asn Lys
130             135             140

Ile Lys Ser Ala Leu Leu Ser Thr Asn Lys Ala Val Val Ser Leu Ser
145             150             155             160

Asn Gly Val Ser Val Leu Thr Ser Lys Val Leu Asp Leu Lys Asn Tyr
                165             170             175

Ile Asp Lys Gln Leu Leu Pro Ile Val Asn Lys Gln Ser Cys Ser Ile
            180             185             190

Ser Asn Ile Glu Thr Val Ile Glu Phe Gln Gln Lys Asn Asn Arg Leu
    195             200             205

Leu Glu Ile Thr Arg Glu Phe Ser Val Asn Ala Gly Val Thr Thr Pro
    210             215             220

Val Ser Thr Tyr Met Leu Thr Asn Ser Glu Leu Leu Ser Leu Ile Asn
225             230             235             240

Asp Met Pro Ile Thr Asn Asp Gln Lys Lys Leu Met Ser Asn Asn Val
                245             250             255

Gln Ile Val Arg Gln Gln Ser Tyr Ser Ile Met Ser Ile Ile Lys Glu
            260             265             270

Glu Val Leu Ala Tyr Val Val Gln Leu Pro Leu Tyr Gly Val Ile Asp
            275             280             285

Thr Pro Cys Trp Lys Leu His Thr Ser Pro Leu Cys Thr Thr Asn Thr
    290             295             300

Lys Glu Gly Ser Asn Ile Cys Leu Thr Arg Thr Asp Arg Gly Trp Tyr
305             310             315             320

Cys Asp Asn Ala Gly Ser Val Ser Phe Phe Pro Gln Ala Glu Thr Cys
                325             330             335

Lys Val Gln Ser Asn Arg Val Phe Cys Asp Thr Met Asn Ser Leu Thr
            340             345             350

Leu Pro Ser Glu Val Asn Leu Cys Asn Val Asp Ile Phe Asn Pro Lys
    355             360             365

Tyr Asp Cys Lys Ile Met Thr Ser Lys Thr Asp Val Ser Ser Ser Val
    370             375             380

Ile Thr Ser Leu Gly Ala Ile Val Ser Cys Tyr Gly Lys Thr Lys Cys
385             390             395             400

Thr Ala Ser Asn Lys Asn Arg Gly Ile Ile Lys Thr Phe Ser Asn Gly
                405             410             415

Cys Asp Tyr Val Ser Asn Lys Gly Val Asp Thr Val Ser Val Gly Asn
            420             425             430

Thr Leu Tyr Tyr Val Asn Lys Gln Glu Gly Lys Ser Leu Tyr Val Lys
            435             440             445

Gly Glu Pro Ile Ile Asn Phe Tyr Asp Pro Leu Val Phe Pro Ser Asp
450             455             460

Glu Phe Asp Ala Ser Ile Ser Gln Val Asn Glu Lys Ile Asn Gln Ser
```

```
                  465                 470                 475                 480
Leu Ala Phe Ile Arg Lys Ser Asp Glu Leu Leu Ser Ala Ile Gly Gly
                485                 490                 495

Tyr Ile Pro Glu Ala Pro Arg Asp Gly Gln Ala Tyr Val Arg Lys Asp
                500                 505                 510

Gly Glu Trp Val Leu Leu Ser Thr Phe Leu Gly Gly Ile Glu Gly Arg
                515                 520                 525

<210> SEQ ID NO 53
<211> LENGTH: 228
<212> TYPE: PRT
<213> ORGANISM: Artificial Sequence
<220> FEATURE:
<223> OTHER INFORMATION: CR9501 heavy chain

<400> SEQUENCE: 53

Gln Val Gln Leu Val Gln Ser Gly Pro Gly Leu Val Lys Pro Ser Gln
1               5                   10                  15

Thr Leu Ala Leu Thr Cys Asn Val Ser Gly Ala Ser Ile Asn Ser Asp
                20                  25                  30

Asn Tyr Tyr Trp Thr Trp Ile Arg Gln Arg Pro Gly Gly Gly Leu Glu
                35                  40                  45

Trp Ile Gly His Ile Ser Tyr Thr Gly Asn Thr Tyr Tyr Thr Pro Ser
    50                  55                  60

Leu Lys Ser Arg Leu Ser Met Ser Leu Glu Thr Ser Gln Ser Gln Phe
65                  70                  75                  80

Ser Leu Arg Leu Thr Ser Val Thr Ala Ala Asp Ser Ala Val Tyr Phe
                85                  90                  95

Cys Ala Ala Cys Gly Ala Tyr Val Leu Ile Ser Asn Cys Gly Trp Phe
                100                 105                 110

Asp Ser Trp Gly Gln Gly Thr Gln Val Thr Val Ser Ser Ala Ser Thr
                115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
            210                 215                 220

Pro Lys Ser Cys
225

<210> SEQ ID NO 54
<211> LENGTH: 12
<212> TYPE: PRT
<213> ORGANISM: Artificial Sequence
<220> FEATURE:
<223> OTHER INFORMATION: CR9501 VH CDR1

<400> SEQUENCE: 54

Gly Ala Ser Ile Asn Ser Asp Asn Tyr Tyr Trp Thr
1               5                   10
```

```
<210> SEQ ID NO 55
<211> LENGTH: 16
<212> TYPE: PRT
<213> ORGANISM: Artificial Sequence
<220> FEATURE:
<223> OTHER INFORMATION: CR9501 VH CDR2

<400> SEQUENCE: 55

His Ile Ser Tyr Thr Gly Asn Thr Tyr Tyr Thr Pro Ser Leu Lys Ser
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: CR9501 VH CDR3

<400> SEQUENCE: 56

Cys Gly Ala Tyr Val Leu Ile Ser Asn Cys Gly Trp Phe Asp Ser
1               5                   10                  15

<210> SEQ ID NO 57
<211> LENGTH: 214
<212> TYPE: PRT
<213> ORGANISM: Artificial Sequence
<220> FEATURE:
<223> OTHER INFORMATION: CR9502 heavy chain

<400> SEQUENCE: 57

Glu Ile Val Met Thr Gln Ser Pro Ser Ser Leu Ser Ala Ser Ile Gly
1               5                   10                  15

Asp Arg Val Thr Ile Thr Cys Gln Ala Ser Gln Asp Ile Ser Thr Tyr
            20                  25                  30

Leu Asn Trp Tyr Gln Gln Lys Pro Gly Gln Ala Pro Arg Leu Leu Ile
        35                  40                  45

Tyr Gly Ala Ser Asn Leu Glu Thr Gly Val Pro Ser Arg Phe Thr Gly
50                  55                  60

Ser Gly Tyr Gly Thr Asp Phe Ser Val Thr Ile Ser Ser Leu Gln Pro
65                  70                  75                  80

Glu Asp Ile Ala Thr Tyr Tyr Cys Gln Gln Tyr Gln Tyr Leu Pro Tyr
                85                  90                  95

Thr Phe Ala Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 58
<211> LENGTH: 10
<212> TYPE: PRT
<213> ORGANISM: Artificial Sequence
<220> FEATURE:
<223> OTHER INFORMATION: CR9502 VH CDR1

<400> SEQUENCE: 58

Gly Phe Thr Phe Ser Gly His Thr Ile Ala
1               5                   10

<210> SEQ ID NO 59
<211> LENGTH: 17
<212> TYPE: PRT
<213> ORGANISM: Artificial Sequence
<220> FEATURE:
<223> OTHER INFORMATION: CR9502 VH CDR2

<400> SEQUENCE: 59

Trp Val Ser Thr Asn Asn Gly Asn Thr Glu Tyr Ala Gln Lys Ile Gln
1               5                   10                  15

Gly

<210> SEQ ID NO 60
<211> LENGTH: 12
<212> TYPE: PRT
<213> ORGANISM: Artificial Sequence
<220> FEATURE:
<223> OTHER INFORMATION: CR9502 VH CDR3

<400> SEQUENCE: 60

Glu Trp Leu Val Met Gly Gly Phe Ala Phe Asp His
1               5                   10

<210> SEQ ID NO 61
<211> LENGTH: 214
<212> TYPE: PRT
<213> ORGANISM: Artificial Sequence
<220> FEATURE:
<223> OTHER INFORMATION: CR9501 light chain

<400> SEQUENCE: 61

Glu Ile Val Met Thr Gln Ser Pro Ser Ser Leu Ser Ala Ser Ile Gly
1               5                   10                  15

Asp Arg Val Thr Ile Thr Cys Gln Ala Ser Gln Asp Ile Ser Thr Tyr
            20                  25                  30

Leu Asn Trp Tyr Gln Gln Lys Pro Gly Gln Ala Pro Arg Leu Leu Ile
        35                  40                  45

Tyr Gly Ala Ser Asn Leu Glu Thr Gly Val Pro Ser Arg Phe Thr Gly
    50                  55                  60

Ser Gly Tyr Gly Thr Asp Phe Ser Val Thr Ile Ser Ser Leu Gln Pro
65                  70                  75                  80

Glu Asp Ile Ala Thr Tyr Tyr Cys Gln Gln Tyr Gln Tyr Leu Pro Tyr
                85                  90                  95

Thr Phe Ala Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200             205

Phe Asn Arg Gly Glu Cys
    210
```

<210> SEQ ID NO 62
<211> LENGTH: 11
<212> TYPE: PRT
<213> ORGANISM: Artificial Sequence
<220> FEATURE:
<223> OTHER INFORMATION: CR9501 VL CDR1

<400> SEQUENCE: 62

```
Gln Ala Ser Gln Asp Ile Ser Thr Tyr Leu Asn
1               5                   10
```

<210> SEQ ID NO 63
<211> LENGTH: 7
<212> TYPE: PRT
<213> ORGANISM: Artificial Sequence
<220> FEATURE:
<223> OTHER INFORMATION: CR9501 VL CDR2

<400> SEQUENCE: 63

```
Gly Ala Ser Asn Leu Glu Thr
1               5
```

<210> SEQ ID NO 64
<211> LENGTH: 9
<212> TYPE: PRT
<213> ORGANISM: Artificial Sequence
<220> FEATURE:
<223> OTHER INFORMATION: CR9501 VL CDR3

<400> SEQUENCE: 64

```
Gln Gln Tyr Gln Tyr Leu Pro Tyr Thr
1               5
```

<210> SEQ ID NO 65
<211> LENGTH: 215
<212> TYPE: PRT
<213> ORGANISM: Artificial Sequence
<220> FEATURE:
<223> OTHER INFORMATION: CR9502 light chain

<400> SEQUENCE: 65

```
Gln Ser Val Leu Thr Gln Ala Ser Ser Val Ser Val Ala Pro Gly Gln
1               5                   10                  15

Thr Ala Arg Ile Thr Cys Gly Ala Asn Asn Ile Gly Ser Gln Asn Val
            20                  25                  30

His Trp Tyr Gln Gln Lys Pro Gly Gln Ala Pro Val Leu Val Val Tyr
        35                  40                  45

Asp Asp Arg Asp Arg Pro Ser Gly Ile Pro Asp Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Arg Asp Gln
                85                  90                  95
```

```
Ala Val Ile Phe Gly Gly Gly Thr Lys Leu Thr Val Leu Gly Gln Pro
            100                 105                 110
Lys Ala Ala Pro Ser Val Thr Leu Phe Pro Pro Ser Ser Glu Glu Leu
            115                 120                 125
Gln Ala Asn Lys Ala Thr Leu Val Cys Leu Ile Ser Asp Phe Tyr Pro
        130                 135                 140
Gly Ala Val Thr Val Ala Trp Lys Ala Asp Ser Ser Pro Val Lys Ala
145                 150                 155                 160
Gly Val Glu Thr Thr Thr Pro Ser Lys Gln Ser Asn Asn Lys Tyr Ala
                165                 170                 175
Ala Ser Ser Tyr Leu Ser Leu Thr Pro Glu Gln Trp Lys Ser His Arg
            180                 185                 190
Ser Tyr Ser Cys Gln Val Thr His Glu Gly Ser Thr Val Glu Lys Thr
        195                 200                 205
Ile Ala Pro Thr Glu Cys Ser
    210                 215

<210> SEQ ID NO 66
<211> LENGTH: 11
<212> TYPE: PRT
<213> ORGANISM: Artificial Sequence
<220> FEATURE:
<223> OTHER INFORMATION: CR9502 VL CDR1

<400> SEQUENCE: 66

Gly Ala Asn Asn Ile Gly Ser Gln Asn Val His
1               5                   10

<210> SEQ ID NO 67
<211> LENGTH: 7
<212> TYPE: PRT
<213> ORGANISM: Artificial Sequence
<220> FEATURE:
<223> OTHER INFORMATION: CR9502 VL CDR2

<400> SEQUENCE: 67

Asp Asp Arg Asp Arg Pro Ser
1               5

<210> SEQ ID NO 68
<211> LENGTH: 12
<212> TYPE: PRT
<213> ORGANISM: Artificial Sequence
<220> FEATURE:
<223> OTHER INFORMATION: CR9502 VL CDR3

<400> SEQUENCE: 68

Gln Val Trp Asp Ser Ser Arg Asp Gln Ala Val Ile
1               5                   10

<210> SEQ ID NO 69
<211> LENGTH: 574
<212> TYPE: PRT
<213> ORGANISM: Artificial Sequence
<220> FEATURE:
<223> OTHER INFORMATION: RSV F protein CL57-v224 full length sequence

<400> SEQUENCE: 69

Met Glu Leu Pro Ile Leu Lys Thr Asn Ala Ile Thr Thr Ile Leu Ala
1               5                   10                  15
Ala Val Thr Leu Cys Phe Ala Ser Ser Gln Asn Ile Thr Glu Glu Phe
            20                  25                  30
```

```
Tyr Gln Ser Thr Cys Ser Ala Val Ser Lys Gly Tyr Leu Ser Ala Leu
             35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Ala Asn Asn Arg Ala Arg Arg Glu Leu Pro
                100                 105                 110

Arg Phe Met Asn Tyr Thr Leu Asn Asn Thr Lys Asn Asn Asn Val Thr
             115                 120                 125

Leu Ser Lys Lys Arg Lys Arg Arg Phe Leu Gly Phe Leu Leu Gly Val
         130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                 165                 170                 175

Ala Val Val Ser Leu Ser Asn Gly Val Ser Val Leu Thr Ser Lys Val
             180                 185                 190

Leu Asp Leu Lys Asn Tyr Ile Asp Lys Gln Leu Leu Pro Ile Val Asn
         195                 200                 205

Lys Gln Ser Cys Ser Ile Ser Asn Ile Glu Thr Val Ile Glu Phe Gln
     210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                 245                 250                 255

Leu Leu Ser Leu Ile Asn Asp Met Pro Ile Thr Asn Asp Gln Lys Lys
             260                 265                 270

Leu Met Ser Asn Asn Val Gln Ile Val Arg Gln Gln Ser Tyr Ser Ile
         275                 280                 285

Met Ser Ile Ile Lys Glu Glu Val Leu Ala Tyr Val Val Gln Leu Pro
     290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                 325                 330                 335

Thr Asp Arg Gly Trp Tyr Cys Asp Asn Ala Gly Ser Val Ser Phe Phe
             340                 345                 350

Pro Gln Ala Glu Thr Cys Lys Val Gln Ser Asn Arg Val Phe Cys Asp
         355                 360                 365

Thr Met Asn Ser Leu Thr Leu Pro Ser Glu Val Asn Leu Cys Asn Ile
     370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                 405                 410                 415

Tyr Gly Lys Thr Lys Cys Thr Ala Ser Asn Lys Asn Arg Gly Ile Ile
             420                 425                 430

Lys Thr Phe Ser Asn Gly Cys Asp Tyr Val Ser Asn Lys Gly Val Asp
         435                 440                 445
```

```
Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Asn Val Gly Lys Ser Thr Thr Asn Ile Met Ile Thr
            515                 520                 525

Thr Ile Ile Ile Val Ile Ile Val Ile Leu Leu Leu Ile Ala Val
        530                 535                 540

Gly Leu Phe Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 70
<211> LENGTH: 513
<212> TYPE: PRT
<213> ORGANISM: Artificial Sequence
<220> FEATURE:
<223> OTHER INFORMATION: Ectodomain, RSV CL57-v224

<400> SEQUENCE: 70

Met Glu Leu Pro Ile Leu Lys Thr Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Asn Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240
```

```
Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu
```

<210> SEQ ID NO 71
<211> LENGTH: 544
<212> TYPE: PRT
<213> ORGANISM: Artificial Sequence
<220> FEATURE:
<223> OTHER INFORMATION: PreF, RSV A2, fibritin

<400> SEQUENCE: 71

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
```

```
            85                  90                  95
Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
            130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
            210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510
```

```
Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
        530                 535                 540

<210> SEQ ID NO 72
<211> LENGTH: 544
<212> TYPE: PRT
<213> ORGANISM: Artificial Sequence
<220> FEATURE:
<223> OTHER INFORMATION: PreF N67I S215P, RSV A2, fibritin

<400> SEQUENCE: 72

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335
```

```
Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
            530                 535                 540

<210> SEQ ID NO 73
<211> LENGTH: 544
<212> TYPE: PRT
<213> ORGANISM: Artificial Sequence
<220> FEATURE:
<223> OTHER INFORMATION: PreF N67I S215P, RSV B1, fibritin

<400> SEQUENCE: 73

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
            35                  40                  45

Arg Thr Gly Trp Tyr Thr Ser Val Ile Thr Ile Glu Leu Ser Asn Ile
        50                  55                  60

Lys Glu Ile Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
            85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
        130                 135                 140

Gly Ser Ala Ile Ala Ser Gly Ile Ala Val Ser Lys Val Leu His Leu
145                 150                 155                 160
```

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Pro Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

<210> SEQ ID NO 74
<211> LENGTH: 544
<212> TYPE: PRT
<213> ORGANISM: Artificial Sequence
<220> FEATURE:

<223> OTHER INFORMATION: RSV N67I S215P, RSV CL57-v224, fibritin

<400> SEQUENCE: 74

```
Met Glu Leu Pro Ile Leu Lys Thr Asn Ala Ile Thr Thr Ile Leu Ala
1               5                   10                  15
Ala Val Thr Leu Cys Phe Ala Ser Ser Gln Asn Ile Thr Glu Glu Phe
            20                  25                  30
Tyr Gln Ser Thr Cys Ser Ala Val Ser Lys Gly Tyr Leu Ser Ala Leu
        35                  40                  45
Arg Thr Gly Trp Tyr Thr Ser Val Ile Thr Ile Glu Leu Ser Asn Ile
    50                  55                  60
Lys Glu Ile Lys Cys Asn Gly Thr Asp Ala Lys Val Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Ala Ala Asn Asn Arg Ala Arg Arg Glu Leu Pro
            100                 105                 110
Arg Phe Met Asn Tyr Thr Leu Asn Asn Thr Lys Asn Asn Asn Val Thr
        115                 120                 125
Leu Ser Lys Lys Arg Lys Arg Arg Phe Leu Gly Phe Leu Leu Gly Val
    130                 135                 140
Gly Ser Ala Ile Ala Ser Gly Ile Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asp Lys Gln Leu Leu Pro Ile Val Asn
        195                 200                 205
Lys Gln Ser Cys Ser Ile Pro Asn Ile Glu Thr Val Ile Glu Phe Gln
    210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Ile
    370                 375                 380
Asp Ile Phe Asn Pro Lys Tyr Asp Cys Lys Ile Met Thr Ser Lys Thr
385                 390                 395                 400
```

```
Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
        530                 535                 540

<210> SEQ ID NO 75
<211> LENGTH: 522
<212> TYPE: PRT
<213> ORGANISM: Artificial Sequence
<220> FEATURE:
<223> OTHER INFORMATION: PreFL N67I S215P, RSV CL57-v224, fibritin, Loop

<400> SEQUENCE: 75

Met Glu Leu Pro Ile Leu Lys Thr Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Gln Ala Arg Gly Ser Gly Ser
            100                 105                 110

Gly Arg Ser Leu Gly Phe Leu Leu Gly Val Gly Ser Ala Ile Ala Ser
        115                 120                 125

Gly Ile Ala Val Ser Lys Val Leu His Leu Glu Gly Glu Val Asn Lys
    130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220
```

Val Ser Thr Tyr Met Leu Thr Asn Ser Glu Leu Ser Leu Ile Asn
225                 230                 235                 240

Asp Met Pro Ile Thr Asn Asp Gln Lys Lys Leu Met Ser Asn Asn Val
            245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
            275                 280                 285

Thr Pro Cys Trp Lys Leu His Thr Ser Pro Leu Cys Thr Thr Asn Thr
            290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
            325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Ile Asp Ile Phe Asn Pro Lys
            355                 360                 365

Tyr Asp Cys Lys Ile Met Thr Ser Lys Thr Asp Val Ser Ser Ser Val
            370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
            405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
            450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu Ser Ala Ile Gly Gly
            485                 490                 495

Tyr Ile Pro Glu Ala Pro Arg Asp Gly Gln Ala Tyr Val Arg Lys Asp
            500                 505                 510

Gly Glu Trp Val Leu Leu Ser Thr Phe Leu
            515                 520

<210> SEQ ID NO 76
<211> LENGTH: 544
<212> TYPE: PRT
<213> ORGANISM: Artificial Sequence
<220> FEATURE:
<223> OTHER INFORMATION: PreF N67I S215P E487Q, RSV A2, fibritin

<400> SEQUENCE: 76

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

-continued

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Gln Phe Asp Ala Ser Ile Ser Gln Val Asn

```
                      485                 490                 495
Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
                515                 520                 525

Ala Tyr Val Arg Lys Asp Gly Glu Trp Val Leu Leu Ser Thr Phe Leu
                530                 535                 540

<210> SEQ ID NO 77
<211> LENGTH: 544
<212> TYPE: PRT
<213> ORGANISM: Artificial Sequence
<220> FEATURE:
<223> OTHER INFORMATION: PreF N67I S215P K201N, RSV A2, fibritin

<400> SEQUENCE: 77

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Asn Gln Leu Leu Pro Ile Val Asn
            195                 200                 205

Lys Gln Ser Cys Ser Ile Pro Asn Ile Glu Thr Val Ile Glu Phe Gln
        210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
```

```
            305                 310                 315                 320
Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
                370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
                450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
                515                 520                 525

Ala Tyr Val Arg Lys Asp Gly Glu Trp Val Leu Leu Ser Thr Phe Leu
                530                 535                 540

<210> SEQ ID NO 78
<211> LENGTH: 544
<212> TYPE: PRT
<213> ORGANISM: Artificial Sequence
<220> FEATURE:
<223> OTHER INFORMATION: PreF N67I S215P E92D, RSV A2, fibritin

<400> SEQUENCE: 78

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
                35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Asn Asn Arg Ala Arg Arg Glu Leu Pro
                100                 105                 110

Arg Phe Met Asn Tyr Thr Leu Asn Asn Ala Lys Lys Thr Asn Val Thr
                115                 120                 125

Leu Ser Lys Lys Arg Lys Arg Arg Phe Leu Gly Phe Leu Leu Gly Val
```

```
            130                 135                 140
Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
            195                 200                 205

Lys Gln Ser Cys Ser Ile Pro Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
530                 535                 540

<210> SEQ ID NO 79
```

<211> LENGTH: 544
<212> TYPE: PRT
<213> ORGANISM: Artificial Sequence
<220> FEATURE:
<223> OTHER INFORMATION: PreF N67I S215P D486N, RSV A2, fibritin

<400> SEQUENCE: 79

```
Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu
        35                  40                  45
Arg Thr Gly Trp Tyr Thr Ser Val Ile Thr Ile Glu Leu Ser Asn Ile
    50                  55                  60
Lys Lys Ile Lys Cys Asn Gly Thr Asp Ala Lys Ile Lys Leu Ile Lys
65                  70                  75                  80
Gln Glu Leu Asp Lys Tyr Lys Asn Ala Val Thr Glu Leu Gln Leu Leu
                85                  90                  95
Met Gln Ser Thr Pro Ala Thr Asn Asn Arg Ala Arg Arg Glu Leu Pro
            100                 105                 110
Arg Phe Met Asn Tyr Thr Leu Asn Asn Ala Lys Lys Thr Asn Val Thr
        115                 120                 125
Leu Ser Lys Lys Arg Lys Arg Arg Phe Leu Gly Phe Leu Leu Gly Val
    130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asp Lys Gln Leu Leu Pro Ile Val Asn
        195                 200                 205
Lys Gln Ser Cys Ser Ile Pro Asn Ile Glu Thr Val Ile Glu Phe Gln
    210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
    290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
    370                 375                 380
```

```
Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asn Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
530                 535                 540

<210> SEQ ID NO 80
<211> LENGTH: 574
<212> TYPE: PRT
<213> ORGANISM: Artificial Sequence
<220> FEATURE:
<223> OTHER INFORMATION: Fwt N67I S215P, membrane-bound RSV F, A2

<400> SEQUENCE: 80

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
            85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
            130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205
```

Lys Gln Ser Cys Ser Ile Pro Asn Ile Glu Thr Val Ile Glu Phe Gln
                210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                    245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                    325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                    405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                    485                 490                 495

Glu Lys Ile Asn Gln Ser Leu Ala Phe Ile Arg Lys Ser Asp Glu Leu
                500                 505                 510

Leu His Asn Val Asn Ala Val Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 81
<211> LENGTH: 552
<212> TYPE: PRT
<213> ORGANISM: Artificial Sequence
<220> FEATURE:
<223> OTHER INFORMATION: Fs1 N67I S215P, membrane-bound RSV F, A2

<400> SEQUENCE: 81

```
Met Glu Leu Leu Ile Leu Lys Ala Asn Ala Ile Thr Thr Ile Leu Thr
 1               5                  10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Gln Ala Arg Gly Ser Gly Ser
                100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
        130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
                180                 185                 190

Pro Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415
```

```
Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
            435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu His Asn Val Asn Ala
            485                 490                 495

Val Lys Ser Thr Thr Asn Ile Met Ile Thr Thr Ile Ile Ile Val Ile
            500                 505                 510

Ile Val Ile Leu Leu Ser Leu Ile Ala Val Gly Leu Leu Leu Tyr Cys
            515                 520                 525

Lys Ala Arg Ser Thr Pro Val Thr Leu Ser Lys Asp Gln Leu Ser Gly
            530                 535                 540

Ile Asn Asn Ile Ala Phe Ser Asn
545                 550
```

<210> SEQ ID NO 82
<211> LENGTH: 574
<212> TYPE: PRT
<213> ORGANISM: Artificial Sequence
<220> FEATURE:
<223> OTHER INFORMATION: Fwt N67I S215P E92D, membrane-bound RSV F, A2

<400> SEQUENCE: 82

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
        130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220
```

-continued

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Asn Ala Val Lys Ser Thr Thr Asn Ile Met Ile Thr
    515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 83
<211> LENGTH: 552
<212> TYPE: PRT
<213> ORGANISM: Artificial Sequence
<220> FEATURE:
<223> OTHER INFORMATION: Fsl N67I S215P E92D, membrane-bound RSV F, A2

<400> SEQUENCE: 83

Met Glu Leu Leu Ile Leu Lys Ala Asn Ala Ile Thr Thr Ile Leu Thr
1               5                   10                  15

-continued

```
Ala Val Thr Phe Cys Phe Ala Ser Gly Gln Asn Ile Thr Glu Phe
             20                  25                  30

Tyr Gln Ser Thr Cys Ser Ala Val Ser Lys Gly Tyr Leu Ser Ala Leu
         35                  40                  45

Arg Thr Gly Trp Tyr Thr Ser Val Ile Thr Ile Glu Leu Ser Asn Ile
 50                  55                  60

Lys Lys Ile Lys Cys Asn Gly Thr Asp Ala Lys Ile Lys Leu Ile Lys
 65                  70                  75                  80

Gln Glu Leu Asp Lys Tyr Lys Asn Ala Val Thr Asp Leu Gln Leu Leu
                 85                  90                  95

Met Gln Ser Thr Pro Ala Thr Asn Asn Gln Ala Arg Gly Ser Gly Ser
             100                 105                 110

Gly Arg Ser Leu Gly Phe Leu Leu Gly Val Gly Ser Ala Ile Ala Ser
         115                 120                 125

Gly Val Ala Val Ser Lys Val Leu His Leu Glu Gly Glu Val Asn Lys
 130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                 165                 170                 175

Ile Asp Lys Gln Leu Leu Pro Ile Val Asn Lys Gln Ser Cys Ser Ile
             180                 185                 190

Pro Asn Ile Glu Thr Val Ile Glu Phe Gln Gln Lys Asn Asn Arg Leu
         195                 200                 205

Leu Glu Ile Thr Arg Glu Phe Ser Val Asn Ala Gly Val Thr Thr Pro
 210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                 245                 250                 255

Gln Ile Val Arg Gln Gln Ser Tyr Ser Ile Met Ser Ile Ile Lys Glu
             260                 265                 270

Glu Val Leu Ala Tyr Val Val Gln Leu Pro Leu Tyr Gly Val Ile Asp
         275                 280                 285

Thr Pro Cys Trp Lys Leu His Thr Ser Pro Leu Cys Thr Thr Asn Thr
 290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                 325                 330                 335

Lys Val Gln Ser Asn Arg Val Phe Cys Asp Thr Met Asn Ser Leu Thr
             340                 345                 350

Leu Pro Ser Glu Val Asn Leu Cys Asn Val Asp Ile Phe Asn Pro Lys
         355                 360                 365

Tyr Asp Cys Lys Ile Met Thr Ser Lys Thr Asp Val Ser Ser Ser Val
 370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                 405                 410                 415

Cys Asp Tyr Val Ser Asn Lys Gly Val Asp Thr Val Ser Val Gly Asn
             420                 425                 430

Thr Leu Tyr Tyr Val Asn Lys Gln Glu Gly Lys Ser Leu Tyr Val Lys
```

```
        435                 440                 445
Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu His Asn Val Asn Ala
                    485                 490                 495

Val Lys Ser Thr Thr Asn Ile Met Ile Thr Thr Ile Ile Val Ile
                500                 505                 510

Ile Val Ile Leu Leu Ser Leu Ile Ala Val Gly Leu Leu Tyr Cys
            515                 520                 525

Lys Ala Arg Ser Thr Pro Val Thr Leu Ser Lys Asp Gln Leu Ser Gly
530                 535                 540

Ile Asn Asn Ile Ala Phe Ser Asn
545                 550
```

<210> SEQ ID NO 84
<211> LENGTH: 574
<212> TYPE: PRT
<213> ORGANISM: Artificial Sequence
<220> FEATURE:
<223> OTHER INFORMATION: Fwt N67I S215P E487Q, membrane-bound RSV F, A2

<400> SEQUENCE: 84

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys G 245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
            275                 280                 285
Met Ser Ile Ile Lys Glu Glu Val Leu Ala Tyr Val Val Gln Leu Pro
            290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
            325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
            355                 360                 365
Thr Met Asn Ser Leu Thr Leu Pro Ser Glu Val Asn Leu Cys Asn Val
            370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
            405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Gln Glu Gly
            450                 455                 460
Lys Ser Leu Tyr Val Lys Gly Glu Pro Ile Ile Asn Phe Tyr Asp Pro
465                 470                 475                 480
Leu Val Phe Pro Ser Asp Gln Phe Asp Ala Ser Ile Ser Gln Val Asn
            485                 490                 495
Glu Lys Ile Asn Gln Ser Leu Ala Phe Ile Arg Lys Ser Asp Glu Leu
            500                 505                 510
Leu His Asn Val Asn Ala Val Lys Ser Thr Thr Asn Ile Met Ile Thr
            515                 520                 525
Thr Ile Ile Ile Val Ile Ile Val Ile Leu Leu Ser Leu Ile Ala Val
            530                 535                 540
Gly Leu Leu Leu Tyr Cys Lys Ala Arg Ser Thr Pro Val Thr Leu Ser
545                 550                 555                 560
Lys Asp Gln Leu Ser Gly Ile Asn Asn Ile Ala Phe Ser Asn
            565                 570

<210> SEQ ID NO 85
<211> LENGTH: 552
<212> TYPE: PRT
<213> ORGANISM: Artificial Sequence
<220> FEATURE:
<223> OTHER INFORMATION: Fsl N67I S215P E487Q, membrane-bound RSV F, A2

<400> SEQUENCE: 85

Met Glu Leu Leu Ile Leu Lys Ala Asn Ala Ile Thr Thr Ile Leu Thr
1               5                   10                  15
Ala Val Thr Phe Cys Phe Ala Ser Gly Gln Asn Ile Thr Glu Glu Phe
            20                  25                  30
Tyr Gln Ser Thr Cys Ser Ala Val Ser Lys Gly Tyr Leu Ser Ala Leu

```
                35                  40                  45
Arg Thr Gly Trp Tyr Thr Ser Val Ile Thr Ile Glu Leu Ser Asn Ile
 50                  55                  60
Lys Lys Ile Lys Cys Asn Gly Thr Asp Ala Lys Ile Lys Leu Ile Lys
 65                  70                  75                  80
Gln Glu Leu Asp Lys Tyr Lys Asn Ala Val Thr Glu Leu Gln Leu Leu
                 85                  90                  95
Met Gln Ser Thr Pro Ala Thr Asn Asn Gln Ala Arg Gly Ser Gly Ser
                100                 105                 110
Gly Arg Ser Leu Gly Phe Leu Leu Gly Val Gly Ser Ala Ile Ala Ser
            115                 120                 125
Gly Val Ala Val Ser Lys Val Leu His Leu Glu Gly Glu Val Asn Lys
            130                 135                 140
Ile Lys Ser Ala Leu Leu Ser Thr Asn Lys Ala Val Val Ser Leu Ser
145                 150                 155                 160
Asn Gly Val Ser Val Leu Thr Ser Lys Val Leu Asp Leu Lys Asn Tyr
                165                 170                 175
Ile Asp Lys Gln Leu Leu Pro Ile Val Asn Lys Gln Ser Cys Ser Ile
            180                 185                 190
Pro Asn Ile Glu Thr Val Ile Glu Phe Gln Gln Lys Asn Asn Arg Leu
            195                 200                 205
Leu Glu Ile Thr Arg Glu Phe Ser Val Asn Ala Gly Val Thr Thr Pro
210                 215                 220
Val Ser Thr Tyr Met Leu Thr Asn Ser Glu Leu Leu Ser Leu Ile Asn
225                 230                 235                 240
Asp Met Pro Ile Thr Asn Asp Gln Lys Lys Leu Met Ser Asn Asn Val
                245                 250                 255
Gln Ile Val Arg Gln Ser Tyr Ser Ile Met Ser Ile Ile Lys Glu
            260                 265                 270
Glu Val Leu Ala Tyr Val Val Gln Leu Pro Leu Tyr Gly Val Ile Asp
            275                 280                 285
Thr Pro Cys Trp Lys Leu His Thr Ser Pro Leu Cys Thr Thr Asn Thr
290                 295                 300
Lys Glu Gly Ser Asn Ile Cys Leu Thr Arg Thr Asp Arg Gly Trp Tyr
305                 310                 315                 320
Cys Asp Asn Ala Gly Ser Val Ser Phe Phe Pro Gln Ala Glu Thr Cys
                325                 330                 335
Lys Val Gln Ser Asn Arg Val Phe Cys Asp Thr Met Asn Ser Leu Thr
            340                 345                 350
Leu Pro Ser Glu Val Asn Leu Cys Asn Val Asp Ile Phe Asn Pro Lys
            355                 360                 365
Tyr Asp Cys Lys Ile Met Thr Ser Lys Thr Asp Val Ser Ser Ser Val
            370                 375                 380
Ile Thr Ser Leu Gly Ala Ile Val Ser Cys Tyr Gly Lys Thr Lys Cys
385                 390                 395                 400
Thr Ala Ser Asn Lys Asn Arg Gly Ile Ile Lys Thr Phe Ser Asn Gly
                405                 410                 415
Cys Asp Tyr Val Ser Asn Lys Gly Val Asp Thr Val Ser Val Gly Asn
            420                 425                 430
Thr Leu Tyr Tyr Val Asn Lys Gln Glu Gly Lys Ser Leu Tyr Val Lys
            435                 440                 445
Gly Glu Pro Ile Ile Asn Phe Tyr Asp Pro Leu Val Phe Pro Ser Asp
450                 455                 460
```

```
Gln Phe Asp Ala Ser Ile Ser Gln Val Asn Glu Lys Ile Asn Gln Ser
465                 470                 475                 480

Leu Ala Phe Ile Arg Lys Ser Asp Glu Leu Leu His Asn Val Asn Ala
                485                 490                 495

Val Lys Ser Thr Thr Asn Ile Met Ile Thr Thr Ile Ile Val Ile
            500                 505                 510

Ile Val Ile Leu Leu Ser Leu Ile Ala Val Gly Leu Leu Tyr Cys
        515                 520                 525

Lys Ala Arg Ser Thr Pro Val Thr Leu Ser Lys Asp Gln Leu Ser Gly
530                 535                 540

Ile Asn Asn Ile Ala Phe Ser Asn
545                 550
```

<210> SEQ ID NO 86
<211> LENGTH: 574
<212> TYPE: PRT
<213> ORGANISM: Artificial Sequence
<220> FEATURE:
<223> OTHER INFORMATION: Fwt N67I S215P D486N, membrane-bound RSV F, A2

<400> SEQUENCE: 86

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270
```

```
Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asn Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
    515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 87
<211> LENGTH: 552
<212> TYPE: PRT
<213> ORGANISM: Artificial Sequence
<220> FEATURE:
<223> OTHER INFORMATION: Fs1 N67I S215P D486N, membrane-bound RSV F, A2

<400> SEQUENCE: 87

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60
```

```
Lys Ile Lys Cys Asn Gly Thr Asp Ala Lys Ile Lys Leu Ile Lys
 65                  70                  75                  80

Gln Glu Leu Asp Lys Tyr Lys Asn Ala Val Thr Glu Leu Gln Leu Leu
             85                  90                  95

Met Gln Ser Thr Pro Ala Thr Asn Asn Gln Ala Arg Gly Ser Gly Ser
             100                 105                 110

Gly Arg Ser Leu Gly Phe Leu Leu Gly Val Gly Ser Ala Ile Ala Ser
             115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
             165                 170                 175

Ile Asp Lys Gln Leu Leu Pro Ile Val Asn Lys Gln Ser Cys Ser Ile
             180                 185                 190

Pro Asn Ile Glu Thr Val Ile Glu Phe Gln Gln Lys Asn Asn Arg Leu
             195                 200                 205

Leu Glu Ile Thr Arg Glu Phe Ser Val Asn Ala Gly Val Thr Thr Pro
210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
             245                 250                 255

Gln Ile Val Arg Gln Gln Ser Tyr Ser Ile Met Ser Ile Ile Lys Glu
             260                 265                 270

Glu Val Leu Ala Tyr Val Val Gln Leu Pro Leu Tyr Gly Val Ile Asp
             275                 280                 285

Thr Pro Cys Trp Lys Leu His Thr Ser Pro Leu Cys Thr Thr Asn Thr
             290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
             325                 330                 335

Lys Val Gln Ser Asn Arg Val Phe Cys Asp Thr Met Asn Ser Leu Thr
             340                 345                 350

Leu Pro Ser Glu Val Asn Leu Cys Asn Val Asp Ile Phe Asn Pro Lys
             355                 360                 365

Tyr Asp Cys Lys Ile Met Thr Ser Lys Thr Asp Val Ser Ser Ser Val
             370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
             405                 410                 415

Cys Asp Tyr Val Ser Asn Lys Gly Val Asp Thr Val Ser Val Gly Asn
             420                 425                 430

Thr Leu Tyr Tyr Val Asn Lys Gln Glu Gly Lys Ser Leu Tyr Val Lys
             435                 440                 445

Gly Glu Pro Ile Ile Asn Phe Tyr Asp Pro Leu Val Phe Pro Ser Asn
             450                 455                 460

Glu Phe Asp Ala Ser Ile Ser Gln Val Asn Glu Lys Ile Asn Gln Ser
465                 470                 475                 480
```

```
Leu Ala Phe Ile Arg Lys Ser Asp Glu Leu Leu His Asn Val Asn Ala
                485                 490                 495

Val Lys Ser Thr Thr Asn Ile Met Ile Thr Thr Ile Ile Val Ile
            500                 505                 510

Ile Val Ile Leu Leu Ser Leu Ile Ala Val Gly Leu Leu Leu Tyr Cys
            515                 520                 525

Lys Ala Arg Ser Thr Pro Val Thr Leu Ser Lys Asp Gln Leu Ser Gly
            530                 535                 540

Ile Asn Asn Ile Ala Phe Ser Asn
545                 550

<210> SEQ ID NO 88
<211> LENGTH: 574
<212> TYPE: PRT
<213> ORGANISM: Artificial Sequence
<220> FEATURE:
<223> OTHER INFORMATION: Fwt N67I S215P S46G, membrane-bound RSV F, A2

<400> SEQUENCE: 88

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285
```

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
        515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 89
<211> LENGTH: 552
<212> TYPE: PRT
<213> ORGANISM: Artificial Sequence
<220> FEATURE:
<223> OTHER INFORMATION: Fsl N67I S215P S46G, membrane-bound RSV F, A2

<400> SEQUENCE: 89

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

```
Gln Glu Leu Asp Lys Tyr Lys Asn Ala Val Thr Glu Leu Gln Leu Leu
             85                  90                  95

Met Gln Ser Thr Pro Ala Thr Asn Asn Gln Ala Arg Gly Ser Gly Ser
            100                 105                 110

Gly Arg Ser Leu Gly Phe Leu Leu Gly Val Gly Ser Ala Ile Ala Ser
            115                 120                 125

Gly Val Ala Val Ser Lys Val Leu His Leu Glu Gly Glu Val Asn Lys
        130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Pro Asn Ile Glu Thr Val Ile Glu Phe Gln Gln Lys Asn Asn Arg Leu
            195                 200                 205

Leu Glu Ile Thr Arg Glu Phe Ser Val Asn Ala Gly Val Thr Thr Pro
        210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
        370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu His Asn Val Asn Ala
                485                 490                 495

Val Lys Ser Thr Thr Asn Ile Met Ile Thr Thr Ile Ile Ile Val Ile
```

```
                    500             505             510
Ile Val Ile Leu Leu Ser Leu Ile Ala Val Gly Leu Leu Leu Tyr Cys
            515             520             525

Lys Ala Arg Ser Thr Pro Val Thr Leu Ser Lys Asp Gln Leu Ser Gly
            530             535             540

Ile Asn Asn Ile Ala Phe Ser Asn
545             550

<210> SEQ ID NO 90
<211> LENGTH: 544
<212> TYPE: PRT
<213> ORGANISM: Artificial Sequence
<220> FEATURE:
<223> OTHER INFORMATION: PreF N67I E161P S215P E487Q, RSV A2, fibritin

<400> SEQUENCE: 90

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Pro Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
```

```
            305                 310                 315                 320
Leu Cys Thr Thr Asn Thr Lys Glu Gly Ser Asn Ile Cys Leu Thr Arg
                    325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Gln Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

<210> SEQ ID NO 91
<211> LENGTH: 544
<212> TYPE: PRT
<213> ORGANISM: Artificial Sequence
<220> FEATURE:
<223> OTHER INFORMATION: PreF N67I E161P S215P, RSV A2, fibritin

<400> SEQUENCE: 91

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
```

```
            130                 135                 140
Gly Ser Ala Ile Ala Ser Gly Val Ala Val Ser Lys Val Leu His Leu
145                 150                 155                 160

Pro Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
                195                 200                 205

Lys Gln Ser Cys Ser Ile Pro Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
                275                 280                 285

Met Ser Ile Ile Lys Glu Glu Val Leu Ala Tyr Val Val Gln Leu Pro
                290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
                370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
                450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
                515                 520                 525

Ala Tyr Val Arg Lys Asp Gly Glu Trp Val Leu Leu Ser Thr Phe Leu
530                 535                 540
```

<210> SEQ ID NO 92

```
<211> LENGTH: 544
<212> TYPE: PRT
<213> ORGANISM: Artificial Sequence
<220> FEATURE:
<223> OTHER INFORMATION: PreF N67I S173P S215P, RSV A2, fibritin

<400> SEQUENCE: 92

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Pro Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Pro Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380
```

```
Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
530                 535                 540
```

<210> SEQ ID NO 93
<211> LENGTH: 544
<212> TYPE: PRT
<213> ORGANISM: Artificial Sequence
<220> FEATURE:
<223> OTHER INFORMATION: PreF N67I S182P S215P, RSV A2, fibritin

<400> SEQUENCE: 93

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
50                  55                  60

Lys Lys Ile Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
            85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
            130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
            165                 170                 175

Ala Val Val Ser Leu Pro Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205
```

Lys Gln Ser Cys Ser Ile Pro Asn Ile Glu Thr Val Ile Glu Phe Gln
            210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
530                 535                 540

<210> SEQ ID NO 94
<211> LENGTH: 544
<212> TYPE: PRT
<213> ORGANISM: Artificial Sequence
<220> FEATURE:
<223> OTHER INFORMATION: PreF N67I S215P D486C E487C, RSV A2, fibritin

<400> SEQUENCE: 94

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

```
Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
 50                  55                  60

Lys Lys Ile Lys Cys Asn Gly Thr Asp Ala Lys Ile Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Pro Asn Ile Glu Thr Val Ile Glu Phe Gln
            210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445
```

Thr Val Ser Val Gly Asn Thr Leu Tyr Tyr Val Asn Lys Gln Glu Gly
                450                 455                 460

Lys Ser Leu Tyr Val Lys Gly Glu Pro Ile Ile Asn Phe Tyr Asp Pro
465                 470                 475                 480

Leu Val Phe Pro Ser Cys Cys Phe Asp Ala Ser Ile Ser Gln Val Asn
                    485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
                515                 520                 525

Ala Tyr Val Arg Lys Asp Gly Glu Trp Val Leu Leu Ser Thr Phe Leu
        530                 535                 540

<210> SEQ ID NO 95
<211> LENGTH: 16
<212> TYPE: PRT
<213> ORGANISM: Artificial Sequence
<220> FEATURE:
<223> OTHER INFORMATION: Synthesized sequence

<400> SEQUENCE: 95

Lys Val Gln Gln Glu Leu Ser Arg Pro Gly Met Leu Glu Met Leu Leu
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Synthesized sequence

<400> SEQUENCE: 96

Lys Ile Gln Gln Glu Leu Ala Lys Pro Gly Val Leu Glu Arg Phe Val
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Synthesized sequence

<400> SEQUENCE: 97

Ser Val Leu Pro Asn Leu Leu Val Pro Gly Ile Cys Glu Ala Ile Lys
1               5                   10                  15

<210> SEQ ID NO 98
<211> LENGTH: 17
<212> TYPE: PRT
<213> ORGANISM: Artificial Sequence
<220> FEATURE:
<223> OTHER INFORMATION: Synthesized sequence

<400> SEQUENCE: 98

Ile Lys Thr Pro Leu Val Asp Asp Leu Pro Gly Ala Glu Glu Ala Met
1               5                   10                  15

Ser

<210> SEQ ID NO 99
<211> LENGTH: 17
<212> TYPE: PRT
<213> ORGANISM: Artificial Sequence
<220> FEATURE:
<223> OTHER INFORMATION: Synthesized sequence

```
<400> SEQUENCE: 99

Ile Met Gln Ile Leu Val Thr Val Val Pro Ala Leu Glu Lys Leu Ser
1               5                   10                  15

Lys

<210> SEQ ID NO 100
<211> LENGTH: 14
<212> TYPE: PRT
<213> ORGANISM: Artificial Sequence
<220> FEATURE:
<223> OTHER INFORMATION: Synthesized Sequence

<400> SEQUENCE: 100

Val Val Val Leu Ser Pro Glu Leu Gln Ile Lys Asp Tyr Ile
1               5                   10
```